US011896616B2

(12) United States Patent
Kamiya et al.

(10) Patent No.: US 11,896,616 B2
(45) Date of Patent: Feb. 13, 2024

(54) STIMULATORY CELL LINES FOR EX VIVO EXPANSION AND ACTIVATION OF NATURAL KILLER CELLS

(71) Applicant: National University of Singapore, Singapore (SG)

(72) Inventors: Takahiro Kamiya, Singapore (SG); Dario Campana, Singapore (SG)

(73) Assignee: National University of Singapore, Singapore (SG)

( * ) Notice: Subject to any disclaimer, the term of this patent is extended or adjusted under 35 U.S.C. 154(b) by 669 days.

(21) Appl. No.: 16/497,682

(22) PCT Filed: Mar. 27, 2018

(86) PCT No.: PCT/SG2018/050138
§ 371 (c)(1),
(2) Date: Sep. 25, 2019

(87) PCT Pub. No.: WO2018/182511
PCT Pub. Date: Oct. 4, 2018

(65) Prior Publication Data

US 2020/0016208 A1 Jan. 16, 2020

Related U.S. Application Data

(60) Provisional application No. 62/477,311, filed on Mar. 27, 2017.

(51) Int. Cl.

| | |
|---|---|
| ***A61K 35/17*** | (2015.01) |
| ***C07K 14/54*** | (2006.01) |
| ***C07K 16/28*** | (2006.01) |
| ***C12N 5/0783*** | (2010.01) |

(52) U.S. Cl.
CPC .......... *A61K 35/17* (2013.01); *C07K 14/5443* (2013.01); *C07K 16/2809* (2013.01); *C12N 5/0646* (2013.01); *C07K 2317/622* (2013.01); *C12N 2502/30* (2013.01); *C12N 2510/04* (2013.01); *C12N 2740/10043* (2013.01)

(58) Field of Classification Search
CPC .... A61K 35/17; C07K 14/5443; C07K 14/54; C12N 2510/04
See application file for complete search history.

(56) References Cited

U.S. PATENT DOCUMENTS 4,650,764 A 3/1987 Temin et al.
4,690,915 A 9/1987 Rosenberg
4,844,893 A 7/1989 Honsik et al.
4,980,289 A 12/1990 Temin et al.
5,124,263 A 6/1992 Temin et al.
5,359,046 A 10/1994 Capon
5,399,346 A 3/1995 Anderson et al.
5,653,977 A 8/1997 Saleh
5,674,704 A 10/1997 Goodwin et al.
5,686,281 A 11/1997 Roberts
5,712,149 A 1/1998 Roberts
6,103,521 A 8/2000 Capon et al.
6,303,121 B1 10/2001 Kwon
6,319,494 B1 11/2001 Capon et al.
6,355,476 B1 3/2002 Kwon
6,361,998 B1 3/2002 Bell et al.
6,410,319 B1 6/2002 Raubitschek et al.
6,797,514 B2 9/2004 Berenson et al.
7,052,906 B1 5/2006 Lawson et al.
7,070,995 B2 7/2006 Jensen
7,435,596 B2 10/2008 Campana et al.
7,446,179 B2 11/2008 Jensen et al.
7,446,190 B2 11/2008 Sadelain et al.
7,763,243 B2 7/2010 Lum et al.
7,932,055 B2 4/2011 Spee et al.
7,994,298 B2 8/2011 Zhang et al.
8,026,097 B2 9/2011 Campana et al.
(Continued)

FOREIGN PATENT DOCUMENTS

CN 101684456 A * 3/2010
CN 101684456 A 3/2010
(Continued)

OTHER PUBLICATIONS

Denman et al. Membrane-Bound IL-21 Promotes Sustained Ex Vivo Proliferation of Human Natural Killer Cells. PLos One. Jan. 2012 | vol. 7 | Issue 1 | e30264 (Year: 2012).*
AASEQ1_05172022_135256_pep_vs AASEQ2_05172022_135256_pep_align_4-1BBL (Year: 2022).*
CN-101684456_machine translation (Google Patents) (Year: 2022).*
Alignment IL-18 (Year: 2022).*
GenBank Accession No. NM_172175.2, *Homo sapiens* interleukin 15 (IL15), transcript variant 2, mRNA, dated Feb. 12, 2011, 4 pages.
Leitner et al., "T cell stimulator cellsm an efficient and versatile cellular system to assess the role of costimulatory ligands in the activation of human T cells," Journal of Immunological Methods, 362, 131-141, 2010.
(Continued)

*Primary Examiner* — Amy E Juedes
*Assistant Examiner* — Brian Hartnett
(74) *Attorney, Agent, or Firm* — Hamilton, Brook, Smith & Reynolds, P.C.

(57) ABSTRACT

The present invention relates to genetically engineered cell populations derived from an immortalised/cancerous cell that do not express MHC class I molecules but that are modified to express membrane-bound IL-15, membrane-bound 4-1 BBL ligand, and at least one other membrane bound molecule, such as an interleukin or anti-CD3 antibody. The co-culture of said cells with a population of immune cells results in the activation and expansion of at least one subpopulation of immune cells. Expanded populations of NK cells derived from the co-culture of a mixed cell culture with the stimulatory cell lines may be used in methods of treating cancer or an infectious disease. In a separate embodiment, a plurality of nucleic acids for use in preparing the engineered cell population are provided.

9 Claims, 4 Drawing Sheets

Specification includes a Sequence Listing.

(56) References Cited

U.S. PATENT DOCUMENTS

| | | | |
|---|---|---|---|
| 8,399,645 | B2 | 3/2013 | Campana et al. |
| 9,487,800 | B2 | 11/2016 | Schonfeld et al. |
| 9,605,049 | B2 | 3/2017 | Campana et al. |
| 9,834,590 | B2 | 12/2017 | Campana et al. |
| 9,856,322 | B2 | 1/2018 | Campana et al. |
| 10,428,305 | B2 | 10/2019 | Campana et al. |
| 10,774,311 | B2 | 9/2020 | Campana et al. |
| 11,365,236 | B2 | 6/2022 | Leong et al. |
| 11,560,548 | B2 | 1/2023 | Campana et al. |
| 2002/0018783 | A1 | 2/2002 | Sadelain et al. |
| 2003/0147869 | A1 | 8/2003 | Riley |
| 2003/0215427 | A1 | 11/2003 | Jensen |
| 2004/0038886 | A1 | 2/2004 | Finney et al. |
| 2004/0043401 | A1 | 3/2004 | Sadelain et al. |
| 2004/0126363 | A1 | 7/2004 | Jensen et al. |
| 2005/0042208 | A1 | 2/2005 | Sagawa et al. |
| 2005/0048549 | A1 | 3/2005 | Cao et al. |
| 2005/0113564 | A1 | 5/2005 | Campana et al. |
| 2006/0093605 | A1 | 5/2006 | Campana et al. |
| 2006/0247191 | A1 | 11/2006 | Finney et al. |
| 2007/0160578 | A1 | 7/2007 | Waldmann et al. |
| 2007/0166327 | A1 | 7/2007 | Cooper et al. |
| 2008/0247990 | A1 | 10/2008 | Campbell |
| 2012/0015434 | A1 | 1/2012 | Campana et al. |
| 2012/0148552 | A1 | 6/2012 | Jensen |
| 2012/0282256 | A1 | 11/2012 | Campana et al. |
| 2012/0321666 | A1 | 12/2012 | Copper et al. |
| 2013/0266551 | A1 | 10/2013 | Campana et al. |
| 2013/0280221 | A1 | 10/2013 | Schonfeld et al. |
| 2013/0288368 | A1 | 10/2013 | June et al. |
| 2014/0023626 | A1 | 1/2014 | Peled et al. |
| 2014/0271635 | A1 | 9/2014 | Brogdon et al. |
| 2014/0286973 | A1 | 9/2014 | Powell, Jr. |
| 2014/0302608 | A1 | 10/2014 | Dominici et al. |
| 2015/0139943 | A1 | 5/2015 | Campana et al. |
| 2015/0190471 | A1 | 7/2015 | Copik et al. |
| 2015/0218649 | A1 | 8/2015 | Saenger et al. |
| 2016/0000828 | A1 | 1/2016 | Campana et al. |
| 2016/0152723 | A1 | 6/2016 | Chen et al. |
| 2016/0158285 | A1 | 6/2016 | Cooper et al. |
| 2017/0044227 | A1 | 2/2017 | Schonfeld |
| 2017/0073423 | A1 | 3/2017 | Juillerat et al. |
| 2017/0073638 | A1 | 3/2017 | Campana et al. |
| 2017/0129967 | A1 | 5/2017 | Wels et al. |
| 2017/0283482 | A1 | 10/2017 | Campana et al. |
| 2017/0355957 | A1 | 12/2017 | Biondi et al. |
| 2018/0002397 | A1 | 1/2018 | Shah et al. |
| 2018/0044391 | A1 | 2/2018 | Gundram et al. |
| 2018/0086831 | A1 | 3/2018 | Pule et al. |
| 2018/0104278 | A1 | 4/2018 | Zhang et al. |
| 2018/0117146 | A1 | 5/2018 | Yu et al. |
| 2018/0134765 | A1 | 5/2018 | Landgraf et al. |
| 2019/0038733 | A1 | 2/2019 | Campana et al. |
| 2019/0046571 | A1 | 2/2019 | Campana et al. |
| 2019/0290693 | A1 | 9/2019 | Qi et al. |
| 2019/0336533 | A1 | 11/2019 | Hwang et al. |
| 2019/0376037 | A1 | 12/2019 | Campana et al. |
| 2020/0131244 | A1 | 4/2020 | Leong et al. |
| 2020/0255803 | A1 | 8/2020 | Zhang et al. |
| 2020/0407686 | A1 | 12/2020 | Campana et al. |
| 2021/0017271 | A1 | 1/2021 | Tan et al. |
| 2021/0046115 | A1 | 2/2021 | Seow et al. |
| 2021/0054409 | A1 | 2/2021 | Zhu et al. |
| 2021/0324388 | A1 | 10/2021 | Vinanica et al. |
| 2023/0002471 | A1 | 1/2023 | Leong et al. |
| 2023/0220343 | A1 | 7/2023 | Campana et al. |

FOREIGN PATENT DOCUMENTS

| | | | |
|---|---|---|---|
| CN | 106459914 | A | 1/2013 |
| CN | 102924596 | A | 2/2013 |
| CN | 103113470 | A | 5/2013 |
| CN | 105838677 | A | 8/2016 |
| CN | 105985931 | A | 10/2016 |
| CN | 107109363 | A | 8/2017 |
| CN | 107709548 | A | 2/2018 |
| CN | 107827990 | A | 3/2018 |
| EP | 1 053 301 | B1 | 4/2004 |
| EP | 1 820 017 | | 6/2006 |
| EP | 1 233 058 | B1 | 12/2006 |
| EP | 1 036 327 | B1 | 7/2009 |
| EP | 2 411 507 | | 9/2010 |
| EP | 2 493 485 | | 5/2011 |
| EP | 2 493 486 | | 5/2011 |
| EP | 2 593 540 | | 1/2012 |
| EP | 2 141 997 | B1 | 10/2012 |
| EP | 2 614 151 | | 10/2012 |
| EP | 2 756 521 | | 3/2013 |
| EP | 2 866 834 | | 1/2014 |
| EP | 2 903 637 | | 4/2014 |
| EP | 2 904 106 | | 4/2014 |
| EP | 2 948 544 | | 7/2014 |
| EP | 2 961 831 | | 9/2014 |
| EP | 2 964 753 | | 9/2014 |
| EP | 2 970 426 | | 9/2014 |
| EP | 2 968 601 | | 10/2014 |
| EP | 2 986 636 | | 10/2014 |
| EP | 2 537 416 | | 11/2014 |
| EP | 3 008 173 | | 12/2014 |
| EP | 2 856 876 | A1 | 4/2015 |
| EP | 3 057 986 | | 4/2015 |
| EP | 3 063 175 | | 5/2015 |
| EP | 3 071 221 | | 5/2015 |
| EP | 3 071 222 | | 5/2015 |
| EP | 3 071 223 | | 5/2015 |
| EP | 3 083 671 | | 6/2015 |
| EP | 3 083 691 | | 6/2015 |
| EP | 3 094 653 | | 7/2015 |
| EP | 3 105 318 | | 8/2015 |
| EP | 3 105 335 | | 8/2015 |
| EP | 2 968 492 | | 9/2015 |
| EP | 3 119 425 | | 9/2015 |
| EP | 3 126 380 | | 10/2015 |
| EP | 3 134 432 | | 10/2015 |
| EP | 3 180 359 | | 2/2016 |
| EP | 3 189 132 | | 3/2016 |
| EP | 3 012 268 | A1 | 4/2016 |
| EP | 2 614 077 | B1 | 8/2016 |
| EP | 3 115 573 | A1 | 1/2017 |
| EP | 3 567 049 | A2 | 11/2019 |
| JP | 2017-112982 | A | 6/2017 |
| WF | WO 2006/061626 | A2 | 6/2006 |
| WO | WO 00/23573 | A2 | 4/2000 |
| WO | WO 02/077029 | A2 | 10/2002 |
| WO | WO 03/089616 | A2 | 10/2003 |
| WO | WO 2004/027036 | A2 | 4/2004 |
| WO | WO 2004/039840 | A1 | 5/2004 |
| WO | 2005/000890 | A1 | 1/2005 |
| WO | WO 2005/044996 | A2 | 5/2005 |
| WO | WO 2005/118788 | A2 | 12/2005 |
| WO | WO 2006/036445 | A2 | 4/2006 |
| WO | WO 2006/052534 | A2 | 5/2006 |
| WO | WO 2007/046006 | A2 | 4/2007 |
| WO | WO 2008/121420 | A1 | 10/2008 |
| WO | WO 2009/117566 | A1 | 9/2009 |
| WO | WO 2010/071836 | A1 | 6/2010 |
| WO | WO 2010/110734 | A1 | 9/2010 |
| WO | WO 2011/020047 | A1 | 2/2011 |
| WO | WO 2011/053321 | A1 | 5/2011 |
| WO | WO 2011/053322 | A1 | 5/2011 |
| WO | WO 2011/069019 | A2 | 6/2011 |
| WO | WO 2011/080740 | A1 | 7/2011 |
| WO | WO 2011/150976 | A1 | 12/2011 |
| WO | WO 2012/009422 | A1 | 1/2012 |
| WO | WO 2012/031744 | A1 | 3/2012 |
| WO | WO 2012/040323 | A2 | 3/2012 |
| WO | WO 2012/071411 | A2 | 5/2012 |
| WO | WO 2012/079000 | A1 | 6/2012 |
| WO | WO 2012/136231 | A1 | 10/2012 |
| WO | 2013/043196 | A1 | 3/2013 |
| WO | WO 2013/040371 | A2 | 3/2013 |
| WO | WO 2013/040557 | A2 | 3/2013 |
| WO | WO 2013/123720 | A2 | 8/2013 |
| WO | WO 2013/123726 | A1 | 8/2013 |

(56) References Cited

FOREIGN PATENT DOCUMENTS

| | | | |
|---|---|---|---|
| WO | WO 2014/005072 A1 | 1/2014 | |
| WO | WO 2014/011993 A2 | 1/2014 | |
| WO | WO 2014/055413 A2 | 4/2014 | |
| WO | WO 2014/055442 A2 | 4/2014 | |
| WO | WO 2014/055657 A | 4/2014 | |
| WO | WO 2014/055668 A1 | 4/2014 | |
| WO | WO 2014/099671 A1 | 6/2014 | |
| WO | WO 2014/117121 A1 | 7/2014 | |
| WO | 2 956 175 | 8/2014 | |
| WO | WO 2014/127261 A1 | 8/2014 | |
| WO | WO 2014/134165 A1 | 9/2014 | |
| WO | WO 2014/138704 A1 | 9/2014 | |
| WO | WO 2014/145252 A2 | 9/2014 | |
| WO | WO 2014/164554 A1 | 10/2014 | |
| WO | WO 2014/172584 A1 | 10/2014 | |
| WO | WO 2014/186469 A2 | 11/2014 | |
| WO | WO 2014/201021 A2 | 12/2014 | |
| WO | WO 2015/058018 A1 | 4/2015 | |
| WO | WO 2015/066551 A2 | 5/2015 | |
| WO | WO 2015/075468 A1 | 5/2015 | |
| WO | WO 2015/075469 A1 | 5/2015 | |
| WO | WO 2015/075470 A1 | 5/2015 | |
| WO | WO 2015/092024 A2 | 6/2015 | |
| WO | WO 2015/095895 A1 | 6/2015 | |
| WO | WO 2015/120421 A1 | 8/2015 | |
| WO | WO 2015/123642 A1 | 8/2015 | |
| WO | WO 2015/142314 A1 | 9/2015 | |
| WO | WO 2015/142661 A1 | 9/2015 | |
| WO | WO 2015/150771 A1 | 10/2015 | |
| WO | WO 2015/154012 A1 | 10/2015 | |
| WO | WO 2015/154012 A8 | 10/2015 | |
| WO | WO 2015/164759 A2 | 10/2015 | |
| WO | WO 2015/174928 A1 | 11/2015 | |
| WO | WO-2015174928 A1 * | 11/2015 | A61K 35/17 |
| WO | 2015/188119 A1 | 12/2015 | |
| WO | WO 2015/193411 A1 | 12/2015 | |
| WO | WO 2016/011210 A2 | 1/2016 | |
| WO | WO 2016/030691 A1 | 3/2016 | |
| WO | WO 2016/033331 A1 | 3/2016 | |
| WO | WO 2016/040441 A1 | 3/2016 | |
| WO | WO 2016/042041 A | 3/2016 | |
| WO | WO 2016/042461 A1 | 3/2016 | |
| WO | WO 2016/061574 A1 | 4/2016 | |
| WO | WO 2016/069607 A1 | 5/2016 | |
| WO | WO 2016/073602 A2 | 5/2016 | |
| WO | WO 2016/073629 A1 | 5/2016 | |
| WO | WO 2016/073755 A2 | 5/2016 | |
| WO | WO 2016/075612 A1 | 5/2016 | |
| WO | WO 2016/100985 A2 | 6/2016 | |
| WO | 2016/118857 A1 | 7/2016 | |
| WO | WO 2015/105522 A1 | 7/2016 | |
| WO | WO 2016/109661 A1 | 7/2016 | |
| WO | WO 2016/109668 A1 | 7/2016 | |
| WO | WO 2016/115482 A1 | 7/2016 | |
| WO | WO 2016/123122 A1 | 8/2016 | |
| WO | WO 2016/123333 A1 | 8/2016 | |
| WO | WO 2016/124765 A1 | 8/2016 | |
| WO | WO 2016/124930 A1 | 8/2016 | |
| WO | WO 2016/126213 A1 | 8/2016 | |
| WO | WO 2016/126608 A1 | 8/2016 | |
| WO | 2016/139487 A1 | 9/2016 | |
| WO | WO 2016/141357 A1 | 9/2016 | |
| WO | WO 2016/142314 A1 | 9/2016 | |
| WO | WO 2016/149254 A1 | 9/2016 | |
| WO | WO 2016/151315 A1 | 9/2016 | |
| WO | WO 2016/154055 A1 | 9/2016 | |
| WO | WO 2016/154585 A1 | 9/2016 | |
| WO | WO 2016/172537 A1 | 10/2016 | |
| WO | WO 2016/172583 A1 | 10/2016 | |
| WO | WO 2016/174405 A1 | 11/2016 | |
| WO | WO 2016/174406 A1 | 11/2016 | |
| WO | WO 2016/174407 A1 | 11/2016 | |
| WO | WO 2016/174408 A1 | 11/2016 | |
| WO | WO 2016/174409 A1 | 11/2016 | |
| WO | WO 2016/174461 A1 | 11/2016 | |
| WO | WO 2016/174652 A1 | 11/2016 | |
| WO | WO 2016/179684 A1 | 11/2016 | |
| WO | WO 2016/191587 A1 | 12/2016 | |
| WO | WO 2016/191755 A1 | 12/2016 | |
| WO | WO 2016/196388 A1 | 12/2016 | |
| WO | WO 2016/197108 A1 | 12/2016 | |
| WO | WO 2016/201304 A1 | 12/2016 | |
| WO | WO 2016/210293 A1 | 12/2016 | |
| WO | WO 2017/004150 A1 | 1/2017 | |
| WO | WO 2017/011804 A1 | 1/2017 | |
| WO | WO 2017/021701 A1 | 2/2017 | |
| WO | WO 2017/023859 A1 | 2/2017 | |
| WO | WO 2017/024131 A1 | 2/2017 | |
| WO | WO 2017/027325 A1 | 2/2017 | |
| WO | WO 2017/029511 A1 | 2/2017 | |
| WO | WO 2017/032777 A1 | 3/2017 | |
| WO | WO 2017/034615 A1 | 3/2017 | |
| WO | WO 2017/037083 A1 | 3/2017 | |
| WO | WO 2017/058752 A1 | 4/2017 | |
| WO | WO 2017/058753 A1 | 4/2017 | |
| WO | WO 2017/079694 A2 | 5/2017 | |
| WO | WO 2017/079705 A1 | 5/2017 | |
| WO | WO 2017/079881 A1 | 5/2017 | |
| WO | WO 2017/096329 A1 | 6/2017 | |
| WO | WO 2017/127729 A1 | 7/2017 | |
| WO | WO 2017/172981 A2 | 10/2017 | |
| WO | WO 2018/022646 A1 | 2/2018 | |
| WO | 2018106732 A1 | 6/2018 | |
| WO | WO 2018/103503 A1 | 6/2018 | |
| WO | 2018124766 A2 | 7/2018 | |
| WO | WO 2018/182511 A1 | 10/2018 | |
| WO | WO 2018/183385 A1 | 10/2018 | |
| WO | WO 2019/062817 A1 | 4/2019 | |
| WO | WO 2019/077037 A1 | 4/2019 | |
| WO | 2019129220 A1 | 7/2019 | |
| WO | WO 2019/129002 A1 | 7/2019 | |
| WO | WO 2019/155286 A2 | 8/2019 | |
| WO | WO 2019/155288 A1 | 8/2019 | |
| WO | WO 2019/193476 A1 | 10/2019 | |
| WO | WO 2020/044239 A1 | 3/2020 | |
| WO | WO 2020/083282 A1 | 4/2020 | |
| WO | WO 2021/009694 A1 | 1/2021 | |

OTHER PUBLICATIONS

Wang et al., "Human NK cells maintain licensing status and are subject to killer immunoglobulin-like receptor (KIR) and KIR-ligand inhibition following ex vivo expansion," Cancer Immunol Immunother, 65:1047-1059, 2016.

Extended European Search Report and Written Opinion dated Dec. 10, 2020 for International Application No. PCT/SG2018/050138, entitled "Stimulatory Cell Lines for Ex Vivo Expansion and Activation of Natural Killer Cells".

Oyer et al., "Natural killer cells stimulated with PM21 particles expand and biodistribute in vivo: Clinical implications for cancer treatment," Cytotherapy, 18: 653-663, 2016.

Search Report and Written Opinion for Singapore Application No. 11201908337V, titled, "Stimulatory cell lines for ex vivo expansion and activation of natural killer cells," Date Completed: Nov. 25, 2020.

Caratelli et al., "FCγ Chimeric Receptor-Engineered T Cells: Methodology, Advantages, Limitations, and Clinical Relevance," Front Immunol., vol. 8, Article 457 , 8 pages (Apr. 27, 2017).

Hombach, A.A., et al., "Costimulation by chimeric antigen receptors revisited: the T cell antitumor response benefits from combined CD28-OX40 signalling", Int. J. Cancer, 129, 2935-2944 (2011).

Hurton, L.V. et al., "Tethered IL-15 augments antitumor activity and promotes a stem-cell memory subset in tumor-specific T cells," PCNAS, USA, 113(48): E7788-E7797 (Nov. 2016).

Kober, J., et al. "The capacity of the TNF family members 4-1BBL, OX40L, CD70, GITRL, CD30L and LIGHT to costimulate human T cells," Eur J Immuno, vol. 38, No. 10, pp. 2678-2688 (Oct. 28, 2008).

NCIthesaurus, Bicistronic chimeric antigen reeptor vector, retrieved online from: https://ncit.nci.nih.gov/ncitbrowser/pages/home.jsf.jsessionid=12B0F7AF71E9A4035C38B5E4F6C055B0, retrieved on: Jan. 21, 2021.

(56) References Cited

OTHER PUBLICATIONS

Gillet et al., Selectable Markers for Gene Therapy, Chapter 26 of Gene and Cell Therapy: Therapeutic Mechanisms and Strategies, 3rd Ed. N .S. Templeton Ed, (CRC Press:Bpca Ratpm. FL), pp. 555 and 558, 2009.
Suerth et al., "Efficient Generation of Gene-Modified Human Natural Killer Cells via Alpharetroviral Vectors," J. Mol. Med. 94:83-93, 2016, published online Aug. 25, 2015.
Sokolic et al., "A Selectable Bicistronic Retroviral Vector Corrects the Molecular Defect in a Cell Line Derived from a Patient with Leukocyte Adhesion Deficiency," Biol. Blood Marrow Transpl. 12(2) Suppl 1: 20-21. Feb. 2006.
Ang, S.O. et al., "Avoiding the need for clinical-grade OKT3: ex vivo expansion of T cells using artificial antigen presenting cells genetically modified to crosslink CD3" Biology of Blood and Marrow Transplantation, Jan. 9, 2012, vol. 8, No. 2, pp. S258.
Steel et al., "Interleukin-15 biology and its therapeutic implications in cancer," Trends Pharmacol. Sci. 33(1) :35-41, Jan. 2012.
Gacerez, A, et al., "How Chimeric Antigen Receptor Design Affects Adoptive T Cell Therapy," Journal of Cellular Physiology, vol. 231, No. 12, pp. 2590-2598; Jun. 2, 2016.
Sadelain, M. et al., "The Basic Principles of Chimeric Antigen Receptor Design," Cancer Discovery, vol. 3, No. 4, pp. 388-398 (Apr. 1, 2013).
Bridgeman, J.S. et al., "The Optimal Antigen Response of Chimeric Antigen Receptors Harboring the CD3* Transmembrane Domain is Dependent upon Incorporation of the Receptor into the Endogenous TCR/CD3 Complex," J Immunol, 184(12): 6938-6949 ( May 2010).
De La Chapelle, A. et al., "Truncated erythropoietin receptor causes dominantly inherited benign human erythrocytosis," Proc Natl Acad Sci USA., vol. 90, No. 10, pp. 4495-4499 (May 1993).
Galustian, C. et al., "MP84-07A Tale of Tails—A Novel Approach to Immunotherapy of Prostate Cancer," J Urol, 195(4S): e1092 (May 2016).
Hoffmann, S.C. et al. "2B4 Engagement Mediates Rapid LFA-1 and Actin-Dependent NK Cell Adhesion to Tumor Cells as Measured by Single Cell Force Spectroscopy," J. Immunol, 186(5): 2757-2764 (Jan. 2011).
Minamoto, S. et al., "Acquired Erythopoietin Responsiveness of Interleukin-2-dependent T lymphocytes Retrovirally Transduced with Genes Encoding Chimeric Erythropoietin/Interleukin-2 Receptors," Blood, vol. 86, No. 6, pp. 2281-2287 (Sep. 1995).
Mohammed, S. et al., "Improving Chimeric Antigen Receptor-Modified T Cell Function by Reversing the Immunosuppressive Tumor Microenvironment of Pancreatic Cancer," Mol. Ther. 4, vol. 25, No. 1, pp. 249-258 (Jan. 2017).
Wilkie, S. et al., "Selective Expansion of Chimeric Antigen Receptor-targeted T-cells with Potent Effector Function Using Interleukin-4," J Biol Chem., vol. 285, No. 33, pp. 25538-25544 (Jun. 2010).
Abken, H. et al., "Antigen-specific T-cell activation independently of the MHC: chimeric antigen receptor-redirected T cells," Frontiers in Immunology, V. 4, Article 371, c. 4 (2013).
Calabrese, et al., "IL-6 biology: implications for clinical targeting in rheumatic disease," S. Nat. Rev. Rheumatol, 10, 720-727 (2014); published online Aug. 19, 2014 (corrected online Sep. 19, 2014).
Cordoba, S.P. et al., "The large ectodomains of CD45 and CD148 regulate their segregation from and inhibition of ligated T-cell receptor," Blood, The Journal of the American Society of Hematology, V. 121, N. 21, p. 4295-4302, c. 4301 (2013).
Culpepper, D.J. et al., "Systematic mutation and thermodynamic analysis of central tyrosine pairs in polyspecific NKG2D receptor interactions," Molecular Immunology, V. 48, N. 4, p. 516-523, c. 521-522 (2011).
De Felipe, P., "Polycistronic Viral Vectors," Current Gene Therapy, V. 2, N. 3, p. 355-378, c. 360 (2002).
Lanier, Lewis L., "NK Cell Recognition," Annual Review of Immunology, vol. 23, No. 1, pp. 225-274 (2005).
Lima, et al., "Interleukin-6 Neutralization by Antibodies Immobilized at the Surface of Polymeric Nanoparticles as a Therapeutic Strategy for Arthritic Diseases," ACS Appl. Mater. Interfaces 2018, 10, 13839-13850.
Zhao, Y. et al., "A Herceptin-Based Chimeric Antigen Receptor with Modified Signaling Domains Leads to Enhanced Survival of Transduced T Lymphocytes and Antitumor Activity," The Journal of Immunology, V. 183, N. 9, p. 5563-5574, c. 5568, 5571 (2009).
U.S. Appl. No. 60/383,872, filed May 28, 2002, Sadelain et al.
Abken et al., "Chimeric T-cell receptors: highly specific tools to target cytotoxic T-lymphocytes to tumour cells," Cancer Treat Rev., 23(2):97-112, Mar. 1997.
Abken, H., et al., "Tuning tumor-specific T-cell activation: a matter of costimulation?" TRENDS in Immunol. 23: 240-245 (2002).
Aguera-Gonzalez et al., "Palmitoylation of MICA, a ligand for NKGZD, mediates its recruitment to membrane microdomains and promotes its shedding," Eur. J. Immunol. vol. 41, pp. 3667-3676 (2011).
Alderson et al., "Molecular and Biological Characterization of Human 4-1BB and its Ligand," Eur. J. Immunol., 1994, 24: 2219-2227.
Allison and Lanier, "Structure, function, and serology of the T-cell antigen receptor complex," Annu Rev Immunol, 1987, 5:503-40.
Alvarez-Vallina, L. and Hawkins, R.E., "Antigen-specific targeting of CD28-mediated T cell co-stimulation using chimeric single-chain antibody variable fragment-CD28 receptors," Eur. J. Immunol. 26: 2304-2309 (1996).
Annenkov, A., et al., "Engineering mouse T lymphocytes specific to type II collagen by transduction with a chimeric receptor consisting of a single chain Fv and TCR zeta," Gene Therapy 7: 714-722 (2000).
Antony, G.K., et al., "Interleukin 2 in cancer therapy," Curr Med Chem., 17(29): 3297-3302 (2010).
Aoudjit and Vuori., "Integrin Signaling in Cancer Cell Survival and Chemoresistance," Chemotherapy Research and Practice, 2012(Article ID 283181), 16 pages, 2012.
Appelbaum, "Haematopoietic cell transplantation as immunotherapy," Nature, 2001, 411(6835): 385-389.
Aruffo, A., et al., "Molecular cloning of a CD28 cDNA by a high-efficiency COS cell expression system," Proc. Natl. Acad. Sci, 1987, 84:8573-8577.
ATCC No. CCL-243, 1975.
Azuma, M, et al., "Functional Expression of B7/BB1 on Activated T Lymphocytes," J. EXp. Med. 177: 845-850 (1993).
Baek, H.J. et al., "Ex vivo expansion of natural killer cells using cryopreserved irradiated feeder cells," *Anticancer Research*, 33: 2011-2020 (2013).
Barber et al., "Chimeric NKG2D Expressing T Cells Eliminated Immosuppression and Activate Immunity within the Ovarian Tumor Microenvironment," J. Immunol, vol. 183, pp. 6939-6947 (2009).
Barber et al., "Chimeric NKGZD Receptor-Bearing T Cells as lmmunotherapy for Ovarian Cancer," American Association for Cancer, vol. 67, No. 10, pp. 5003-5008, (May 15, 2007).
Barber et al., "Chimeric NKG2D receptor-expressing T cells as an immunotherapy for multiple myeloma," Experimental Hematology, vol. 36, pp. 1318-1328, (2008).
Barber et al., "Chimeric NKG2D T Cells Require Both T Cell- and Host-Derived Cytokine Secretion and Perforin Expression to Increase Tumor Antigen Presentation and Systemic Immunity," J. Immunol, vol. 183, pp. 2365-2372 (2009).
Barber et al., "Immunotherapy with Chimeric NKGZD Receptors Leads to Long-Term Tumor-Free Survival and Development of Host Antitumor Immunity in Murine Ovarian Cancer," J. Immunol., vol. 180, pp. 72-78, (2008).
Barber et al., "Treatment of multiple myeloma With adoptively transferred chimeric NKGZD receptor-expressing T cells," Gene Therapy, vol. 18, pp. 509-516, (2011).
Barrett, D.M., et al., "Chimeric Antigen Receptor Therapy for Cancer," Annu Rev. Med. 65: 333-347 (2014).
Bartholomew et al., "Mesenchymal stem cells suppress lymphocyte proliferation in vitro and prolong skin graft survival in vivo," Exp Hematol, Jan.y 2002, 30(1): 42-8.

(56) References Cited

OTHER PUBLICATIONS

Batlcvi, C.L., ct al. "Novel immunothcrapics in lymphoid malignancies," Nature Rev. Clin. Oncol.13:25-40 (2016).
Baum et al., "Side effects of retroviral gene transfer into hematopoietic stem cells," Blood, Mar. 2003, 101(6): 2099-114.
Bejcek et al., "Development and Characterization of Three Recombinant Single Chain Antibody Fragments (scFvs) Directed against the CD19 Antigen," Cancer Res., 1995, 55:2346-2351.
Berger, C. et al., "Safety and immunologic effects of IL-15 administration in nonhuman primates," *Blood*, 114(12): 2417-2426 (2009).
Besser, M.J., et al., "Adoptive Transfer of Tumor-Infiltrating Lymphocytes in Patients with Metastatic Melanoma: Intent-to-Treat Analysis and Efficacy after Failure to Prior Immunotherapies," Clin. Cancer Res. 19: 4792-4800 (2013).
Better et al., "Manufacturing and Characterization of KTE-C19 in a Multicenter Trial of Subjects with Refractory Aggressive Non-Hodgkin Lymphoma (NHL) (ZUMA-1)," Poster session presented at the American Association for Cancer Research Annual Meeting, New Orleans, Louisiana (2016).
Billadeau et al., "NKG2D-DAP10 triggers human NK cell-mediated killing via a Syk-independent regulatory pathway," Nat Immunol, Jun. 2003, 4(6): 557-64.
Bischof et al., "Autonomous induction of proliferation, JNK and NK-xB activation in primary resting T cells by mobilized CD28," Eur J Immunol., 30(3):876-882, Mar. 2000.
Bork et al., "The innnunoglobulin fold. Structural classification, sequence patterns and common core," J Mol Biol., 242(4):309-320, Sep. 30, 1994.
Boyman, O., et al., "The role of interleukin-2 during homeostasis and activation of the immune system," *Nat Rev Immunol.*, 12: 180-190 (2012).
Brentjens et al., "Eradication of Systemic B-Cell Tumors by Genetically Targeted Human T Lymphocytes Co-Stimulated By CD80 and Interleukin-15," Nature Medicine, 2003, 9: 279-286.
Brentjens, R.J., et al., "CD19-Targeted T Cells Rapidly Induce Molecular Remissions in Adults with Chemotherapy-Refractory Acute Lymphoblastic Leukemia," Sci. Trans. Med. 5: 1-9 (2013).
Brentjens, R.J., et al., "Safety and persistence of adoptively transferred autologous CD19-targeted T cells in patients with relapsed or chemotherapy refractory B-cell leukemias," Blood 119(18): 4817-4828 (2011).
Bridgeman, J.S., et al., "Building Better Chimeric Antigen Receptors for Adoptive T Cell Therapy," Current Gene Therapy 10: 77-90 (2010).
Brocker et al., "New simplified molecular design for functional T cell receptor," Eur J Immunol., 23(7):1435-1439, Jul. 1993.
Bromley et al., "The immunological synapse and CD28-CD80 interactions," Nat Immunol., 2(12):1159-1166, Dec. 2001.
Bronte, V., and Mocellin, S., "Suppressive Influences in the Immune Response to Cancer," J. Immunother . 32: 1-11 (2009).
Budagian, V. et al., "IL-15/IL-15 receptor biology: A guided tour through an expanding universe," *Cytokine & Growth Factor Reviews*, 17: 259-280 (2006).
Bukczynski et al., "Costimulation of Human CD28-T Cells by 4-1BB Ligand," Eur. J. Immunol., 2003, 33: 446-454.
Burkett, P.R. et al., "Coordinate expression and trans presentation of interleukin (IL)-15Ralpha and IL-15 supports natural killer cell and memory CD8+ T cell homeostasis," *J Exp Med.*, 200(7): 825-834 (2004).
Caligiuri et al., "Immunotherapeutic approaches for hematologic malignancies," Hematology Am Soc Hematol Educ Program, 2004, 37-53.
Campana et al., "Immunophenotyping of Leukemia," Journal of Immunol Methods, 2000, 243: 59-75.
Cardoso AA, et al. Pre-B acute lymphoblastic leukemia cells may induce T-cell anergy to alloantigen. Blood 88:41-48 (1996).
Carson, W.E. et al., "A potential role for interleukin-15 in the regulation of human natural killer cell survival," J Clin Invest, 99(5): 937-943 (1997).
Carter, P., et al., "Identification and validation of cell surface antigens for antibody targeting in oncology," Endocrine-Related Cancer 11: 659-687 (2004).
Cesano, A., et al. "Reversal of Acute Myelogenous Leukemia in Humanized SCID Mice Using a Novel Adoptive Transfer Approach," J. Clin. Invest. 94: 1076-1084 (1994).
Chambers, C.A., "The expanding world of co-stimulation: the two-signal model revisited,"TRENDS in Immunol., 2001, 22(4):217-223.
Champlin R. "T-cell depletion to prevent graft-versus-host disease after bone marrow transplantation," Hematol Oncol Clin North Am. Jun. 1990,4(3):687-98.
Chang, Y.H. et al., "A chimeric receptor with NKG2D specificity enhances natural killer cell activation and killing of tumor cells," Cancer Res, 73(6): 1777-1786 (2013).
Chao, D.T. et al., "BCL-2 family: regulators of cell death," Annu Rev 1mmunol., 16: 395-419 (1998).
Cheresh et al., "Disialogangliosides GD2 and GD3 Are Involved in the Attachment of Human Melanoma and Neuroblastoma Cells to Extracellular Matrix Proteins," J Cell Biol. 1986, 102(3):688-696.
Chertova, E. et al., "Characterization and favorable in vivo properties of heterodimeric soluble IL-l5.IL-15Ralpha cytokinc compared to IL-15 monomer,"J Biol Chem., 288(25): 18093-18103 (2013).
Cheung et al., "Anti-Idiotypic Antibody Facilitates scFv Chimeric Immune Receptor-Gene Transduction and Clonal Expansion of Human Lymphocytes for Tumor Therapy,"Hybridoma and Hybridomies, 2003, 24(4): 209-218.
Chiorean and Miller, "The biology of natural killer cells and implications for therapy of human disease," J Hematother Stem Cell Res, Aug. 2001, 10(4): 451-63.
Cho, D., and D. Campana, "Expansion and activation of natural killer cells for cancer immunotherapy," The Korean Journal of Laboratory Medicine, 29(2): 89-96 (2009).
Clarke et al., "Folding studies of immunoglobulin-like beta-sandwich proteins suggest that they share a common folding pathway," Structure, 7(9):1145-1153, Sep. 15, 1999.
ClinicalTrials.gov, "A Multi-Center Study Evaluating KTE-C19 in Pediatric and Adolescent Subjects With Relapsed/Refractory B-precursor Acute Lymphoblastic Leukemia (ZUMA-4)," available at https://clinicaltrials.gov/show/NCT02625480, NCT02625480 (Retrieved from the Internet on Jun. 21, 2016).
ClinicalTrials.gov, "A Phase 1-2 Multi-Center Study Evaluating KTE-C19 in Subjects With Refractory Aggressive Non-Hodgkin Lymphoma (ZUMA-1) (ZUMA-1)," available at https://clinicaltrials.gov/show/NCT02348216, NCT02348216 (Retrieved from the Internet on Jun. 21, 2016).
ClinicalTrials.gov, "A Phase 2 Multicenter Study Evaluating Subjects With Relapsed/Refractory Mantle Cell Lymphoma (ZUMA-2)," available at https://clinicaltrials.gov/show/NCT02601313, NCT02601313 (Retrieved from the Internet on Jun. 21, 2016).
ClinicalTrials.gov, "A Study Evaluating KTE-C19 in Adult Subjects With Relapsed/Refractory B-precursor Acute Lymphoblastie Leukemia (r/r ALL) (ZUMA-3) (ZUMA-3)," available at https://clinicaltrials.gov/show/NCT02614066, NCT02614066 (Retrieved from the Internet onJun. 21, 2016).
ClinicalTrials.gov, "Administration of Anti-CD19-ehimerie-antigen-receptor-transduced T Cells From the Original Transplant Donor to Patients With Recurrent or Persistent B-cell Malignancies After Allogeneie Stem Cell Transplantation," available at https://clinicaltrials.gov/show/NCT01087294, NCT01087294 (Retrieved from the Internet on Jun. 21, 2016).
ClinicalTrials.gov, "Anti-CD19 White Blood Cells for Children and Young Adults With B Cell Leukemia or Lymphoma," available at https://clinicaltrials.gov/show/NCT01593696, NCT01593696 (Retrieved from the Internet on Jun. 21, 2016).
ClinicalTrials.gov, "CAR T Cell Receptor Immunotherapy for Patients With B-cell Lymphoma," available at https://clinicaltrials.gov/show/NCT00924326, NCT00924326 (Retrieved from the Internet on Jun. 21, 2016).

(56) References Cited

OTHER PUBLICATIONS

ClinicalTrials.gov, "CD19 CAR T Cells for B Cell Malignancies After Allogeneic Transplant," available at https://clinicaltrials.gov/show/NCT01475058, NCT01475058 (Retrieved from the Internet on Jun. 21, 2016).
ClinicalTrials.gov, "CD19 Chimeric Receptor Expressing T Lymphocytes in B-Cell Non Hodgkin's Lymphoma, ALL & CLL (CRETI-NH)," available at https://clinicaltrials.gov/show/NCT00586391, NCT00586391 (Retrieved from the Internet on Jun. 21, 2016).
ClinicalTrials.gov, "CD 19+ CAR T Cells for Lymphoid Malignancies," available at https://clinicaltrials.gov/show/NCT02529813, NCT02529813 (Retrieved from the Internet on Jun. 21, 2016).
ClinicalTrials.gov, "Consolidation Therapy With Autologous T Cells Genetically Targeted to the B Cell Specific Antigen CD19 in Patients With Chronic Lymphocytic Leukemia Following Upfront Chemotherapy With Pentostatin, Cyclophosphamide and Rituxiniab," available at https://clinicaltrials.gov/show/NCT01416974, NCT01416974 (Retrieved from the Internet on Jun. 21, 2016).
ClinicalTrials.gov, "Genetically Engineered Lymphocyte Therapy in Treating Patients With B-Cell Leukemia or Lymphoma That is Resistant or Refractory to Chemotherapy," available at https://clinicaltrials.gov/show/NCT01029366, NCT01029366 (Retrieved from the Internet on Jun. 21, 2016).
ClinicalTrials.gov, "High Dose Therapy and Autologous Stem Cell Transplantation Followed by Infusion of Chimeric Antigen Receptor (CAR) Modified T-Cells Directed Against CD19+ B-Cells for Relapsed and Refractory Aggressive B Cell Non-Hodgkin Lymphoma," available at https://cliniealtrials.gov/show/NCT01840566, NCT01840566 (Retrieved from the Internet on Jun. 21, 2016).
ClinicalTrials.gov, "In Vitro Expanded Allogeneic Epstein-Barr Virus Specific Cytotoxic T-Lymphocytes (EBV-CTLs) Genetically Targeted to the CD19 Antigen in B-cell Malignancies," available at https://clinicaltrials.gov/show/NCT01430390, NCT01430390 (Retrieved from the Internet on Jun. 21, 2016).
ClinicalTrials.gov, "Precursor B Cell Acute Lymphoblastic Leukemia (B-ALL) Treated With Autologous T Cells Genetically Targeted to the B Cell Specific Antigen CD19," available at https://clinicaltrials.gov/show/NCT01044069, NCT01044069 (Retrieved from the Internet on Jun. 21, 2016).
ClinicalTrials.gov, "Study Evaluating the Efficacy and Safety of JCAR015 in Adult B-cell Acute Lymphoblastic Leukemia (B-ALL) (ROCKET)," available at https://clinicaltrials.gov/show/NCT02535364, NCT02535364 (Retrieved from the Internet on Jun. 21, 2016).
ClinicalTrials.gov, "T Cells Expressing a Fully-human AntiCD19 Chimeric Antigen Receptor for Treating B-cell Malignancies," available at https://clinicaltrials.gov/show/NCT02659943, NCT02659943(Retrieved from the Internet on Jun. 21, 2016).
ClinicalTrials.gov, "T-Lymphocytes Genetically Targeted to the B-Cell Specific Antigen CD19 in Pediatric and Young Adult Patients With Relapsed B-Cell Acute Lymphoblastic Leukemia," available at https://clinicaltrials.gov/show/NCT01860937, NCT01860937(Retrieved from the Internet on Jun. 21, 2016).
ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell Specific Antigen CD 19", Available at: https://clinicaltrials.gov/show/NCT00466531, NCT00466531(Retrieved from the Internet on Jun. 21, 2016).
Cochran et al., "Receptor clustering and transmembrane signaling in T cells," Trends Biochem Sci, 26(5):304-310, May 2001.
Collins et al., "Donor leukocyte infusions in 140 patients with relapsed malignancy after allogcneic bone marrow transplantation," J Clin Oncol, Feb. 1997, 15(2): 433-44.
Collins et al., "Donor leukocyte infusions in acute lymphocytic leukemia," Bone Marrow Transplantation, 2000, 26: 511-516.
Cooley, S. et al., "Donor selection for natural killer cell receptor genes leads to superior survival after unrelated transplantation for acute myelogenous leukemia," Blood, 116(14): 2411-2419 (2010).
Cooper, M.A. et al., "In vivo evidence for a dependence on interleukin 15 for survival of natural killer cells," *Blood*, 100(10): 3633-363 8 (2002).
Cooper et al., "T-Cell Clones can be Rendered Specific for CD 1 9: Toward the Selective Augmentation of the Graft-Versus-B Lineage Leukemia Effect," Blood, 2003, pp. 1637-1644, vol. 101.
Cruz et al., "Infusion of donor-derived CD19-redirected virus-specific T cells for B-cell malignancies relapsed after allogeneic stem cell transplant: a phase 1 study," Blood 122(17):2965-2973 (2013).
Curti, A. et al., "Successful transfer of alloreactive haploidentical KIR ligand-mismatched natural killer cells after infusion in elderly high risk acute myeloid leukemia patients," Blood, 118(12): 3273-3279 (2011).
Damle et al., "Differential regulatory signals delivered by antibody binding to the CD28 (Tp44) molecule during the activation of human T lymphocytes," J Immunol., 140(6):1753-1761, Mar. 15, 1988.
Darcy, P.K., et al., "Expression in cytotoxic T lymphocytes of a single-chain anti-carcinoembryonic antigen antibody. Redirected Fas ligand-mediated lysis of colon carcinoma," Eur. J. Immunol. 28: 1663-1672 (1998).
Davila, M.L., et al., "Efficacy and Toxicity Management of 19-28z CAR T Cell Therapy in B Cell Acute Lymphoblastic Leukemia," Science Translat. Med. 6(24) (2014).
DeBenedette et al., "Role of 4-1BB ligand in costimulation of T lymphocyte growth and its upregulation on M12 B lymphomas by cAMP," J Exp Med, Mar. 1995, 181(3): 985-92.
DeBenedette, MA, et al.. "Costimulation of CD28-T Lymphocytes by 4-1 BB Ligand," J. Immunol., 1997, pp. 551-559, vol. 158.
Delahaye, N.F. et al., "Altematively spliced NKp30 isoforms affect the prognosis of gastrointestinal stromal tumors," *Nat Med*., 17(6): 700-707 (2011).
Diefenbach et al., "Selective associations with signaling proteins determine stimulatory versus costimulatory activity of NKG2D," Nature Publishing Group, vol. 3, No. 12, pp. 1142-1149, (Dec. 2002).
Dotti et al., "Design and Development of Therapies using Chimeric Antigen Receptor-Expressing T cells," Immunol Rev., 257(1), 35 pages, Jan. 2014.
Doubrovian, et al., "Evasion from NK Cell Immunity by MHC Class I Chain-Related Molecules Expressing Colon Adenocarcinoma," Journal of Immunology, vol. 171, pp. 689-6899, (2003).
Dubois et al., "IL-15Rαrecycles and presents IL-15 in trans to neighboring cells," Immunity, Nov. 2002, 17(5): 537-47.
Dubois, S., et al., "Preassociation of IL-15 with IL-15R alpha-IgG1-Fc enhances its activity on proliferation of NK and CD8+ /CD44high T cells and its antitumor action," Journal of Immunology, 180(4):2099-2106 (2008).
Dudley, M.E., et al., "Adoptive Transfer of Cloned Melanoma-Reactive T Lymphocytes for the Treatment of Patients with Metastatic Melanoma," J. Immunother. 24: 363-3 73 (2001).
Ellis et al., "Interactions of CD80 and CD86 with CD28 and CTLA4," J Immunol., 156(8):2700-2709, Apr. 15, 1996.
Eshhar et al., "Specific activation and targeting of cytotoxic lymphocytes through chimeric single chains consisting of antibody-binding domains and the γ or ζ subunits of the immunoglobulin and T-cell receptors," Proc. Natl. Acad. Sci. USA, 1993, 90:720-724.
Eshhar, Z, et al . "Functional Expression of Chimeric Receptor Genes in Human T Cells," J. Immunol. Methods, 2001, 248(1-2):67-76.
Eshhar, Z., "Tumor-specific T-bodies: towards clinical application," Cancer Immunol. Immunother. 45: 131-136 (1997).
Fagan, E.A., and Eddleston, A.L.W.F., "Immunotherapy for cancer: the use of lymphokine activated killer (LAK) cells," Gut 28: 113-116 (1987).
Farag et al., "Natural killer cell receptors: new biology and insights into the Graft-versus-leukemia affect," Blood, 2002, 100(6): 1935-1947.
Fehniger TA, et al., "Ontogeny and expansion of human natural killer cells: clinical implications", Int Rev Immunol. Jun. 2001; 20(3-4):503-534.

(56) References Cited

OTHER PUBLICATIONS

Fehniger, T.A., et al., "Interleukin 15: biology and relevance to human disease," Blood, 97(1): 14-32 (2001).
Ferlazzo, G. et al., "Distinct roles of IL-12 and IL-15 in human natural killer cell activation by dendritic cells from secondary lymphoid organs," PNAS, 101(47): 16606-16611 (2004).
Femandez-Messina et al., "Human NKG2D-ligands: cell biology strategies ensure immune recognition," Frontiers in Immunology, vol. 3, Article 299, 9 Pages, (Sep. 2012).
Ferris, R.L. et al., "Tumor antigen-targeted, monoclonal antibody-based immunotherapy: clinical response, cellular immunity, and immunoescape," *J Clin Oncol*, 28(28): 4390-4399 (2010).
Finney et al., "Activation of resting human primary T cells With chimeric receptors: costimulation from CD28, inducible costimulator, CD134, and CD137 in series with signals from the TCR zeta chain", J Immunol. Jan. 1, 2004; 172(1):104-113.
Finney et al., "Chimeric receptors providing both primary and costimulatory signaling in T cells From a single gene product," J Immunol. Sep. 15, 1998;161(6):2791-2797.
Foon et al., "Clinical and immune responses in advanced melanoma patients immunized with an anti-idiotype antibody mimicking disialoganglioside GD2," J Clin Oncol, 18(2):376-384, Jan. 2000.
Freshney, Animal Cell Culture, Cancer Research Campaign, IRL Press, 1986, 248 pages [Table of Contents Only].
Fujisaki, H. et al., "Expansion of highly cytotoxic human natural killer cells for cancer cell therapy," Cancer Res, 69(9): 4010-4017 (2009).
Fujisaki, H. et al., "Replicative potential of human natural killer cells," Br J Haematol,145: 606-613 (2009).
Gardner, R., et al., "Acquisition of a CD19 negative myeloid phenotype allows immune escape of MLL-rearranged B-ALL from CD19 CAR-T cell therapy," Blood (forthcoming 2016).
Garrity et al., "The activating NKG2D receptor assembles in the membrane with two signaling dimers into a hexameric structure," PNAS, vol. 102, No. 21, pp. 7641-7646, May 24, 2005.
Geiger and Jyothi, "Development and application for receptor-modified T lymphocytes for adoptive immunotherapy," Transfus Med Rev, Jan. 2001, 15(1): 21-34.
Geiger et al., "Integrated src kinase and costimulatory activity enhances signal transduction through single-chain chimeric receptors in T lymphocytes", Blood. Oct. 15, 2001; 98(8):2364-2371.
GenBank Accession No. NM 007360 GI:315221123, *Homo sapiens* killer cell lectin like receptor K1 (KLRKl), mRNA, dated May 29, 2017, 4 pages.
GenBank Accession No. NM_000734 GI: 27886640, *Homo sapiens* CD8 antigen, alpha polypeptide (TiT3 complex) (CD3Z), transcript variant 2, mRNA, dated October 27, 2004, 6 pages.
GenBank Accession No. NM_001768 GI: 27886640, *Homo sapiens* CD8 antigen, alpha polypeptide (p32) (CD8A), transcript variant 1, mRNA, dated October 27, 2004, 5 pages.
GenBank Accession No. NM_011612 GI: 6755830, Mus musculus tumor necrosis factor receptor superfamily, member 9 (Tnfrsf9), mRNA, dated October 26, 2004, 8 pages.
Germain et al., "T-cell signaling: the importance of receptor clustering," Curr Biol, 7(10):R640-R644, Oct. 1, 1997.
Ghobadi, et al., "Updated Phase 1 Results from ZUMA-1: A Phase 1-2 Multicenter StudyEvaluating the Safety and Efficacy of KTE-C 19 (Anti-CD19 CAR T Cells) in Subjects With Refractory Aggressive Non-Hodgkin Lymphoma," Slides accompanying oral presentation at the American Association for Cancer Research Annual Meeting, New Orleans, Louisiana (2016).
Ghorashian, S., et al., "CD19 chimeric antigen receptor T cell therapy for haematological malignancies," Br. J. Haematol. 169:463-478 (2015).
Giebel, S. et al., "Survival advantage with KIR ligand incompatibility in hematopoietic stem cell transplantation from unrelated donors," *Blood*, 102(3): 814-819 (2003).
Gilfillan et al., "NKG2D recruits two distinct adapters to trigger NK cell activation and costimulation," Nature Publishing Group, Nature Immunology, vol. 3, No. 12, pp. 1150-1155, Dec. 2002.
Gill, S., et al., "Chimeric antigen receptor T cell therapy: 25 years in the making,"Blood Rev. (2015).
Ginaldi, L., et al., "Levels of expression of CD19 and CD20 in chronic B cell leukaemias," J. Clin. Pathol. 51: 364-369 (1998).
Giuliani, M. et al., "Generation of a novel regulatory NK cell subset from peripheral blood CD34+ progenitors promoted by membrane-bound IL-15," PLos One, 3(5): 02241 (2008).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, 1999, 1(2): 123-127.
Goodier and Londei, "CD28 is not directly involved in the response of human CD3-CD56+ natural killer cells to lipopolysaccharide: a role for T cells," Immunology, Apr. 2004, 111(4): 384-90.
Goodwin et al., "Molecular cloning of a ligand for the inducible T cell gene 4-1 BB: a member of an emerging family of cytokmes with homology to tumor necrosis factor", Eur J Immunol. Oct. 1993; 23( 10):2631-2641.
Greene et al., "Covalent dimerization of CD28/CTLA-4 and oligomerization of CD80/CD86 regulate T cell costimulatory interactions," J Biol Chem., 271(43):26762-26771, Oct. 25, 1996.
Greenfield, E.A., et al., "CD28/B7 Costimulation: A Review," Crit. Rev. Immunol. 18: 389-418 (1998).
Greenwald et al., "The B7 Family Revisted," Annu. Rev. Immunol., 2005, 23: 515-548.
Grillo-López, A., "Rituximab: An Insider's Historical Perspective," Seminars in Oncology 27(6 Suppl 12): 9-16 (2012).
Gross and Eshhar, "Endowing T cells with antibody specificity using chimeric T cell receptors," FASEB J. Dec. 1992;6(15):3370-3378.
Grupp ct al., "Chimeric antigen receptor-modified T cells for acute lymphoid leukemia," N Engl J Med. Apr. 18, 2013; 368 (16):1509-1518.
Handgretinger, R., et al., "A phase I study of neuroblastoma with the anti-ganglioside GD2 antibody 14.G2a," Cancer Immunol. Immunother. 35: 199-204 (1992).
Hara et al., "NKG2D gene polymorphisms are associated with disease control of chronic myeloid leukemia by dasatinib," Int. J. Hematol., 9 pages, Aug. 9, 2017.
Harada H, et al., "Selective expansion of human natural killer cells from peripheral blood mononuclear cells by the cell line, HFWT", Jpn J Cancer Res. Mar. 2002, 93(3):313-319.
Harada H, et al., "A Wilms tumor cell line, HFWT, can greatly stimulate proliferation of CD56+ human natural killer cells and their novel precursors in blood mononuclear cells", Exp Hematol. Jul. 2004; 32(7):614-621.
Harding et al., "CD28-mediated signalling co-stimulates murine T cells and prevents induction of anergy in T-cell clones," Nature, 356(6370):607-609, Apr. 16, 1992.
Harmon et al., "Dexamethasone induces irreversible G1 arrest and death of a human lymphoid cell line," J Cell Physiol, Feb. 1979, 98(2): 267-78
Haynes NM, et al., "Rejection of syngeneic colon carcinoma by CTLs expressing single-chain antibody receptors codelivering CD28 costimulation", J Immunol., Nov. 15, 2002; 169(10):5780-5786.
Haynes NM, et al., "Single-chain antigen recognition receptors that costimulate potent rejection of established experimental tumors", Blood, Nov. 1, 2002; 100(9):3155-3163.
Haynes, N.M., et al., "Redirecting Mouse CTL Against Colon Carcinoma: Superior Signaling Efficacy of Single-Chain Variable Domain Chimeras Containing TCR-ζ vs FcεRI-γ," J. Immunol. 166: 182-187 (2001).
Heuser, C., et al., "T-cell activation by recombinant immunoreceptors: Impact of the intracellular signalling domain on the stability of receptor expression and antigen-specific activation of grafted T cells," Gene Therapy 10: 1408-1419 (2003).
Hollyman, D., et al., "Manufacturing Validation of Biologically Functional T Cells Targeted to CD19 Antigen for Autologous Adoptive T cell Therapy," J. Immunother. 32: 169-180 (2009).
Hombach , et al., "Tumor-specific T cell activation by recombinant immunoreceptors: CD3 zeta signaling and CD28 costimulation are simultaneously required for efficient IL-2 secretion and can be

(56) References Cited

OTHER PUBLICATIONS integrated into one combined CD28/CD3 zeta signaling receptor molecule", J Immunol., Dec. 1, 2001; 167(11):6123-6131.
Hombach et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis," Cancer Res., 2001, 61: 1976-1982.
Hombach et al., "The recombinant T cell receptor strategy: insights into structure and function of recombinant immunoreceptors on the way towards an optimal receptor design for cellular immunotherapy," Curr Gene Ther. 2002 2(2):211-226.
Hombach, A., et al., "Adoptive immunotherapy with genetically engineered T cells: modification of the IgG1 Fc 'spacer' domain in the extracellular moiety of chimeric antigen receptors avoids 'off-target' activation and unintended initiation of an innate immune response," Gene Therapy 17: 1206-1213 (2010).
Hombach, A., et al., "T cell activation by recombinant FcεRI γ-chain immune receptors: an extracellular spacer domain impairs antigendependent T cell activation but not antigen recognition," Gene Therapy 7: 1067-1075 (2000).
Horng et al., "NKG2D signaling is coupled to the interleukin 15 receptor signaling pathway," Nature Immunology, vol. 8, No. 12, pp. 1345-1352, Dec. 2007.
Hsu, C. er al., "Cytokine-independent growth and clonal expansion of a primary human CD8+ T-cell Clone following retroviral transduction with the IL-15 gene," Blood, 109(12): 5168-5177 (2007).
Hsu, K.C. et al., "Improved outcome in HLA-identical sibling hematopoietic stem-cell transplantation for acute myelogenous leukemia predicted by KIR and HLA genotypes," Blood, 105(12): 4878-4884 (2005).
Hurtado et al., "Potential role of 4-1BB in T cell activation. Comparison with the costimulatory molecule CD28," J Immunol, Oct. 1995, 155(7): 3360-3367.
Imai C, et al., "Chimeric receptors with 4-1BB signaling capacity provoke potent cytotoxicity against acute lymphoblastic leukemia", Leukemia, Feb. 12, 204; 18(4):676-684.
Imai C, et al., "T-cell immunotherapy for B-lineage acute lymphoblastic leukemia using chimeric antigen receptors that deliver 4-1 BB-mediated costimulatory signals", Blood. Nov. 16, 2003; 102(11 ):66a-67a (Abstract #223).
Imai C et al. "Genetic modification of primary natural killer cells overcomes inhibitory signals and induces specific killing of leukemic cells," Blood. 2005;106:376-383.
Imai et al. "Genetic Modification of T cells for cancer therapy," Journal of Biological Regulators and Homeostatic Agents, 18 (1): p. 62-71; Jan. 2004.
Imai, C., et al; "A novel method for propagating primary natural killer (NK) cells allows highly Efficient expression of anti-CD19 chimeric receptors and generation of powerful cytotoxicity Against NK-resistent acute lymphoblastic leukemia cells." Abstract# 306 Blood 104 (Nov. 16, 2004).
Imamura, M. et al., "Autonomous growth and increased cytotoxicity of natural killer cells expressing membrane-bound interleukin-15," *Blood*, 124(7): 1081-1088 (Jul. 8, 2014).
Inaguma et al., "Expression of neural cell adhesion molecule L1 (CD171) in neuroectodermal and other tumors. An immunohistochemical study of 5155 tumors and critical evaluation of CD171 prognostic value in gastrointestinal stromal tumors," Oncotarge., 7(34):55276-55289, Jul. 11, 2016.
Ishii, H. et al., "Monocytes enhance cell proliferation and LMP1 expression of nasal natural killer/T-cell lymphoma cells by cell contact-dependent interaction through membrane-bound IL- 15," International Journal of Cancer, 130: 48-58 (2012).
Ishiwata I, et al., "Carcinoembryonic proteins produced by Wilms' tumor cells in vitro and in vivo", Exp Pathol. 1991; 41(1):1-9.
Israeli, R.S., et al., "Expression of the Prostate-specific Membrane Antigen," Cancer Res, 1994, 54:1807-1811.
Ito et al., "Hyperdiploid acute lymphoblastic leukemia with 51 to 65 chromosomes: a distinct biological entity with a marked propensity to undergo apoptosis," Blood, Jan. 1999, 93(1): 315-20.
Jena et al., "Redirecting T-cell specificity by introducing a tumor-specific chimeric antigen receptor," Blood, 2010, 116(7):1035-1044
Jenkins et al., "Inhibition of antigen-specific proliferation of type 1 murine T cell clones after stimulation with immobilized anti-CD3 monoclonal antibody," J Immunol, 144(1):16-22, Jan. 1, 1990.
Jensen, M., et al., "CD20 is a molecular target for scFVFc:ζ receptor redirected T cells: implications for cellular immunotherapy of CD20+ malignancy," Biol. Blood and Marrow Transplantation 4: 75- 83 (1998).
Jensen, M.C., et al., "Anti-transgene Rejection Responses Contribute to Attenuated Persistence of Adoptively Transferred CD20/CD19- Specific Chimeric Antigen Receptor Redirected T Cells in Humans," Biol. Blood Marrow Transplant 16: 1245-1256 (2010).
Jiang et al., "Functional characterization of interleukin-15 gene transduction into the human natural killer cell line N KL," Cytother. 10(3):265-274, 2008.
Jiang, W. et al., "hIL-15 gene-modified human natural killer cells (NKL-IL15) augments the anti-human hepatocellular carcinoma effect in Vivo," Immunobiology, 219: 547-553 (Mar. 12, 2014).
Johnson and Jenkins, "The role of anergy in peripheral T cell unresponsiveness," Life Sci, 1994, 55(23): 1767-1780.
June et al., "The B7 and CD28 receptor families," Immunol Today, Jul. 1994, 15(7): 321-31.
Kabalak et al., "Association of an NKG2D gene variant with systemic lupus erythematosus in two populations," Human Immunology, vol. 71, pp. 74-78, 2010.
Kalos et al, "T Cells with Chimeric Antigen Receptors Have Potent Antitumor Effects and Can Establish Memory in Patients with Advanced Leukemia," Sci Transl Med. Aug. 10, 2011;3(95):95ra73.
Kariv, I., et al., "Analysis of the Site of Interaction of CD28 with Its Counter-Receptors CD80 and CD86 and Correlation with Function," J. of Immunol. 157: 29-38 (1996).
Kershaw, M.H., et al., "A Phase I Study on Adoptive Immunotherapy Using Gene-Modified T Cells for Ovarian Cancer," Clin. Cancer Res. 12:6106-6115 (2006).
Khammari, A., et al., "Long-term follow-up of patients treated by adoptive transfer of melanoma tumor-infiltrating lymphocytes as adjuvant therapy for stage III melanoma," Cancer Immunol. Immunother. 56: 1853-1860 (2007).
Kim Y J, et al., "Human 4-1 BB regulates CD28 co-stimulation to promote Th1 cell responses. Eur J. Immunol", Mar. 1998; 28(3):881-890.
Kim Y J, et al., "Novel T cell antigen 4-1 BB associates with the protein tyrosine kinase p561ck1", J lmmunol.Aug. 1, 1993; 151(3):1255-1262.
Kitaya, K. et al., "IL-15 expression at human endometrium and decidua," Biology of Reproduction, 63(3): 683-687 (2000).
Kitaya, K., et al., "Regulatory role of membrane-bound form interleukin-15 on human uterine microvascular endothelial cells in circulating CD16(-) natural killer cell extravasation into human endometrium," Biology of Reproduction, 89(3): 70 (2013).
Klein E, et al., "Properties of the K562 cell line, derived from a patient with chronic myeloid leukemia", Int J Cancer. Oct. 15, 1996; 18(4 ):421-431.
Klingemann HG, et al., "Ex vivo expansion of natural killer cells for clinical applications", Cytotherapy. 2004, 6(1 ):15-22.
Kobayashi et al., "Role of trans-cellular IL-1S presentation in the activation of NK cell-mediated killing, which leads to enhanced tumor immunosurveillance," Blood, Jan. 2005, 105(2): 721-727.
Kochenderfer, J.N. et al. "Construction and Pre-clinical Evaluation of an Anti-CD19 Chimeric Antigen Receptor," J. Immunother. 32(7):689-702 (2009).
Kochenderfer, J.N., et al. "Chemotherapy-Refractory Diffuse Large B-Cell Lymphoma and Indolent B-Cell Malignancies Can be Effectively Treated With Autologous T Cells Expressing an Anti-CD19 Chimeric Antigen Receptor," J. Clin. Oncol. 33:540-549 (2014).
Kochenderfer, J.N., et al. "Donor-derived CD19-targeted T cells cause regression of malignancy persisting after allogeneic hematopoietic stem cell transplantation," Blood 122(25): 4129-4139 (2013).
Kochenderfer, J .N., et al., "B-cell depletion and remissions of malignancy along With cytokine-associated toxicity in a clinical trial of anti-CD19 chimeric-antigen-receptor-transduced T cells," Blood 119(12):2709-2720 (2012).

(56) References Cited

OTHER PUBLICATIONS

Kochenderfer, J.N., et al., "Eradication of B-lineage cells and regression of lymphoma in a patient treated With autologous T cells genetically-engineered to recognize CD19," Blood 116(20):4099-4102 (2010).
Koeffler and Golde, "Acute myelogenous leukemia: a human cell line responsive to colony-stimulating activity," Science, Jun. 1978, 200(4337): 1153-1154.
Koehler et al. "Engineered T Cells for the Adoptive Therapy of B-Cell Chronic Lymphocytic Leukaemia," Advances in Hematology, vol. 2012, Article ID 595060, 13 pages; doi:10.1155/2012/595060 (2012).
Kohn et al., "CARS on track in the clinic," Mol Ther. Mar. 2011; 19(3):432-438.
Koka, R. et al., "Cutting edge: murine dendritic cells require IL-15R alpha to prime NK cells," *J Immunol.*, 173(6): 3594-3598 (2004).
Kolb HJ, et al., "Graft-Versus-Leukemia Effect of Donor Lymphocyte Transfusions in Marrow Grafted Patients," Blood, 1995, 86(5):2041-2050.
Kowolik, C.M., "CD28 Costimulation Provided through a CD19-Specific Chimeric Antigen Receptor Enhances In vivo Persistence and Antitumor Efficacy of Adoptively Transferred T Cells," Cancer Research 66(22): 10995-11004 (2006).
Krampera et al., "Bone marrow mesenchymal stem cells inhibit the respnose of naïve and memory antigen-specific T cells to their cognate peptide," Blood, May 2003, 101(9): 3722-9.
Krause et al., "Antigen-dependent CD28 Signaling Selectively Enhances Survival and Proliferation in Genetically Modified Activated Human Primary T Lymphocytes," J. Exp. Med., 1998, 188(4):619-626.
Krug, C., et al., "Stability and activity of MCSP-specific chimeric antigen receptors (CARs) depend on the scFv antigen-binding domain and the protein backbone," Cancer Immunol. Immunother. 64:1623-1635 (2015).
Kuo et al., "Efficient gene transfer into primary murine lymphocytes obviating the need for drug selection," Blood, Aug. 1993, 82(3): 845-52.
Kurokawa, M. and S. Kornbluth, "Caspases and kinases in a death grip," *Cell*, 138(5): 83 8-854 (2009).
Kwon BS, et al., "cDNA sequences of two inducible T-cell genes", Proc Natl Acad Sci U SA. Mar. 1989; 86(6):1963-1967.
Lafrenierc, R. and Rosenberg, S.A., "Successful Immunotherapy of Murine Experimental Hepatic Metastases with Lymphokine-activated Killer Cells and Recombinant Interleukin 2," Cancer Res. 45: 3735-3741 (1985).
Lamers, C.H.J., et al., "Treatment of Metastatic Renal Cell Carcinoma With Autologous T-Lymphocytes Genetically Retargeted Against Carbonic Anhydrase IX: First Clinical Experience," J. Clin. Oncol. 24: e20-e22 (2006).
Lang et al., "Absence of B7.1-CD28/CTLA-4-mediated co-stimulation in human NK cells," Eur. J. Immunol, Mar. 1998, 28: 780-786.
Langer et al., "Comparative Evaluation of Peripheral Blood T Cells and Resultant Engineered Anti-CD19 CAR T-Cell Products From Patients With Relapsed/Refractory Non-Hodgkin Lymphoma (NHL)," Abstract 2305, Proceedings: AACR 107th Annual Meeting 2016; Apr. 16-20, 2016, New Orleans, Louisiana.
Lanzavecchia et al., "Antigen decoding by T lymphocytes: from synapses to fate determination," Nat Immunol., 2(6):487-492, Jun. 2001.
Lapteva, N. et al., "Large-scale ex vivo expansion and characterization of natural killer cells for clinical applications," *Cytotherapy*, 14(9): 1131-1143 (2012).
Le Blanc et al., "Mesenchymal stem cells inhibit and stimulate mixed lymphocyte cultures and mitogenic responses independently of the major histocompatability complex," Scand J Immunol, Jan. 2003, 57(1): 11-20.
Lee, D.W., et al., "T cells expressing CD19 chimeric antigen receptors for acute lymphoblastic leukaemia in children and young adults: a phase 1 dose-escalation trial," Lancet 385:517-528 (2015).
Lehner et al., "Redirecting T Cells to Ewing's Sarcoma Family of Tumors by a Chimeric NKG2D Receptor Expressed by Lentiviral Transduction of MRNA Transfection," PLoS One, vol. 7, Issue 2, Feb. 2012.
Leung, W. et al., "Determinants of antileukemia effects of allogeneic NK cells," J Immunol, 172(1): 644-650 (2004).
Li et al., "Costimulation by CD48 and B7-1 induces immunity against poorly immunogenic tumors," J Exp Med, Feb. 1996, 183(2): 639-44.
Li et al., "Polarization Effects of 4-1BB during CD28 Costimulation in Generating Tumor-reactive T Cells for Cancer Immunotherapy," Cancer Research vol. 63, pp. 2546-2552, May 15, 2003.
Liao, W. et al., "Interleukin-2 at the crossroads of effector responses, tolerance, and immunotherapy," Immunity, 38(1): 13-25 (2013).
Liebowitz et al., "Costimulatory approaches to adoptive immunotherapy," Curr Opin Oncol, Nov. 1998, 10(6): 533-41.
Linsley and Ledbetter, "The role of CD28 receptor during T cell responses to antigen," Annu Rev Immunol, 1993, 191-212.
Liu, H., et al., "Monoclonal Antibodies to the Extracellular Domain of Prostate-specific Membrane Antigen Also React with Tumor Vascular Endothelium," Cancer Res. 57: 3629-3634 (1997).
Liu, L, et al. "Novel CD4-Based Bispecific Chimeric Antigen Receptor Designed for Enhanced Anti-HIV Potency and Absence of HIV Entry Receptor Activity," J. Virol. 89(13):6685-6694 (2015).
Lozzio et al., "Properties and Usefulness of the Original K-562 Human Myelogenous Leukemia Cell Line," Leukemia Research, vol. 3, No. 6, pp. 363-370, 1979.
Lode et al., "Targeted cytokines for cancer immunotherapy," Immunol Res., 21(2-3):279-288, 2000.
López-Requena et al., "Gangliosides, Ab1 and Ab2 antibodies III. The idiotype of anti-ganglioside mAb P3 is immtmogenic in a T cell-dependent manner," Mol Immunol, 2007, 44(11):2915-2922.
López-Requena et al., "Gangliosides, Ab1 and Ab2 antibodies IV, Dominance of VH domain in the induction of anti-idiotypic antibodies by Jene gun immunization," Mol Immunol. Apr. 2007;44(11):3070-3075. Epub Mar. 2, 2007.
Lozzio CB, et al., "Human chronic myelogenous leukemia cell-line with positive Philadelphia chromosome", Blood. Mar. 1975; 45(3):321-334.
Lugli, E. et al., "Transient and persistent effects of IL-15 on lymphocyte homeostasis in nonhuman primates," Blood, 116(17): 3238-3248 (2010).
Ma et al., "Chapter 15: Genetically engineered T cells as adoptive immunotherapy of cancer," Cancer Chemotherapy and Biological Response Modifiers Annual 20, Ch. 15, pp. 315-341, Giaccone et al. (Eds), Elsevier, 2002.
Maher J., et al., "Human T-lymphocyte cytotoxicity and proliferation directed by a single chimeric TCRzeta /CD28 receptor", Nat Biotechnol. Jan. 2002; 20(1):70-75.
Maloney, D.G., "Newer Treatments for Non-Hodgkin's Lymphoma: Monoclonal Antibodies," Oncology 12(10): 63-76 (1998).
Manabe et al., "Interleukin-4 induces programmed cell death (apoptosis) in cases of high-risk acute lymphoblastic leukemia," Blood, Apr. 1994, 83(7): 1731-7.
Mann et al., "Construction of a retrovirus packaging mutant and its use to produce helper-free defective retrovirus," Cell, May 1983, 33(1): 153-159.
Manzke et al., "Immunotherapeutic strategies in neuroblastoma: antitumoral activity of deglycosylated Ricin A conjugated anti-GD2 antibodies and anti-CD3xanti-GD2 bispecific antibodies," Med Pediatr Oncol., 36(1):185-189, Jan. 2001.
Manzke et al., "Locoregional treatment of low-grade B-cell lymphoma with CD3xCD19 bispecific antibodies and CD28 costimulation. I. Clinical phase I evaluation," Int J Cancer, 91(4):508-515, Feb. 15, 2001.
Manzke et al., "Locoregional treatment of low-grade B-cell lymphoma with CD3XCD19 bispecific antibodies and CD28 costimulation. II. Assessment of cellular immune responses," Int J Cancer., 91(4):516-522, Feb. 15, 2001.
Marincola, F.M., et al., "Escape of Human Solid Tumors from T-Cell Recognition: Molecular Mechanisms and Functional Significance," Adv. Immunol. 74: 181-273 (2000).

(56) References Cited

OTHER PUBLICATIONS

Markowitz et al., "A safe packaging line for gene transfer: separating viral genes on two different plasmids," J Virol, Apr. 1988, 62(4): 1120-4.
Marktel et al., "Immunologic potential of donor lymphocytes expressing a suicide gene for early immune reconstitution after hematopoietic T-cell-depleted stem cell transplantation," Blood, Feb. 2003, 101(4): 1290-8.
Martinet O., et al., T cell activation with systemic agonistie antibody versus local 4-1 BB ligand gene delivery combined with interleukin-12 eradicate liver metastases of breast cancer, Gene Ther. Jun. 2002; 9(12):786-792.
Martinez, E., et al., "Cutting Edge: NKGZD-Dependent Cytotoxicity Is Controlled by Ligand Distribution in the Target Cell Membrane", The Journal of Immunology, 2011, 186:5538-5542.
Maude et al., "Chimeric antigen receptor T cells for sustained remissions in leukemia," N Engl J Med., 371(16):1507-1517, Oct. 16, 2014.
Maus MV, et al., "Ex vivo expansion of polyclonal and antigen-specific cytotoxic T lymphocytes by artificial APCs expressing ligands for the T-cell receptor, CD28 and 4-1BB", Nat Biotechnol. Feb. 2002; 20(2): 143-148.
May KF, JR, et al., "Anti-4-1 BB monoclonal antibody enhances rejection of large tumor burden by promoting survival but not clonal expansion of tumor-specific CDS+ T cells," Cancer Res. 2002, 62(12):3459-3465.
McLaughlin et al., "Adoptive T-cell therapies for refractory/relapsed leukemia and lymphoma: current strategies and recent advances," Ther Adv Hematol., 6(6):295-307, Dec. 2015.
Melero, I. et al., "Monoclonal antibodies against the 4-1BB T-cell activation molecule eradicate established tumors," Nature Med., 1997, 3:682-685.
Melero I, et al., "Amplification of tumor immunity by gene transfer of the co-stimulatory 4-1 BB ligand: synergy With the CD2S co-stimulatory pathway," Eur J Immunol., 1998, 28(3): 1116-1121.
Melero I, et al., "NK1.1 cells express 4-1BB (CDW137) costimulatory molecule and are required for tumor immunity elicited by anti-4-1 BB monoclonal antibodies," Cell Immunol., 1998, 190(2): 167-172.
Mihara et al., "Development and functional characterization of human bone marrow mesencymal cells immortalized by enforced expression of telomerase," Br J Haematol, Mar. 2003, 120(5): 846-9.
Miller et al., "Rose of monocytes in the expansion of huma activated natural killer cells," Blood, Nov. 1992, 80(9): 2221-9.
Miller et al., "Sucessful adoptive transfer and in vivo expansion of human haploidential NK cells in patients With cancer," Blood, Apr. 2005, 105(8): 3051-7.
Miller, J.S., "Therapeutic applications: natural killer cells in the clinic," *Hematology Am Soc Hematol Educ Program* 2013: 247-253 (2013).
Milone MC, et al., "Chimeric receptors containing CD137 signal transduction domains mediate enhanced survival of T cells and increased anti leukemic efficacy in vivo", Mol Ther. Apr. 21, 2009; 17(8):1453-1464.
Mishra, A. et al., "Aberrant overexpression of IL-15 initiates large granular lymphocyte leukemia through chromosomal instability and DNA hypermethylation," *Cancer Cell*, 22(5): 645-655 (2012).
Mogi et al., "Tumour rejection by gene transfer of 4-1BB ligand and into a CD80(+) murine squamous cell carcinoma and the requirements of co-stimulatory molecules on tumour and host cells," Immunology, Dec. 2000, 101(4): 541-7.
Mondino and Jenkins, "Surface proteins involved in T cell costimulation," J Leukoc Biol, Jun. 1994, 55(6): 805-15.
Mora, "Dinutuximab for the treatment of pediatric patients with high-risk neuroblastoma," Expert Rev Clin Pharmacol., 9(5):647-653, Epub Mar. 21, 2016.
Morandi, B. et al., "NK cells provide helper signal for CD8+ T cells by inducing the expression of membrane-bound IL-15 on DCs," International Immunology, 21(5): 599-606 (2009).
Moretta L, et al., "Unravelling natural killer cell function: triggering and inhibitory human NK receptors," EMBO J., 2004, 23(2):255-259.
Moritz and Groner, "A spacer region between the single chain antibody- and the CD3 ζ-chain domain of chimeric T cell receptor components is required for efficient ligand binding and signaling activity," Gene Ther. Oct. 1995; 2(8):539-546.
Moritz, D., et al., "Cytotoxic T lymphocytes with a grafted recognition specificity for ERBB2-expressing tumor cells," Proc. Natl. Acad. Sci. USA 91:4318-4322 (1994).
Mortier, E., et al., "IL-15Ralpha chaperones IL-15 to stable dendritic cell membrane complexes that activate NK cells via trans presentation," *The Journal of Experimental Medicine*, 205(5): 1213-1225 (2008).
Musso, T. er a1., "Human monocytcs constitutivcly cxprcss membrane-bound, biologically active, and interferon-gamma-upregulated interleukin-15," *Blood*, 93(10): 3531-3539 (1999).
Nadler et al., "B4, a human B lymphocyte-associated antigen expressed on normal, mitogen-activated, and malignant B lymphocytes," J Immunol, Jul. 1983, 131(1): 244-50.
Nagashima et al., "Stable transduction of the interleukin-2 gene into human natural killer cell lines and their phenotypic and functional characterization in vitro and in vivo." Blood, May 1998, 91(10): 3850-61.
Nakamura et al., "Chimeric anti-ganglioside GM2 antibody with antitumor activity," Res. Mar. 15, 1994; 54(6):1511-6.
Naume et al., "A comparative study of IL-12 (cytotoxic lymphocyte maturation factor)-, IL-2-, and IL-7-induced effects on immunomagnetically purified CD56+ NK cells," J Immunol, Apr. 1992, 148(8): 2429-36.
Neepalu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Scoiety of Hematology Annual Meeting, Orlando, Florida (Dec. 5-8, 2015).
Negrini, S. et al., "Membrane-bound IL-15 stimulation of peripheral blood natural killer progenitors leads to the generation of an adherent subset co-expressing dendritic cells and natural killer functional markers," *Haematologica*. 96(5): 762-766 (2011).
Nicholson et al., "Construction and characterisation of a functional CD19 specific single chain Fv fragment for immunotherapy of B lineage leukaemia and lymphoma," Mol Immunol., 34(16-17):1157-1165, Nov.-Dec. 1997.
Nishigaki et al., "Prevalence and growth characteristics of malignant stem cells in B-lineage acute lymphoblastic leukemia," Blood, May 1997, 89(10): 3735-44.
Nunès et al., "The role of p21ras in CD28 signal transduction: triggering of CD28 With antibodies, but not the ligand B7-1, activates p21ras," J Exp Med, 180(3): 1067-1076, Sep. 1, 1994.
Oelke, M. et al., "Ex vivo induction and expansion of antigen-specific cytotoxic T cells by HLA-Ig-coated artificial antigen-presenting cells," Nat Med., 2003, 9(5):619-624.
Olsen, S.K. et al., "Crystal structure of the interleukin-15 interleukin-15 receptor a complex Insights into trans and cis presentation," The Journal of Biological Chemistry, 282(51): 37191-37204 (2007).
Ozkaynak, M.F. et al., "Phase I Study of Chimeric Human/Murine Anti-Ganglioside GD2 Monoclonal Antibody (ch14.18) With Granulocyte-Macrophage Colony-Stimulating Factor in Children With Nueroblastoma Immediately After Hematopoietic Stem-Cell Transplantation: A Children's Cancer Group Study," J. Clinical Oncol. 18: 4077-4085 (2000).
Pan et al., "Regulation of dendritic cell function by NK cells: mechanisms underlying the synergism in the combination therapy of IL-12 and 4-1BB activation," J Immunol, Apr. 2004, 172(8): 4779-4789.
Park, J.H., and Brentjens, R.J., "Are All Chimeric Antigen Receptors Created Equal?" J. Clin. Oncol. 33: 651-653 (2015).
Park, J.H. et al., "CD19-Targeted 19-28z CAR Modified Autologous T Cells Induce High Rates of Complete Remission and Durable Responses in Adult Patients with Relapsed, Refractory B-Cell ALL," Abstract presented at the American Society of Hematology

(56) References Cited

OTHER PUBLICATIONS

Annual Meeting, San Francisco, California, available at https://ash.confex.com/ash/2014/webprogram/Paper76573.htrnl (Dec. 6-9, 2014).
Park, J.H., et al., Abstract, "682 Implications of Minimal Residual Disease Negative Complete Remission (MRD-CR) and Allogeneic Stem Cell Transplant on Safety and Clinical Outcome of CD19-Targeted 19-28z CAR Modified T cells in Adult Patients with Relapsed, Refractory B-Cell ALL," Am. Soc'y Hematol., available at https://ash.confex.com/ash/2015/Webprogram/Paper86688.html (Dec. 5-8, 2015).
Park, Y.P., et al., "Complex Regulation of Human NKG2D-DAP10 Cell Surface Expression: Opposing Roles of the γc Cytokines and TGF-β1", Blood, Sep. 15, 2011, vol. 118, No. 11, pp. 3019-3027.
Parkhurst, M.R. et al., "Adoptive transfer of autologous natural killer cells leads to high levels of circulating natural killer cells but does not mediate tumor regression," Clin Cancer Res., 17(19): 6287-97 (2011).
Patel, S.D., et al., "Impact of chimeric immune receptor extracellular protein domains on T cell function," Gene Therapy 6: 412-419 (1999).
Paul, W.E., Fundamental Immunology, Third Edition, Chs. 1, 13 and 32 (pp. 1-20, 467-504, and 1143-1178), Raven Press, New York (1993).
Peach, R.J., et al., "Complementarity Determining Region 1 (CDR1)- and CDR3-analogous Regions in CTLA-4 and CD28 Determine the Binding to B7-1," J. Exp. Med. 180: 2049-2058 (1994).
Perussia et al., "Preferential proliferation of natural killer cells among peripheral blood mononuclear cells cocultured with B lymphoblastoid cell lines," Nat Immun Cell Growth Regul, 1987, 6(4): 171-88.
Pollok et al., "Regulation of 4-1BB expression by cell-cell interactions and the cytokines, interleukin-2 and interleukin-4," Eur J Immunol, Feb. 1995, 25(2): 488-94.
Pollok KE, et al., "Inducible T cell antigen 4-1 BB Analysis of expression and function," J Immunol., 1993, 150(3):771-781.
Porter and Antin, "The graft-versus-leukemia of allogeneic cell therapy," Annu Rev Med, 1999, 50: 369-86.
Porter DL et al., "Chimeric Antigen Receptor-Modified T Cells in Chronic Lymphoid Leukemia", N. Eng. J. Med. Aug. 25, 2011; 365(8):725-733.
Porter et al., "Induction of graft-versus-host disease as immunotherapy for relapsed chronic mycloid leukemia," N Engl J Med, Jan. 1994, 330(2): 100-6.
Pui et al., "Childhood acute lymphoblastic leukaemia—current status and future perspectives," Lancet Oncol, Oct. 2001, 2(10): 597-607.
Pule et al. "Virus-specific T cells engineered to coexpress tumor-specific receptors: persistence and antitumor activity in individuals with neuroblastoma," Nature Med., 2008, 14(11):1264-1270.
Qian, L. et al., "Construction of a plasmid for co-expression of mouse membrane-bound form of IL-15 and RAE-1ϵ and its biological activity," *Plasmid*, 65(3): 239-245 (2011).
Rajagopalan et al., Found: a cellular activating ligand for N Kp44, Blood, 122(17):2921-2922, Oct. 2013.
Ramos, C.A., et al., "CD19-CAR Trials," The Cancer J. 20: 112-118 (2014).
Ramos and Dotti, "Chimeric antigen receptor (CAR)-engineered lymphocytes for cancer therapy," Expert Opin Biol Ther., 2011, 11(7):855-873.
Riddell, S.R., et al., "T-Cell Therapy of Leukemia," Cancer Control 9: 114-122 (2002).
Riley et al., "The CD28 family: a T-cell rheostat for therapeutic control of T-ccll activation," Blood, 2005, 105213-21.
Roberts et al., "Antigen-specific cytolysis by neutrophils and NK cells expressing chimeric immune receptors bearing zeta or gamma signaling domains," J Immunol, Jul. 1998, 161(1): 375-84.
Robertson MJ, et al., "Costimulation of human natural killer cell proliferation: role of accessory cytokines and cell contact-dependent signals", Nat Immun. 1996-1997; 15(5):213-226.
Rooney et al., "Use of gene-modified virus-specific T lymphocytes to control Epstein-Barr-virus-related lymphoproliferation," Lancet, Jan. 1995, 345(8941): 9-13.
Rosenberg et al, "Special Report: Use of tumor-infiltrating lymphocytes and interleukin-2 in the immunotherapy of patients with metastatic melanoma," N. Engl. J. Med, 1988, 319:1676-1680.
Rosenberg, S.A., and Dudley, M.E., "Adoptive cell therapy for the treatment of patients with metastatic melanoma," Curr. Opin. Immunol. 21: 233-240 (2009).
Rosenfeld et al., "Phenotypic characterization of a unique non-T, non-B acute lymphoblastic leukaemia cell line," Nature, Jun. 1977, 267(5614): 843-3.
Rosenstein, M. et al., "Extravasation of intravascular fluid mediated by the systemic administration of recombinant interleukin 2," *J Immunol*, 137(5): 1735-1742 (1986).
Ross et al., "Classification of pediatric acute lymphoblastic leukemia by gene expression profiling," Blood, Oct. 2003, 102(8): 2951-9.
Rossi, J.M., et al., "Phase 1 Biomarker Analysis of ZUMA-1 (KTEC19-101) Study: A Phase 1-2 Multi-Center Study Evaluating the Safety and Efficacy of Anti-CD19 CAR T cells (KTE-}C19) in Subjects with Refractory Aggressive Non-Hodgkin Lymphoma (NHL)," Abstracted presented at the American Society of Hematology Annual Meeting, Orlando, Florida, available at https://ash.confex.com/ash/2015/Webprogram/Paper80339.html. (Dec. 5-8, 2015).
Rossig C, et al., "Epstein-Barr virus-specific human T lymphocytes expressing antitumor chimeric T-cell receptors: potential for improved immunotherapy," Blood, 2002, 99:2009-2016.
Rossig et al., "Targeting of G(D2)-positive tumor cells by human T lymphocytes engineered to express chimeric T-cell receptor genes," Int J Cancer, Oct. 2001, 94(2): 228-36.
Rowley, J. et al., "Expression of IL-15RA or an IL-15/IL-15RA fusion on CD8+ T cells modifies adoptively transferred T-cell function in cis," *European Journal of Immunology*, 39.: 491-506 (2009).
Rubnitz, J.E. et al., "NKAML: a pilot study to determine the safety and feasibility of haploidentical natural killer cell transplantation in childhood acute myeloid leukemia," J Clin Oncol, 28(6): 955-959 (2010).
Ruggeri, L. et al., "Effectiveness of donor natural killer cell alloreaetivity in mismatched hematopoietic transplants," Science, 295(5562): 2097-2100 (2002).
Sadelain et al., "The promise and potential pitfalls of chimeric antigen receptors," Curr Opin Immunol, 2009, 21(2):215-223.
Sadelatn et al., "Targeting tumours With genetically enhanced T lymphocytes," Nat Rev Cancer. Jan. 2003;3(1):35-45.
Sadelain, M., "CAR Therapy: the CD19 Paradigm," J. Clin. Investigation 125: 3392-3400 (2015).
Sahm et al., "Expression of IL-15 in N K cells results in rapid enrichm" Cancer lmmunol. lmmunother., 61 (9): 1451-1461, Feb. 2012.
Salih, H.R., et al., "Cutting Edge: Down-Regulation of MICA on Human Tumors by Proteolytic Shedding", The Journal of Immunology, 2002, 169:4098-4102.
Salomon and Bluestone, "Complexities of CD28/B7: CTLA-4 costimulatory pathways in autoimmunity and transplantation," Annu Rev Immunol, 2001, 19: 225-52.
Sambrook et al, "Molecular Cloning: A Laboratory Manual," (1989) [Table of Contents and Preface Only].
Sankhla, S.K., et al., "Adoptive immunotherapy using lymphokineactivated killer (LAK) cells and interleukin-2 for recurrent malignant primary brain tumors," J Neurooncol. 27: 133-140 (1995).
Savoldo, B., et al., "CD28 costimulation improves expansion and persistence of chimeric antigen receptor modified T cells in lymphoma patients," J. Clin. Invest. 121(5):1822-1826 (2011).
Schmaltz et al., "T cells require TRAIL for optimal graft-versus-tumor activity," Nat Med, Dec. 2002, 8(12): 1433-7.
Schneider et al., "Characterization of EBV-genome negative "null" and "T" cell lines derived from children with acute lymphoblastic leukemia and leukemic transformed non-Hodgkin lymphoma," Int J Cancer, May 1977, 19(5): 621-6.

(56) References Cited

OTHER PUBLICATIONS

Schroers et al., "Gene transfer into human T lymphocytes and natural killer cells by Ad5/F35 chimeric adenoviral vectors," Exp Hematol, Jun. 2004, 32(6): 536-46.
Schulz, G., et al., "Detection of Ganglioside GD2 in Tumor Tissues and Sera of Neuroblastoma Patients," Cancer Research 44: 5914-5920 (1984).
Schumacher, "T-cell-receptor gene therapy," Nat Rev Immunol, Jul. 2002, 2(7): 512-9.
Schwartz et al., "Structural basis for co-stimulation by the human CTLA-4/B7-2 complex," Nature, 410(6828):604-608, Mar. 29, 2001.
Schwarz et al., "ILA, the human 4-1BB homologue, is inducible in lymphoid and other cell lineages," Blood, Feb. 1995, 85(4): 1043-52.
Scott, A.M. et al., "Antibody therapy of cancer," *Nat Rev Cancer*, 12(4): 278-287 (2012).
Sentman, C.L., et al., "NK Cell Receptors as Tools in Cancer Immunotherapy", Advances in Cancer Research, 2006, pp. 249-292.
Sentman, C.L., et al., "NKG2D CARS as Cell Therapy for Cancer", The Cancer Journal, vol. 20, No. 2, Mar./Apr. 2014, pp. 156-159.
Sheard, MA. et al., "Membrane-bound TRAIL supplements natural killer cell cytotoxicity against neuroblastoma cells," Journal of Immunotherapy, 36(5): 319-329 (2013).
Shimasaki, N. et al., "A clinically adaptable method to enhance the cytotoxicity of natural killer cells against B-cell malignancies," Cytotherapy, 14(7): 830-840 (2012).
Shook et al., "Natural Killer Cell Engineering for Cellular Therapy of Cancer," National Institutes of Health, Tissue Antigens, vol. 78, No. 6, pp. 409-415, Dec. 2011.
Shuford WW, et al., "4-1 BB costimulatory signals preferentially induce CDS+ T cell proliferation and lead to the amplification in vivo of cytotoxic T cell responses", J Exp Med. Jul. 7, 1997; 186(1):47-55.
Shum et al., "Conservation and Variation in Human and Common Chimpanzee CD($ and NKG2 Genes," The American Association of Immunologists, The Journal of Immunology, pp. 240-252, Downloaded on Jun. 18, 2017 .
Sica G, Chen L. Modulation of the immune response through 4-1BB. In: Habib N, ed. Cancer gene therapy: past achievements and future challenges. New York: Kluwer Academic/Plenum Publishers, 355-362 (2000) [Book].
Slavik et al., "CD28/CTLA-4 and CD80/CD86 families: signaling and function," Immunol Res., 19(1):1-24, 1999.
Slavin et al., "Allogcncic cell therapy with donor peripheral blood cells and recombinant human interleukin-2 to treat leukemia relapse after allogeneie bone marrow transplantation," Blood, Mar. 1996, 87(6): 2195-204.
Sneller, M.C. et al., "IL-15 administered by continuous infusion to rhesus macaques induces massive expansion of CD8+ T effector memory population in peripheral blood," Blood, 118(26): 6845-6848 (2011).
Somanchi, S.S. et al., "Expansion, purification, and functional assessment of human peripheral blood NK cells," Journal of Visualized Experiments, 48A: 2540 (2011).
Song et al., "Chimeric NKG2D CAR-Expressing T Cell-Mediated Attack of Human Ovarian Cancer is Enhanced by Histone Deacetylase Inhibition," Human Gene Therapy, vol. 24, pp. 295-305, Mar. 2013.
Spear et al., "Chimeric Antigen Receptor T Cells Shape Myeloid Cell Function within the Tumor Microenvironment through IFN-γ and GM-CSF," The Journal of Immunology, pp. 63 89-6399, 2014.
Spear et al., "Collaboration of chimeric antigen receptor (CAR)-expressing T cells and host T cells for optimal elimination of established ovarian tumors," OncoImmunology, vol. 2, No. 2, 12 pages, Apr. 2013.
Spear et al., "NKGZD CAR T-cell therapy inhibits the growth of NKG2D ligand heterogeneous tumors," Immunology and Cell Biology, vol. 91, pp. 435-440, 2013.
Srinivasan et al., "A retro-inverso peptide mimic of CD28 encompassing the MYPPPY motif adopts a polyproline type II helix and inhibits encephalitogenic T cells in vitro," J Immunol., 167(1):578-585, Jul. 1, 2001.
Srivannaboon et al., "Interleukin-4 variant (BAY 36-1677) selectively induces apoptosis in acute lymphoblastic leukemia cells," Blood, Feb. 2001, 97(3): 752-8.
Stamper et al., "Crystal structure of the B7-1/CTLA-4 complex that inhibits human immune responses," Nature, 410(6828):608-611, Mar. 29, 2001.
Stein, P.H., et al., "The Cytoplasmic Domain of CD28 is both Necessary and Sufficient for Costimulation of Interleukin-2 Secretion and Association With Phosphatidylinositol 3'-Kinase," Mol. Cell. Biol. 14: 3392-3402 (1994).
Stong RC, et al., "Human acute leukemia cell line with the t(4;11) chromosomal rearrangement exhibits B lineage and monocytic characteristics," Blood, l985,65:21-31.
Sun, J ., et al., "Early transduction produces highly functional chimeric antigen receptor-modified virus-specific T-cells with central memory markers: a Production Assistant for Cell Therapy (PACT) translational application," J. Immunother. Cancer (2015).
Sundstrom and Nilsson, "Establishment and characterization of a human histiocytic lymphoma cel line (U-937)," Int J Cancer, May 1976, 17(5): 565-77.
Sussman et al., "Protein Data Bank (PDB): database of three-dimensional structural information of biological macromolecules," Acta Crystallogr D Biol Crystallogr, 54(Pt 6 Pt 1):1078-1084, Nov. 1, 1998.
Swerdlow, S.H. et al., eds, "WHO Classification of Tumours of Haematopoietic and Lymphoid Tissues," International Agency for Research on Cancer (IARC) (4th ed. 2008) (Excerpts).
Tacke et al., "CD28-mediated induction of proliferation in resting T cells in vitro and in vivo without engagement of the T cell receptor: evidence for functionally distinct forms of CD28," Eur J Immunol., 27(1):239-247, Jan. 1997.
Tagaya, Y. et al., "IL-15: a pleiotropic cytokine with diverse receptor/signaling pathways whose expression is controlled at multiple levels," Immunity, 4(4): 329-336 (1996).
Takahashi C, et al., "Cutting edge: 4-1 BB is a bona fide CD5 T cell survival signal", J Immunol. May 1, 1999; 162(9):5037-5040.
Thomas et al., "Monoclonal antibody therapy with rituximab for acute lymphoblastic leukemia," Hematol Oncol Clin North Am., 23(5):949-971, Oct. 2009.
Topp, M.S., et al., "Universal chimeric immunoreceptors for targeting B-cell malignancies with engineered CTL: combining CD19-specific TCR zeta signaling with engineered CD28-mediated co-stimulation," Mol. Ther. 3(5)(part 2 of 2): S21 (2001).
Tsukamoto, K. er al., "Juxtacrine function of interleukin-15/interleukin-15 receptor system in tumour derived human B-cell lines," *Clinical and Experimental Immunology*, 146(3): 559-566 (2006).
Trinchieri et al., "Response of resting human peripheral blood natural killer cells to interleukin 2," J Exp Med, Oct. 1984, 160(4): 1147-69.
Trompeter et al., "Rapid and highly efficient gene transfer into natural killer cells by nucelofection," J Immunol Methods, Mar. 2003, 274(1-2): 245-56.
Turtle, "Therapy of B Cell Malignancies with CD19-Specific Chimeric Antigen Receptor Modified T Cells of Defined Subset Composition," Blood 124(21): 384-384, 2014.
Turtle, C.J., et al., Abstract, "A Phase I/II Clinical Trial of Immunotherapy for CD19+ B Cell Malignancies With Defined Composition of CD4+ and CD8+ Central Memory T Cells Lentivirally Engineered to Express a CD19-Specific Chimeric Antigen Receptor" Mol. Ther., 2014, 22(Supp.1):296.
Upshaw et al., "NKG2D-mediated signaling requires a DAP10-bound Grb2-Vav! intermediate and hosphatidylinositol-3-kinase in human natural killer cells," Nature Immunology, vol. 7, No. 5, pp. 524-532, May 2006.
Verdonck et al., "Donor leukocyte infusions for recurrent hematologic malignancies after allogeneic bone marrow transplantation: impact of infused and residual donor T cells," Bone Marrow Transplant, Dec. 1998, 22(11): 1057-63.

(56) References Cited

OTHER PUBLICATIONS

Verma and Stock, "Management of adult acute lymphoblastic leukemia: moving toward a risk-adapted approach," Curr Opin Oncol, Jan. 2001, 13(1): 14-20.
Vinay, DS et al., "Rose of 4-1 BB in immune responses", Seminars in Immunol. Dec. 1998; 10(6):481-489.
Viola, "The amplification of TCR signaling by dynamic membrane microdomains," Trends Immunol., 22(6):322-327, Jun. 2001.
Vivier, E. et al., "Innate or adaptive immunity? The example of natural killer cells," Science, 331(6013): 44-49 (2011).
Voss et al., "Targeting p53, hdm2, and CD19: vaccination and immunologic strategies," Bone Marrow Transplant, 25 Suppl 2:S43-S45, May 2000.
Vujanovic, L. et al., "Virally infected and matured human dendritic cells activate natural killer cells via cooperative activity of plasma membrane-bound TNF and IL-15," Blood, 116(4): 575-5 83 (2010).
Waldmann, T.A. et al., "Safety (toxicity), pharmcokinetics, immunogenicity, and impact on elements of the normal immune system of recombinant human IL-15 in rhesus macaques," *Blood*, 117(18): 4787-4795 (2011).
Walter et al., "Reconstitution of cellular immunity against cytomegalovirus in recipients of allogeneic bone marrow by transfer of T-cell clones from the donor," N Engl J Med, Oct. 1995, 333(16): 1038-44.
Wang, et al., "Phase I Studies of central-memory-derived CD19 CAR T cell therapy following autologous HSCT in patients with B-Cell NHL," Blood (forthcoming 2016).
Warrens AN, et al., "Splicing by overlap extension by PCR using asymmetric amplification: an improved technique for the generation of hybrid proteins of immunological interest," Gene 20;186: 29-35 (1997).
Watzl, C., et al., "Signal Transduction During Activation and Inhibition of Natural Killer Cells", Curr Protoc Immunol., Aug. 2010, pp. 1-19.
Weijtens, M.E.M., et al., "Functional balance between T cell chimeric receptor density and tumor associated antigen density: CTL mediated cytolysis and lymphokine production," Gene Ther. 7: 35-42 (2000).
Weissman et al., "Molecular cloning and chromosomal localization of the human T-cell receptor ~ chain: Distinction from the molecular CD3 complex," PNAS USA, 1988, 85:9709-9713.
Westwood, J.A., et al., "Adoptive transfer of T cells modified with a humanized chimeric receptor gene inhibits growth of Lewis-Y expressing tumors in mice," PNAS 102(52): 19051-19056 (2005).
WHO, "WHO Classification of Tumours of Hacmatopoictic and Lymphoid Tissucs," International Agency for Research on Cancer (IARC), 4th Edition, 40 pages, 2008.
Willimsky, G. and Blankenstein, T., "Sporadic immunogenic tumours avoid destruction by inducing T-cell tolerance," Nature 437: 141-146 (2005).
Wittnebel, S. et al., "Membrane-bound interleukin (IL)-15 on renal tumor cells rescues natural killer cells from IL-2 starvation-induced apoptosis," Cancer Research, 67(12): 5594-5599 (2007).
Wu and Lanier, "Natural killer cells and cancer," Adv Cancer Res, 2003, 90: 127-56.
Wu, et al. "An Activating Immunoreceptor Complex Formed by NKG2D and DAP10," Science, vol. 285, pp. 730-732, Jul. 30, 1999.
Wyss-Coray, T., et al., "The B7 adhesion molecule is expressed on activated human T cells: functional involvement in T-T cell interactions," Eur. J. Immunol, 23: 2175-2180 (1993).
Xu, Y., et al., "Closely related T-memory stem cells correlate with in vivo expansion of CAR.CD19- T cells and are preserved by IL-7 and IL-15," Blood 123(24):3750-3759 (2014).
Yan et al., "Murine COB lymphocyte expansion in vitro by artificial antigen-presenting cells expressing CD137L (4-1 BBL) is superior to CD28, and CD137L expressed on neuroblastoma expands COB tumour-reactive effector cells in vivo," Immunology, 2004, 112(1):105-116.
Ye et al., "Gene therapy for cancer using single-chain Fv fragments specific for 4-1BB," Nat Med, Apr. 2002, 8(4): 343-8.
Yeoh et al., "Classification, subtype discovery, and prediction of outcome in pediatric acute lymphoblastic leukemia by gene expression profiling," Cancer Cell, Mar. 2002, 1(2): 133-43.
Yoshida et al., "A novel adenovirus expressing human 4-1BB ligand enhances antitumor immunity," Cancer Immunol Immunother, Feb. 2003, 52(2): 97-106.
Zanoni, I. et al., "IL-15 cis presentation is required for optimal NK cell activation in lipopolysaccharide-mediated inflammatory conditions," *Cell Reports*, 4: 1235-1249 (2013).
Zeis, M. et al., "Allogeneic MHC-Mismatched Activated Natural Killer Cells Administered After Bone Marrow Transplantation Provide a Strong Graft-Versus-Leukemia Effect in Mice," BrJ Haematol, 1997, pp. 757-761, vol. 96.
Zhang et al., "Chimeric NKG2D-Modified T Cells Inhibit Systemic T-Cell Lymphoma Growth in a Manner Involving Multiple Cytokines and Cytotoxic Pathways," Cancer Research, vol. 67, No. 22, pp. 11029-11036, Nov. 15, 2007.
Zhang et al., "Chimeric NK-receptor-bearing T cells mediate antitumor immunotherapy," Gene Therapy, Blood, vol. 106, No. 5, pp. 1544-1551, Sep. 2005.
Zhang, J. et al., "Characterization of interleukin-15-gene-modified human natural killer cells: implications for adoptive cellular immunotherapy," Haematologica, 89(3): 338-347 (2004).
Zhang et al., "Generation of Antitumor Responses by Genetic Modification of Primary Human T Cells with a Chimeric NKG2D Receptor," Cancer Research, vol. 66, No. 11, pp. 5927-5933, Jun. 1, 2006.
Zhang et al., "Mouse Tumor Vasculature Expresses NKG2D Ligands and Can Be Targeted by Chimeric NKG2D-Modified T Cells," The Journal of Immunology, pp. 2455-2463, (2013) Downloaded Feb. 20, 2018.
Brand, L.J. et al., "Abstract LB-185: A PSMA-directed natural killer cell approach for prostate cancer immunotherapy," Cancer Research, 77(13 Supplement): Abstract No. LB-185 (Jul. 2017).
Chang et al., "Five Different Anti-Prostate-specific Membrane Antigen (PSMA) Antibodies Confirm PSMA Expression in Tumor-associated Neovasculature," Cancer Res. 59: 3192-3198 (1999).
Grauer et al., "Identification, Purification, and Subcellular Localization of Prostate-specific Membrane Antigen PSM' Protein in the LNCaP Prostatic Carcinoma Cell Line," Cancer Res. 58: 4787-4789 (1998).
Kaiser, B.K. et al., "Structural basis for NKG2A/CD94 Recognition of HLA-E," Proc Nat'l Acad Sci USA, 105(18): 6696-6701 (April 2008).
LaBonte, M.L. et al., "Molecular Determinants Regulating the Pairing of NKG2 Molecules with CD94 for Cell Surface Heterodimer Expression," J Immunol, 172(11): 6902-6912 (May 2004).
Sullivan, L.C. et al., "The Heterodimeric Assembly of the CD94-NKG2 Receptor Family and Implications for Human Leukocyte Antigen-E Recognition," Immunity, 27(6): 900-911 (Dec. 2007).
Zah, E. et al., "T Cells Expressing CD19/CD20 Bispecific Chimeric Antigen Receptors Prevent Antigen Escape by Malignant B Cells," Cancer Immunol Res, 4(6): 498-508 (Apr. 2016).
International Search Report and Written Opinion dated Jul. 4, 2018 for International Application No. PCT/SG2018/050138, entitled "Stimulatory Cell Lines for Ex Vivo Expansion and Activation of Natural Killer Cells".
International Preliminary Report on Patentability for International Application No. PCT/SG2018/050138, entitled "Stimulatory Cell Lines for Ex Vivo Expansion and Activation of Natural Killer Cells," dated Oct. 1, 2019.
Ye et al. "Effects of target cell overexpression of IL-15, 4-1 BBL and IL-18 1-102 combine with IL-2 on NK cell activation and cytotoxicity during ex vivo expansion" Chin J Cancer Biother, Oct. 31, 2014, vol. 21, No. 5, pp. 537-542.
Huang Q.S. et al, "Expansion of human natural killer cells ex vivo," Chine J Cell Mol Immunol, Dec. 31, 2008, vol. 24, No. 12, pp. 1167-1170.
Santegoets S.J. et al, "IL-21 promotes the expansion of CD27+ CD28+ tumor infiltrating lymphocytes with high cytotoxic potential and low collateral expansion of regulatory T cells," Journal of Translational Medicine, Feb. 12, 2013, vol. 11, No. 37, pp. e1-e10.

(56) References Cited

OTHER PUBLICATIONS

Qi L. et al., "Multiple effects of IL-21 on the ex vivo expansion of human primary NK cells," Immunology, Nov. 28, 2014, vol. 143, No. S2, p. 62-176, Poster Abstract 708.

Li, Q. et al, "Bifacial effects of engineering tumour cell-derived exosomes on human natural killer cells" Experimental Cell Research, Dec. 19, 2017, vol. 363, No. 2, pp. 141-150

Pakula, A.A. et al., "Genetic analysis of protein stability and function," Annual Review of Genetics, V. 23, N. 1, p. 289-310, c. 305-306 (1989).

Abakushina, E.V., "Immunotherapy With Natural Killer Cells in the Treatment of Cancer," Russian Journal of Immunology, vol. 10, No. 2, pp. 131-142 (2016) (Abstract only).

Dowell, A. C. , "Studies of Human T cell Costimulation:Potential for the Immunotherapy of Cancer," A thesis submitted to the University of Birmingham for the degree of Doctor of Philosophy, Cruk Institute for Cancer Studies, 2010.

Hasan, A.N., "Soluble and membrane-bound interleukin (IL)-15 Ra/IL-15 complexesmediate proliferation of high-avidity central memory CD81T cells foradoptive immunotherapy of cancer and infections," Clinical and Experimental Immunology, 186: 249-265, 2016.

Zhang et al., "Improving Adoptive T Cell Therapy by Targeting and Controlling IL-12 Expression to the Tumor Environment," The American Society of Gene & Cell Therapy Molecular Therapy, vol. 19, No. 4, 751-759, 2011.

Ren, P.- P. et al., Anti-EGFRvIII Chimeric Antigen Receptor-Modified T Cells for Adoptive Cell Therapy of Glioblastoma, Current Pharmaceutical Design, 23(14), 2113-2116 (2017).

Morgan, R.A. et al., Recognition of Glioma Stem Cells by Genetically Modified T Cells Targeting EGFRvIII and Development of Adoptive Cell Therapy for Glioma, Human Gene Therapy, 23(10), 1043-1053 (2012).

Dalal, A.-R. et al., Third-Generation Human Epidermal Growth Factor Receptor 2 Chimeric Antigen Receptor Expression on Human T Cells Improves with Two-Signal Activation, Human Gene Therapy, 845-852 (2018) (Abstract).

Choi, B. D. et al., Chimeric antigen receptor T-cell immunotherapy for glioblastoma: practical insights for neurosurgeons, Neurosurg Focus, 44(6):E13, 1-6 (2018).

Vinanica, N., et al., "Specific stimulation of T lymphocytes with erythropoietin for adoptive immunotherapy", Blood, 135(9): 668-679 (Feb. 27, 2020).

Eyguem et al., "Targeting a CAR to the TRAC locus with CRISPR/Cas9 enchances tumour rejction" Nature, 2017, 543(7643): 113-117.

Seif et al., "The role of JAK-STAT signaling pathway and its regulators in the fate of T helper cells" Cell Communication and Signaling (2017) 15:23.

Themeli et al., "Generation of tumor-targeted human T lympocytes from Induced pluripotent stem cells for cancer therapy", Nat Biotechnol., Oct. 2013; 31(10): 928-933.

Watowich et al., "The Erythropoietin Receptor: Molecular Structure and Hematopoietic Signaling Pathways," J. Investig Med. 2011, 59(7): 1067-1072.

* cited by examiner

A
41BBL
mbIL15
mbIL12A/12B
K562
B
41BBL
mbIL15
mbIL18
K562
C
41BBL
mbIL15
mbIL12A/12B
mbIL18
K562
D
41BBL
mbIL15
mbIL12A/12B
mbantiCD3
K562
E
41BBL
mbIL15
mbIL18
mbantiCD3
K562
F
41BBL
mbIL15
mbIL12A/12B
mbIL18
mbantiCD3
K562
G
41BBL
mbIL15
mbantiCD3
K562

A
mb IL-15
B
41BBL
C
mb IL-18
D
mb IL-12A
E
mb IL-12B
F
mb anti CD3

A
K562-mb15-41BBL
population doublings
B
+mb12
C
+mb18
D
+mb12
+mb18
weeks of culture
= senescence
E
E:T 1:1
E:T 1:2
% cytotoxicity
days of culture
K562-mb15-41BBL
+mb12
+mb18
+mb12+mb18
F
Day 64
% cytotoxicity
P<0.001
E:T
+mb18
+mb12+mb18

SEQUENCE LISTING

```
<160> NUMBER OF SEQ ID NOS: 26

<210> SEQ ID NO 1
<211> LENGTH: 615
<212> TYPE: DNA
<213> ORGANISM: Homo sapiens
<220> FEATURE:
<221> NAME/KEY: misc_feature
<223> OTHER INFORMATION: Nucleic Acid sequence for mbIL15

<400> SEQUENCE: 1

atggccttac cagtgaccgc cttgctcctg ccgctggcct tgctgctcca cgccgccagg      60

ccgaactggg tgaatgtaat aagtgatttg aaaaaaattg aagatcttat tcaatctatg     120

catattgatg ctactttata tacggaaagt gatgttcacc ccagttgcaa agtaacagca     180

atgaagtgct ttctcttgga gttacaagtt atttcacttg agtccggaga tgcaagtatt     240

catgatacag tagaaaatct gatcatccta gcaaacaaca gtttgtcttc taatgggaat     300

gtaacagaat ctggatgcaa agaatgtgag gaactggagg aaaaaaatat taaagaattt     360

ttgcagagtt ttgtacatat tgtccaaatg ttcatcaaca cttctaccac gacgccagcg     420
```

```
ccgcgaccac caacaccggc gcccaccatc gcgtcgcagc ccctgtccct gcgcccagag    480

gcgtgccggc cagcggcggg gggcgcagtg cacacgaggg ggctggactt cgcctgtgat    540

atctacatct gggcgccctt ggccgggact tgtggggtcc ttctcctgtc actggttatc    600

accctttact gctaa                                                     615
```

<210> SEQ ID NO 2
<211> LENGTH: 204
<212> TYPE: PRT
<213> ORGANISM: Homo sapiens
<220> FEATURE:
<221> NAME/KEY: MISC_FEATURE
<223> OTHER INFORMATION: Amion Acid sequence for mbIL15

<400> SEQUENCE: 2

```
Met Ala Leu Pro Val Thr Ala Leu Leu Leu Pro Leu Ala Leu Leu Leu
1               5                   10                  15

His Ala Ala Arg Pro Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser Thr Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Ile Tyr Ile Trp Ala Pro Leu Ala Gly Thr Cys Gly
            180                 185                 190

Val Leu Leu Leu Ser Leu Val Ile Thr Leu Tyr Cys
        195                 200
```

<210> SEQ ID NO 3
<211> LENGTH: 867
<212> TYPE: DNA
<213> ORGANISM: Homo sapiens
<220> FEATURE:
<221> NAME/KEY: misc_feature
<223> OTHER INFORMATION: Nucleic Acid sequence for mbIL12A

<400> SEQUENCE: 3

```
atggccttac cagtgaccgc cttgctcctg ccgctggcct tgctgctcca cgccgccagg     60

ccgagaaacc tccccgtggc cactccagac ccaggaatgt tcccatgcct tcaccactcc    120

caaaacctgc tgagggccgt cagcaacatg ctccagaagg ccagacaaac tctagaattt    180

tacccttgca cttctgaaga gattgatcat gaagatatca caaaagataa aaccagcaca    240

gtggaggcct gtttaccatt ggaattaacc aagaatgaga gttgcctaaa ttccagagag    300
```

```
acctctttca taactaatgg gagttgcctg gcctccagaa agacctcttt tatgatggcc    360

ctgtgcctta gtagtattta tgaagacttg aagatgtacc aggtggagtt caagaccatg    420

aatgcaaagc ttctgatgga tcctaagagg cagatctttc tagatcaaaa catgctggca    480

gttattgatg agctgatgca ggccctgaat ttcaacagtg agactgtgcc acaaaaatcc    540

tcccttgaag aaccggattt ttataaaact aaaatcaagc tctgcatact tcttcatgct    600

ttcaggattc gggcagtgac tattgataga gtgatgagct atctgaatgc ttccaagccc    660

accacgacgc cagcgccgcg accaccaaca ccggcgccca ccatcgcgtc gcagcccctg    720

tccctgcgcc cagaggcgtg ccggccagcg gcggggggcg cagtgcacac gagggggctg    780

gacttcgcct gtgatatcta catctgggcg cccttggccg ggacttgtgg ggtccttctc    840

ctgtcactgg ttatcaccct ttactaa                                        867
```

<210> SEQ ID NO 4
<211> LENGTH: 288
<212> TYPE: PRT
<213> ORGANISM: Homo sapiens
<220> FEATURE:
<221> NAME/KEY: MISC_FEATURE
<223> OTHER INFORMATION: Amino Acid sequence for mbIL12A

<400> SEQUENCE: 4

```
Met Ala Leu Pro Val Thr Ala Leu Leu Leu Pro Leu Ala Leu Leu Leu
1               5                   10                  15

His Ala Ala Arg Pro Arg Asn Leu Pro Val Ala Thr Pro Asp Pro Gly
            20                  25                  30

Met Phe Pro Cys Leu His His Ser Gln Asn Leu Leu Arg Ala Val Ser
        35                  40                  45

Asn Met Leu Gln Lys Ala Arg Gln Thr Leu Glu Phe Tyr Pro Cys Thr
    50                  55                  60

Ser Glu Glu Ile Asp His Glu Asp Ile Thr Lys Asp Lys Thr Ser Thr
65                  70                  75                  80

Val Glu Ala Cys Leu Pro Leu Glu Leu Thr Lys Asn Glu Ser Cys Leu
                85                  90                  95

Asn Ser Arg Glu Thr Ser Phe Ile Thr Asn Gly Ser Cys Leu Ala Ser
            100                 105                 110

Arg Lys Thr Ser Phe Met Met Ala Leu Cys Leu Ser Ser Ile Tyr Glu
        115                 120                 125

Asp Leu Lys Met Tyr Gln Val Glu Phe Lys Thr Met Asn Ala Lys Leu
    130                 135                 140

Leu Met Asp Pro Lys Arg Gln Ile Phe Leu Asp Gln Asn Met Leu Ala
145                 150                 155                 160

Val Ile Asp Glu Leu Met Gln Ala Leu Asn Phe Asn Ser Glu Thr Val
                165                 170                 175

Pro Gln Lys Ser Ser Leu Glu Glu Pro Asp Phe Tyr Lys Thr Lys Ile
            180                 185                 190

Lys Leu Cys Ile Leu Leu His Ala Phe Arg Ile Arg Ala Val Thr Ile
        195                 200                 205

Asp Arg Val Met Ser Tyr Leu Asn Ala Ser Lys Pro Thr Thr Thr Pro
    210                 215                 220

Ala Pro Arg Pro Pro Thr Pro Ala Pro Thr Ile Ala Ser Gln Pro Leu
225                 230                 235                 240

Ser Leu Arg Pro Glu Ala Cys Arg Pro Ala Ala Gly Gly Ala Val His
                245                 250                 255
```

```
Thr Arg Gly Leu Asp Phe Ala Cys Asp Ile Tyr Ile Trp Ala Pro Leu
            260                 265                 270

Ala Gly Thr Cys Gly Val Leu Leu Leu Ser Leu Val Ile Thr Leu Tyr
        275                 280                 285


<210> SEQ ID NO 5
<211> LENGTH: 1194
<212> TYPE: DNA
<213> ORGANISM: Homo sapiens
<220> FEATURE:
<221> NAME/KEY: misc_feature
<223> OTHER INFORMATION: Nucleic Acid sequence for mbIL12B

<400> SEQUENCE: 5

atggccttac cagtgaccgc cttgctcctg ccgctggcct tgctgctcca cgccgccagg     60

ccgatatggg aactgaagaa agatgtttat gtcgtagaat tggattggta tccggatgcc    120

cctggagaaa tggtggtcct cacctgtgac acccctgaag aagatggtat cacctggacc    180

ttggaccaga gcagtgaggt cttaggctct ggcaaaaccc tgaccatcca agtcaaagag    240

tttggagatg ctggccagta cacctgtcac aaaggaggcg aggttctaag ccattcgctc    300

ctgctgcttc acaaaaagga agatggaatt tggtccactg atattttaaa ggaccagaaa    360

gaacccaaaa ataagacctt tctaagatgc gaggccaaga attattctgg acgtttcacc    420

tgctggtggc tgacgacaat cagtactgat ttgacattca gtgtcaaaag cagcagaggc    480

tcttctgacc cccaaggggt gacgtgcgga gctgctacac tctctgcaga gagagtcaga    540

ggggacaaca aggagtatga gtactcagtg gagtgccagg aggacagtgc ctgcccagct    600

gctgaggaga gtctgcccat tgaggtcatg gtggatgccg ttcacaagct caagtatgaa    660

aactacacca gcagcttctt catcagggac atcatcaaac ctgacccacc caagaacttg    720

cagctgaagc cattaaagaa ctctcggcag gtggaggtca gctgggagta ccctgacacc    780

tggagtactc cacattccta cttctccctg acattctgcg ttcaggtcca gggcaagagc    840

aagagagaaa agaaagatag agtcttcacg gacaagacct cagccacggt catctgccgc    900

aaaaatgcca gcattagcgt gcgggcccag gaccgctact atagctcatc ttggagcgaa    960

tgggcatctg tgccctgcag taagcccacc acgacgccag cgccgcgacc accaacaccg   1020

gcgcccacca tcgcgtcgca gcccctgtcc ctgcgcccag aggcgtgccg gccagcggcg   1080

gggggcgcag tgcacacgag ggggctggac ttcgcctgtg atatctacat ctgggcgccc   1140

ttggccggga cttgtggggt ccttctcctg tcactggtta tcaccettta ctaa          1194


<210> SEQ ID NO 6
<211> LENGTH: 397
<212> TYPE: PRT
<213> ORGANISM: Homo sapiens
<220> FEATURE:
<221> NAME/KEY: MISC_FEATURE
<223> OTHER INFORMATION: Amino Acid sequence for mbIL12B

<400> SEQUENCE: 6

Met Ala Leu Pro Val Thr Ala Leu Leu Leu Pro Leu Ala Leu Leu Leu
1               5                   10                  15

His Ala Ala Arg Pro Ile Trp Glu Leu Lys Lys Asp Val Tyr Val Val
            20                  25                  30

Glu Leu Asp Trp Tyr Pro Asp Ala Pro Gly Glu Met Val Val Leu Thr
        35                  40                  45

Cys Asp Thr Pro Glu Glu Asp Gly Ile Thr Trp Thr Leu Asp Gln Ser
    50                  55                  60
```

```
Ser Glu Val Leu Gly Ser Gly Lys Thr Leu Thr Ile Gln Val Lys Glu
65                  70                  75                  80

Phe Gly Asp Ala Gly Gln Tyr Thr Cys His Lys Gly Gly Glu Val Leu
                85                  90                  95

Ser His Ser Leu Leu Leu Leu His Lys Lys Glu Asp Gly Ile Trp Ser
            100                 105                 110

Thr Asp Ile Leu Lys Asp Gln Lys Glu Pro Lys Asn Lys Thr Phe Leu
        115                 120                 125

Arg Cys Glu Ala Lys Asn Tyr Ser Gly Arg Phe Thr Cys Trp Trp Leu
    130                 135                 140

Thr Thr Ile Ser Thr Asp Leu Thr Phe Ser Val Lys Ser Ser Arg Gly
145                 150                 155                 160

Ser Ser Asp Pro Gln Gly Val Thr Cys Gly Ala Ala Thr Leu Ser Ala
                165                 170                 175

Glu Arg Val Arg Gly Asp Asn Lys Glu Tyr Glu Tyr Ser Val Glu Cys
            180                 185                 190

Gln Glu Asp Ser Ala Cys Pro Ala Ala Glu Glu Ser Leu Pro Ile Glu
        195                 200                 205

Val Met Val Asp Ala Val His Lys Leu Lys Tyr Glu Asn Tyr Thr Ser
    210                 215                 220

Ser Phe Phe Ile Arg Asp Ile Ile Lys Pro Asp Pro Pro Lys Asn Leu
225                 230                 235                 240

Gln Leu Lys Pro Leu Lys Asn Ser Arg Gln Val Glu Val Ser Trp Glu
                245                 250                 255

Tyr Pro Asp Thr Trp Ser Thr Pro His Ser Tyr Phe Ser Leu Thr Phe
            260                 265                 270

Cys Val Gln Val Gln Gly Lys Ser Lys Arg Glu Lys Lys Asp Arg Val
        275                 280                 285

Phe Thr Asp Lys Thr Ser Ala Thr Val Ile Cys Arg Lys Asn Ala Ser
    290                 295                 300

Ile Ser Val Arg Ala Gln Asp Arg Tyr Tyr Ser Ser Ser Trp Ser Glu
305                 310                 315                 320

Trp Ala Ser Val Pro Cys Ser Lys Pro Thr Thr Thr Pro Ala Pro Arg
                325                 330                 335

Pro Pro Thr Pro Ala Pro Thr Ile Ala Ser Gln Pro Leu Ser Leu Arg
            340                 345                 350

Pro Glu Ala Cys Arg Pro Ala Ala Gly Gly Ala Val His Thr Arg Gly
        355                 360                 365

Leu Asp Phe Ala Cys Asp Ile Tyr Ile Trp Ala Pro Leu Ala Gly Thr
    370                 375                 380

Cys Gly Val Leu Leu Leu Ser Leu Val Ile Thr Leu Tyr
385                 390                 395
```

<210> SEQ ID NO 7
<211> LENGTH: 747
<212> TYPE: DNA
<213> ORGANISM: Homo sapiens
<220> FEATURE:
<221> NAME/KEY: misc_feature
<223> OTHER INFORMATION: Nucleic Acid sequence for mbIL18

<400> SEQUENCE: 7

```
atggccttac cagtgaccgc cttgctcctg ccgctggcct tgctgctcca cgccgccagg      60

ccgtactttg gcaagcttga atctaaatta tcagtcataa gaaatttgaa tgaccaagtt     120
```

```
ctcttcattg accaaggaaa tcggcctcta tttgaagata tgactgattc tgactgtaga    180

gataatgcac cccggaccat atttattata agtatgtata aagatagcca gcctagaggt    240

atggctgtaa ctatctctgt gaagtgtgag aaaatttcaa ctctctcctg tgagaacaaa    300

attatttcct ttaaggaaat gaatcctcct gataacatca aggatacaaa aagtgacatc    360

atattctttc agagaagtgt cccaggacat gataataaga tgcaatttga atcttcatca    420

tacgaaggat actttctagc ttgtgaaaaa gagagagacc tttttaaact cattttgaaa    480

aaagaggatg aattggggga tagatctata atgttcactg ttcaaaacga agacaagccc    540

accacgacgc cagcgccgcg accaccaaca ccggcgccca ccatcgcgtc gcagcccctg    600

tccctgcgcc cagaggcgtg ccggccagcg gcggggggcg cagtgcacac gagggggctg    660

gacttcgcct gtgatatcta catctgggcg cccttggccg ggacttgtgg ggtccttctc    720

ctgtcactgg ttatcaccct ttactaa                                        747
```

<210> SEQ ID NO 8
<211> LENGTH: 248
<212> TYPE: PRT
<213> ORGANISM: Homo sapiens
<220> FEATURE:
<221> NAME/KEY: MISC_FEATURE
<223> OTHER INFORMATION: Amino Acid sequence for mbIL18

<400> SEQUENCE: 8

```
Met Ala Leu Pro Val Thr Ala Leu Leu Leu Pro Leu Ala Leu Leu Leu
1               5                   10                  15

His Ala Ala Arg Pro Tyr Phe Gly Lys Leu Glu Ser Lys Leu Ser Val
            20                  25                  30

Ile Arg Asn Leu Asn Asp Gln Val Leu Phe Ile Asp Gln Gly Asn Arg
        35                  40                  45

Pro Leu Phe Glu Asp Met Thr Asp Ser Asp Cys Arg Asp Asn Ala Pro
    50                  55                  60

Arg Thr Ile Phe Ile Ile Ser Met Tyr Lys Asp Ser Gln Pro Arg Gly
65                  70                  75                  80

Met Ala Val Thr Ile Ser Val Lys Cys Glu Lys Ile Ser Thr Leu Ser
                85                  90                  95

Cys Glu Asn Lys Ile Ile Ser Phe Lys Glu Met Asn Pro Pro Asp Asn
            100                 105                 110

Ile Lys Asp Thr Lys Ser Asp Ile Ile Phe Phe Gln Arg Ser Val Pro
        115                 120                 125

Gly His Asp Asn Lys Met Gln Phe Glu Ser Ser Ser Tyr Glu Gly Tyr
    130                 135                 140

Phe Leu Ala Cys Glu Lys Glu Arg Asp Leu Phe Lys Leu Ile Leu Lys
145                 150                 155                 160

Lys Glu Asp Glu Leu Gly Asp Arg Ser Ile Met Phe Thr Val Gln Asn
                165                 170                 175

Glu Asp Lys Pro Thr Thr Thr Pro Ala Pro Arg Pro Pro Thr Pro Ala
            180                 185                 190

Pro Thr Ile Ala Ser Gln Pro Leu Ser Leu Arg Pro Glu Ala Cys Arg
        195                 200                 205

Pro Ala Ala Gly Gly Ala Val His Thr Arg Gly Leu Asp Phe Ala Cys
    210                 215                 220

Asp Ile Tyr Ile Trp Ala Pro Leu Ala Gly Thr Cys Gly Val Leu Leu
225                 230                 235                 240

Leu Ser Leu Val Ile Thr Leu Tyr
```

245

<210> SEQ ID NO 9
<211> LENGTH: 706
<212> TYPE: DNA
<213> ORGANISM: Homo sapiens
<220> FEATURE:
<221> NAME/KEY: misc_feature
<223> OTHER INFORMATION: Nucleic Acid sequence for mbIL21
<220> FEATURE:
<221> NAME/KEY: misc_feature
<223> OTHER INFORMATION: Nucleic Acid sequence for IL21

<400> SEQUENCE: 9

```
gctgaagtga aaacgagacc aaggtctagc tctactgttg gtacttatga gatccagtcc     60

tggcaacatg gagaggattg tcatctgtct gatggtcatc tcttggggac actggtccac    120

aaatcaagct cccaaggtca agatcgccac atgattagaa tgcgtcaact tatagatatt    180

gttgatcagc tgaaaaatta tgtgaatgac ttggtccctg aatttctgcc agctccagaa    240

gatgtagaga caaactgtga gtggtcagct ttttcctgct ttcagaaggc ccaactaaag    300

tcagcaaata caggaaacaa tgaaaggata atcaatgtat caattaaaaa gctgaagagg    360

aaaccacctt ccacaaatgc agggagaaga cagaaacaca gactaacatg cccttcatgt    420

gattcttatg agaaaaaacc acccaaagaa ttcctagaaa gattcaaatc acttctccaa    480

aaggtatcta ccttaagttt catttgattt tctgctttat ctttacctat ccagatttgc    540

ttcttagtta ctcacggtat actatttcca cagatgattc atcagcatct gtcctctaga    600

acacacggaa gtgaagattc ctgaggatct aacttgcagt tggacactat gttacatact    660

ctaatatagt agtgaaagtc atttctttgt attccaagtg gaggag                   706
```

<210> SEQ ID NO 10
<211> LENGTH: 155
<212> TYPE: PRT
<213> ORGANISM: Homo sapiens
<220> FEATURE:
<221> NAME/KEY: MISC_FEATURE
<223> OTHER INFORMATION: Amino Acid sequence for mbIL21
<220> FEATURE:
<221> NAME/KEY: MISC_FEATURE
<223> OTHER INFORMATION: Amino Acid sequence for IL21

<400> SEQUENCE: 10

```
Met Glu Arg Ile Val Ile Cys Leu Met Val Ile Phe Leu Gly Thr Leu
1               5                   10                  15

Val His Lys Ser Ser Ser Gln Gly Gln Asp Arg His Met Ile Arg Met
            20                  25                  30

Arg Gln Leu Ile Asp Ile Val Asp Gln Leu Lys Asn Tyr Val Asn Asp
        35                  40                  45

Leu Val Pro Glu Phe Leu Pro Ala Pro Glu Asp Val Glu Thr Asn Cys
    50                  55                  60

Glu Trp Ser Ala Phe Ser Cys Phe Gln Lys Ala Gln Leu Lys Ser Ala
65                  70                  75                  80

Asn Thr Gly Asn Asn Glu Arg Ile Ile Asn Val Ser Ile Lys Lys Leu
                85                  90                  95

Lys Arg Lys Pro Pro Ser Thr Asn Ala Gly Arg Arg Gln Lys His Arg
            100                 105                 110

Leu Thr Cys Pro Ser Cys Asp Ser Tyr Glu Lys Lys Pro Pro Lys Glu
        115                 120                 125

Phe Leu Glu Arg Phe Lys Ser Leu Leu Gln Lys Met Ile His Gln His
```

```
    130                 135                 140

Leu Ser Ser Arg Thr His Gly Ser Glu Asp Ser
145                 150                 155


<210> SEQ ID NO 11
<211> LENGTH: 1147
<212> TYPE: DNA
<213> ORGANISM: Homo sapiens
<220> FEATURE:
<221> NAME/KEY: misc_feature
<223> OTHER INFORMATION: Nucleic Acid sequence for IL22

<400> SEQUENCE: 11

cgaccaggtt ctccttcccc agtcaccagt tgctcgagtt agaattgtct gcaatggccg      60

ccctgcagaa atctgtgagc tctttcctta tggggacct ggccaccagc tgcctccttc     120

tcttggccct cttggtacag ggaggagcag ctgcgcccat cagctcccac tgcaggcttg    180

acaagtccaa cttccagcag ccctatatca ccaaccgcac cttcatgctg gctaaggagg    240

ctagcttggc tgataacaac acagacgttc gtctcattgg ggagaaactg ttccacggag    300

tcagtatgag tgagcgctgc tatctgatga agcaggtgct gaacttcacc cttgaagaag    360

tgctgttccc tcaatctgat aggttccagc cttatatgca ggaggtggtg cccttcctgg    420

ccaggctcag caacaggcta agcacatgtc atattgaagg tgatgacctg catatccaga    480

ggaatgtgca aaagctgaag gacacagtga aaaagcttgg agagagtgga gagatcaaag    540

caattggaga actggatttg ctgtttatgt ctctgagaaa tgcctgcatt tgaccagagc    600

aaagctgaaa aatgaataac taaccccctt tccctgctag aaataacaat tagatgcccc    660

aaagcgattt tttttaacca aaaggaagat gggaagccaa actccatcat gatgggtgga    720

ttccaaatga acccctgcgt tagttacaaa ggaaaccaat gccacttttg tttataagac    780

cagaaggtag actttctaag catagatatt tattgataac atttcattgt aactggtgtt    840

ctatacacag aaaacaattt attttttaaa taattgtctt tttccataaa aaagattact    900

ttccattcct ttaggggaaa aaacccctaa atagcttcat gtttccataa tcagtacttt    960

atatttataa atgtatttat tattattata agactgcatt ttatttatat cattttatta   1020

atatggattt atttatagaa acatcattcg atattgctac ttgagtgtaa ggctaatatt   1080

gatatttatg acaataatta tagagctata acatgtttat ttgacctcaa taaacacttg   1140

gatatcc                                                              1147


<210> SEQ ID NO 12
<211> LENGTH: 179
<212> TYPE: PRT
<213> ORGANISM: Homo sapiens
<220> FEATURE:
<221> NAME/KEY: MISC_FEATURE
<223> OTHER INFORMATION: Amino acid sequence for IL22

<400> SEQUENCE: 12

Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60
```

```
Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile


<210> SEQ ID NO 13
<211> LENGTH: 765
<212> TYPE: DNA
<213> ORGANISM: Homo sapiens
<220> FEATURE:
<221> NAME/KEY: misc_feature
<223> OTHER INFORMATION: Nucleic Acid sequence for 4-1BB ligand

<400> SEQUENCE: 13

atggaatacg cctctgacgc ttcactggac cccgaagccc cgtggcctcc cgcgccccgc      60

gctcgcgcct gccgcgtact gccttgggcc ctggtcgcgg ggctgctgct gctgctgctg     120

ctcgctgccg cctgcgccgt cttcctcgcc tgcccctggg ccgtgtccgg ggctcgcgcc     180

tcgcccggct ccgcggccag cccgagactc cgcgagggtc ccgagctttc gcccgacgat     240

cccgccggcc tcttggacct gcggcagggc atgtttgcgc agctggtggc ccaaaatgtt     300

ctgctgatcg atgggcccct gagctggtac agtgacccag gcctggcagg cgtgtccctg     360

acgggggggcc tgagctacaa agaggacacg aaggagctgg tggtggccaa ggctggagtc     420

tactatgtct tctttcaact agagctgcgg cgcgtggtgg ccggcgaggg ctcaggctcc     480

gtttcacttg cgctgcacct gcagccactg cgctctgctg ctggggccgc cgccctggct     540

ttgaccgtgg acctgccacc cgcctcctcc gaggctcgga actcggcctt cggtttccag     600

ggccgcttgc tgcacctgag tgccggccag cgcctgggcg tccatcttca cactgaggcc     660

agggcacgcc atgcctggca gcttacccag ggcgccacag tcttgggact cttccgggtg     720

acccccgaaa tcccagccgg actcccttca ccgaggtcgg aataa                      765


<210> SEQ ID NO 14
<211> LENGTH: 254
<212> TYPE: PRT
<213> ORGANISM: Homo sapiens
<220> FEATURE:
<221> NAME/KEY: MISC_FEATURE
<223> OTHER INFORMATION: Amino Acid sequence for 4-1BB ligand

<400> SEQUENCE: 14

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45
```

```
Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 15
<211> LENGTH: 1534
<212> TYPE: DNA
<213> ORGANISM: Homo sapiens
<220> FEATURE:
<221> NAME/KEY: misc_feature
<223> OTHER INFORMATION: Nucleic Acid sequence for CD3 Receptor epsilon subunit

<400> SEQUENCE: 15

```
tattgtcaga gtcctcttgt ttggccttct aggaaggctg tgggacccag ctttcttcaa     60

ccagtccagg tggaggcctc tgccttgaac gtttccaagt gaggtaaaac ccgcaggccc    120

agaggcctct ctacttcctg tgtggggttc agaaaccctc ctcccctccc agcctcaggt    180

gcctgcttca gaaaatgaag tagtaagtct gctggcctcc gccatcttag taaagtaaca    240

gtcccatgaa acaaagatgc agtcgggcac tcactggaga gttctgggcc tctgcctctt    300

atcagttggc gtttgggggc aagatggtaa tgaagaaatg ggtggtatta cacagacacc    360

atataaagtc tccatctctg gaaccacagt aatattgaca tgccctcagt atcctggatc    420

tgaaatacta tggcaacaca atgataaaaa cataggcggt gatgaggatg ataaaaacat    480

aggcagtgat gaggatcacc tgtcactgaa ggaattttca gaattggagc aaagtggtta    540

ttatgtctgc taccccagag gaagcaaacc agaagatgcg aacttttatc tctacctgag    600

ggcaagagtg tgtgagaact gcatggagat ggatgtgatg tcggtggcca caattgtcat    660

agtggacatc tgcatcactg gggggcttgct gctgctggtt tactactgga gcaagaatag    720

aaaggccaag gccaagcctg tgacacgagg agcgggtgct ggcggcaggc aaaggggaca    780

aaacaaggag aggccaccac ctgttcccaa cccagactat gagcccatcc ggaaaggcca    840
```

```
gcgggacctg tattctggcc tgaatcagag acgcatctga ccctctggag aacactgcct    900

cccgctggcc caggtctcct ctccagtccc cctgcgactc cctgtttcct gggctagtct    960

tggaccccac gagagagaat cgttcctcag cctcatggtg aactcgcgcc ctccagcctg   1020

atcccccgct ccctcctccc tgccttctct gctggtaccc agtcctaaaa tattgctgct   1080

tcctcttcct ttgaagcatc atcagtagtc acaccctcac agctggcctg ccctcttgcc   1140

aggatattta tttgtgctat tcactccctt ccctttggat gtaacttctc cgttcagttc   1200

cctccttttc ttgcatgtaa gttgtccccc atcccaaagt attccatcta cttttctatc   1260

gccgtcccct tttgcagccc tctctgggga tggactgggt aaatgttgac agaggccctg   1320

ccccgttcac agatcctggc cctgagccag ccctgtgctc ctccctcccc caacactccc   1380

taccaacccc ctaatcccct actccctcca ccccccctcc actgtaggcc actggatggt   1440

catttgcatc tccgtaaatg tgctctgctc ctcagctgag agagaaaaaa ataaactgta   1500

tttggctgca agaaaaaaaa aaaaaaaaaa aaaa                               1534
```

<210> SEQ ID NO 16
<211> LENGTH: 1017
<212> TYPE: DNA
<213> ORGANISM: Homo sapiens
<220> FEATURE:
<221> NAME/KEY: misc_feature
<223> OTHER INFORMATION: Nucleic Acid sequence for mb-anti-CD3 scFv

<400> SEQUENCE: 16

```
atggccttac cagtgaccgc cttgctcctg ccgctggcct tgctgctcca cgccgccagg     60

ccgcaaattg ttctcaccca gtctccagca atcatgtctg catctccagg ggagaaggtc    120

accatgacct gcagtgccag ctcaagtgta agttacatga actggtacca gcagaagtca    180

ggcacctccc ccaaaagatg gatttatgac acatccaaac tggcttctgg agtccctgct    240

cacttcaggg gcagtgggtc tgggacctct tactctctca caatcagcgg catggaggct    300

gaagatgctg ccacttatta ctgccagcag tggagtagta acccattcac gttcggctcg    360

gggacaaagt tggaaataaa ccggggtggt ggtggttctg gtggtggtgg ttctggcggc    420

ggcggctccg gtggtggtgg atccgaggtc cagctgcagc agtctggggc tgaactggca    480

agacctgggg cctcagtgaa gatgtcctgc aaggcttctg gctacacctt tactaggtac    540

acgatgcact gggtaaaaca gaggcctgga cagggtctgg aatggattgg atacattaat    600

cctagccgtg gttatactaa ttacaatcag aagttcaagg acaaggccac attgactaca    660

gacaaatcct ccagcacagc ctacatgcaa ctgagcagcc tgacatctga ggactctgca    720

gtctattact gtgcaagata ttatgatgat cattactgcc ttgactactg gggccaaggc    780

accactctca cagtctcctc agccaagccc accacgacgc cagcgccgcg accaccaaca    840

ccggcgccca ccatcgcgtc gcagcccctg tccctgcgcc cagaggcgtg ccggccagcg    900

gcgggggggcg cagtgcacac gagggggctg gacttcgcct gtgatatcta catctgggcg    960

cccttggccg ggacttgtgg ggtccttctc ctgtcactgg ttatcaccct ttactaa      1017
```

<210> SEQ ID NO 17
<211> LENGTH: 338
<212> TYPE: PRT
<213> ORGANISM: Homo sapiens
<220> FEATURE:
<221> NAME/KEY: MISC_FEATURE
<223> OTHER INFORMATION: Amino Acid sequence for mb-anti-CD3 scFv

<400> SEQUENCE: 17

```
Met Ala Leu Pro Val Thr Ala Leu Leu Leu Pro Leu Ala Leu Leu Leu
1               5                   10                  15

His Ala Ala Arg Pro Gln Ile Val Leu Thr Gln Ser Pro Ala Ile Met
            20                  25                  30

Ser Ala Ser Pro Gly Glu Lys Val Thr Met Thr Cys Ser Ala Ser Ser
        35                  40                  45

Ser Val Ser Tyr Met Asn Trp Tyr Gln Gln Lys Ser Gly Thr Ser Pro
    50                  55                  60

Lys Arg Trp Ile Tyr Asp Thr Ser Lys Leu Ala Ser Gly Val Pro Ala
65                  70                  75                  80

His Phe Arg Gly Ser Gly Ser Gly Thr Ser Tyr Ser Leu Thr Ile Ser
                85                  90                  95

Gly Met Glu Ala Glu Asp Ala Ala Thr Tyr Tyr Cys Gln Gln Trp Ser
            100                 105                 110

Ser Asn Pro Phe Thr Phe Gly Ser Gly Thr Lys Leu Glu Ile Asn Arg
        115                 120                 125

Gly Gly Gly Gly Ser Gly Gly Gly Gly Ser Gly Gly Gly Gly Ser Gly
    130                 135                 140

Gly Gly Gly Ser Glu Val Gln Leu Gln Gln Ser Gly Ala Glu Leu Ala
145                 150                 155                 160

Arg Pro Gly Ala Ser Val Lys Met Ser Cys Lys Ala Ser Gly Tyr Thr
                165                 170                 175

Phe Thr Arg Tyr Thr Met His Trp Val Lys Gln Arg Pro Gly Gln Gly
            180                 185                 190

Leu Glu Trp Ile Gly Tyr Ile Asn Pro Ser Arg Gly Tyr Thr Asn Tyr
        195                 200                 205

Asn Gln Lys Phe Lys Asp Lys Ala Thr Leu Thr Thr Asp Lys Ser Ser
    210                 215                 220

Ser Thr Ala Tyr Met Gln Leu Ser Ser Leu Thr Ser Glu Asp Ser Ala
225                 230                 235                 240

Val Tyr Tyr Cys Ala Arg Tyr Tyr Asp Asp His Tyr Cys Leu Asp Tyr
                245                 250                 255

Trp Gly Gln Gly Thr Thr Leu Thr Val Ser Ser Ala Lys Pro Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr
```

<210> SEQ ID NO 18
<211> LENGTH: 45
<212> TYPE: PRT
<213> ORGANISM: Homo sapiens
<220> FEATURE:
<221> NAME/KEY: MISC_FEATURE
<223> OTHER INFORMATION: Amino Acid sequence for CD8 alpha transmembrane domain

<400> SEQUENCE: 18

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 19
<211> LENGTH: 8
<212> TYPE: PRT
<213> ORGANISM: Homo sapiens
<220> FEATURE:
<221> NAME/KEY: MISC_FEATURE
<223> OTHER INFORMATION: Amino Acid sequence for FLAG tag

<400> SEQUENCE: 19

Asp Tyr Lys Asp Asp Asp Asp Lys
1               5


<210> SEQ ID NO 20
<211> LENGTH: 6
<212> TYPE: PRT
<213> ORGANISM: Homo sapiens
<220> FEATURE:
<221> NAME/KEY: MISC_FEATURE
<223> OTHER INFORMATION: Amino Acid sequence for His tag

<400> SEQUENCE: 20

His His His His His His
1               5


<210> SEQ ID NO 21
<211> LENGTH: 638
<212> TYPE: DNA
<213> ORGANISM: Homo sapiens
<220> FEATURE:
<221> NAME/KEY: misc_feature
<223> OTHER INFORMATION: Nucleic acid cloning construct for mbIL15

<400> SEQUENCE: 21

gaattcgccc ttccaccatg gccttaccag tgaccgcctt gctcctgccg ctggccttgc      60

tgctccacgc cgccaggccg aactgggtga atgtaataag tgatttgaaa aaaattgaag     120

atcttattca atctatgcat attgatgcta ctttatatac ggaaagtgat gttcacccca     180

gttgcaaagt aacagcaatg aagtgctttc tcttggagtt acaagttatt tcacttgagt     240

ccggagatgc aagtattcat gatacagtag aaaatctgat catcctagca aacaacagtt     300

tgtcttctaa tgggaatgta acagaatctg gatgcaaaga atgtgaggaa ctggaggaaa     360

aaaatattaa agaatttttg cagagttttg tacatattgt ccaaatgttc atcaacactt     420

ctaccacgac gccagcgccg cgaccaccaa caccggcgcc caccatcgcg tcgcagcccc     480

tgtccctgcg cccagaggcg tgccggccag cggcgggggg cgcagtgcac acgagggggc     540

tggacttcgc ctgtgatatc tacatctggg cgcccttggc cgggacttgt ggggtccttc     600

tcctgtcact ggttatcacc ctttactgct aactcgag                              638


<210> SEQ ID NO 22
<211> LENGTH: 788
<212> TYPE: DNA
<213> ORGANISM: Homo sapiens
<220> FEATURE:
<221> NAME/KEY: misc_feature
<223> OTHER INFORMATION: Nucleic acid cloning construct for 4-1BB ligand
```

<400> SEQUENCE: 22

```
gaattcgccc ttccaccatg gaatacgcct ctgacgcttc actggacccc gaagccccgt     60
ggcctcccgc gccccgcgct cgcgcctgcc gcgtactgcc ttgggccctg gtcgcggggc    120
tgctgctgct gctgctgctc gctgccgcct gcgccgtctt cctcgcctgc ccctgggccg    180
tgtccggggc tcgcgcctcg cccggctccg cggccagccc gagactccgc gagggtcccg    240
agctttcgcc cgacgatccc gccggcctct tggacctgcg gcagggcatg tttgcgcagc    300
tggtggccca aaatgttctg ctgatcgatg ggcccctgag ctggtacagt gacccaggcc    360
tggcaggcgt gtccctgacg gggggcctga gctacaaaga ggacacgaag gagctggtgg    420
tggccaaggc tggagtctac tatgtcttct ttcaactaga gctgcggcgc gtggtggccg    480
gcgagggctc aggctccgtt tcacttgcgc tgcacctgca gccactgcgc tctgctgctg    540
gggccgccgc cctggctttg accgtggacc tgccacccgc ctcctccgag gctcggaact    600
cggccttcgg tttccagggc cgcttgctgc acctgagtgc cggccagcgc ctgggcgtcc    660
atcttcacac tgaggccagg gcacgccatg cctggcagct tacccagggc gccacagtct    720
tgggactctt ccgggtgacc cccgaaatcc cagccggact cccttcaccg aggtcggaat    780
aactcgag                                                             788
```

<210> SEQ ID NO 23
<211> LENGTH: 889
<212> TYPE: DNA
<213> ORGANISM: Homo sapiens
<220> FEATURE:
<221> NAME/KEY: misc_feature
<223> OTHER INFORMATION: Nucleic acid cloning construct for mbIL12A

<400> SEQUENCE: 23

```
gaattcggct tccaccatgg ccttaccagt gaccgccttg ctcctgccgc tggccttgct     60
gctccacgcc gccaggccga gaaacctccc cgtggccact ccagacccag gaatgttccc    120
atgccttcac cactcccaaa acctgctgag ggccgtcagc aacatgctcc agaaggccag    180
acaaactcta gaattttacc cttgcacttc tgaagagatt gatcatgaag atatcacaaa    240
agataaaacc agcacagtgg aggcctgttt accattggaa ttaaccaaga atgagagttg    300
cctaaattcc agagagacct ctttcataac taatgggagt tgcctggcct ccagaaagac    360
ctcttttatg atggccctgt gccttagtag tatttatgaa gacttgaaga tgtaccaggt    420
ggagttcaag accatgaatg caaagcttct gatggatcct aagaggcaga tctttctaga    480
tcaaaacatg ctggcagtta ttgatgagct gatgcaggcc ctgaatttca acagtgagac    540
tgtgccacaa aaatcctccc ttgaagaacc ggatttttat aaaactaaaa tcaagctctg    600
catacttctt catgctttca ggattcgggc agtgactatt gatagagtga tgagctatct    660
gaatgcttcc aagcccacca cgacgccagc gccgcgacca ccaacaccgg cgcccaccat    720
cgcgtcgcag cccctgtccc tgcgcccaga ggcgtgccgg ccagcggcgg ggggcgcagt    780
gcacacgagg gggctggact tcgcctgtga tatctacatc tgggcgccct tggccgggac    840
ttgtggggtc cttctcctgt cactggttat caccctttac taactcgag                889
```

<210> SEQ ID NO 24
<211> LENGTH: 1216
<212> TYPE: DNA
<213> ORGANISM: Homo sapiens
<220> FEATURE:
<221> NAME/KEY: misc_feature
<223> OTHER INFORMATION: Nucleic acid cloning construct for mbIL12B

<400> SEQUENCE: 24

```
gaattcggct tccaccatgg ccttaccagt gaccgccttg ctcctgccgc tggccttgct     60
gctccacgcc gccaggccga tatgggaact gaagaaagat gtttatgtcg tagaattgga    120
ttggtatccg gatgcccctg gagaaatggt ggtcctcacc tgtgacaccc ctgaagaaga    180
tggtatcacc tggaccttgg accagagcag tgaggtctta ggctctggca aaaccctgac    240
catccaagtc aaagagtttg gagatgctgg ccagtacacc tgtcacaaag gaggcgaggt    300
tctaagccat tcgctcctgc tgcttcacaa aaaggaagat ggaatttggt ccactgatat    360
tttaaaggac cagaaagaac ccaaaaataa gacctttcta agatgcgagg ccaagaatta    420
ttctggacgt ttcacctgct ggtggctgac gacaatcagt actgatttga cattcagtgt    480
caaaagcagc agaggctctt ctgaccccca aggggtgacg tgcggagctg ctacactctc    540
tgcagagaga gtcagagggg acaacaagga gtatgagtac tcagtggagt gccaggagga    600
cagtgcctgc ccagctgctg aggagagtct gcccattgag gtcatggtgg atgccgttca    660
caagctcaag tatgaaaact acaccagcag cttcttcatc agggacatca tcaaacctga    720
cccacccaag aacttgcagc tgaagccatt aaagaactct cggcaggtgg aggtcagctg    780
ggagtaccct gacacctgga gtactccaca ttcctacttc tccctgacat tctgcgttca    840
ggtccagggc aagagcaaga gagaaaagaa agatagagtc ttcacggaca agacctcagc    900
cacggtcatc tgccgcaaaa atgccagcat tagcgtgcgg gcccaggacc gctactatag    960
ctcatcttgg agcgaatggg catctgtgcc ctgcagtaag cccaccacga cgccagcgcc   1020
gcgaccacca acaccggcgc ccaccatcgc gtcgcagccc ctgtccctgc gcccagaggc   1080
gtgccggcca gcggcggggg gcgcagtgca cacgaggggg ctggacttcg cctgtgatat   1140
ctacatctgg gcgcccttgg ccgggacttg tggggtcctt ctcctgtcac tggttatcac   1200
cctttactaa ctcgag                                                   1216
```

<210> SEQ ID NO 25
<211> LENGTH: 769
<212> TYPE: DNA
<213> ORGANISM: Homo sapiens
<220> FEATURE:
<221> NAME/KEY: misc_feature
<223> OTHER INFORMATION: Nucleic acid cloning construct for mbIL18

<400> SEQUENCE: 25

```
gaattcggct tccaccatgg ccttaccagt gaccgccttg ctcctgccgc tggccttgct     60
gctccacgcc gccaggccgt actttggcaa gcttgaatct aaattatcag tcataagaaa    120
tttgaatgac caagttctct tcattgacca aggaaatcgg cctctatttg aagatatgac    180
tgattctgac tgtagagata atgcaccccg gaccatattt attataagta tgtataaaga    240
tagccagcct agaggtatgg ctgtaactat ctctgtgaag tgtgagaaaa tttcaactct    300
ctcctgtgag aacaaaatta tttcctttaa ggaaatgaat cctcctgata acatcaagga    360
tacaaaaagt gacatcatat tctttcagag aagtgtccca ggacatgata ataagatgca    420
atttgaatct tcatcatacg aaggatactt tctagcttgt gaaaaagaga gagacctttt    480
taaactcatt ttgaaaaaag aggatgaatt gggggataga tctataatgt tcactgttca    540
aaacgaagac aagcccacca cgacgccagc gccgcgacca ccaacaccgg cgcccaccat    600
cgcgtcgcag cccctgtccc tgcgcccaga ggcgtgccgg ccagcggcgg ggggcgcagt    660
gcacacgagg gggctggact tcgcctgtga tatctacatc tgggcgccct tggccgggac    720
```

```
ttgtggggtc cttctcctgt cactggttat caccctttac taactcgag              769


<210> SEQ ID NO 26
<211> LENGTH: 1039
<212> TYPE: DNA
<213> ORGANISM: Homo sapiens
<220> FEATURE:
<221> NAME/KEY: misc_feature
<223> OTHER INFORMATION: Nucleic acid cloning construct for mb-anti CD3
      scFv

<400> SEQUENCE: 26

gaattcggct tccaccatgg ccttaccagt gaccgccttg ctcctgccgc tggccttgct     60

gctccacgcc gccaggccgc aaattgttct cacccagtct ccagcaatca tgtctgcatc    120

tccaggggag aaggtcacca tgacctgcag tgccagctca agtgtaagtt acatgaactg    180

gtaccagcag aagtcaggca cctcccccaa aagatggatt tatgacacat ccaaactggc    240

ttctggagtc cctgctcact tcaggggcag tgggtctggg acctcttact ctctcacaat    300

cagcggcatg gaggctgaag atgctgccac ttattactgc cagcagtgga gtagtaaccc    360

attcacgttc ggctcgggga caaagttgga aataaaccgg ggtggtggtg gttctggtgg    420

tggtggttct ggcggcggcg gctccggtgg tggtggatcc gaggtccagc tgcagcagtc    480

tggggctgaa ctggcaagac ctggggcctc agtgaagatg tcctgcaagg cttctggcta    540

cacctttact aggtacacga tgcactgggt aaaacagagg cctggacagg gtctggaatg    600

gattggatac attaatccta gccgtggtta tactaattac aatcagaagt tcaaggacaa    660

ggccacattg actacagaca aatcctccag cacagcctac atgcaactga gcagcctgac    720

atctgaggac tctgcagtct attactgtgc aagatattat gatgatcatt actgccttga    780

ctactggggc caaggcacca ctctcacagt ctcctcagcc aagcccacca cgacgccagc    840

gccgcgacca ccaacaccgg cgcccaccat cgcgtcgcag cccctgtccc tgcgcccaga    900

ggcgtgccgg ccagcggcgg ggggcgcagt gcacacgagg gggctggact tcgcctgtga    960

tatctacatc tgggcgccct tggccgggac ttgtggggtc cttctcctgt cactggttat   1020

caccctttac taactcgag                                                1039
```

STIMULATORY CELL LINES FOR EX VIVO EXPANSION AND ACTIVATION OF NATURAL KILLER CELLS

RELATED APPLICATIONS

This application is the U.S. National Stage of International Application No. PCT/SG2018/050138, filed Mar. 27, 2018, which designates the U.S., published in English, and claims the benefit of U.S. Provisional Application No. 62/477,311, filed Mar. 27, 2017, The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 44591145002SEQUENCELISTING.txt; created Sep. 25, 2019, 41 KB in size.

BACKGROUND

The emergence and persistence of many diseases are characterized by an insufficient immune response to aberrant cells, including malignant and virally infected cells. Immunotherapy is the use and manipulation of the patient's immune system for treatment of various diseases.

SUMMARY

Immunotherapy presents a new technological advancement in the treatment of disease, wherein immune cells are engineered to express certain targeting and/or effector molecules that specifically identify and react to diseased or damaged cells. This represents a promising advance due, at least in part, to the potential for specifically targeting diseased or damaged cells, as opposed to more traditional approaches, such as chemotherapy, where all cells are impacted, and the desired outcome is that sufficient healthy cells survive to allow the patient to live Immunotherapy approaches employing the adoptive transfer of Natural Killer (NK) cells to patients are presently in development. However, such treatments require large numbers of ex vivo pure NK cells suitable for genetic manipulation and clinical applications. Methods and compositions (and uses thereof) are disclosed herein for the ex vivo expansion and activation of NK cells from a mixed cell culture.

A variety of engineered cell types, DNA constructs, and methods for expanding and activating NK cells are provided for herein. For example, in several embodiments, there is provided a genetically engineered cell population that does not express major histocompatibility complex (MHC) I molecules, wherein co-culture of said engineered cell population with a population of immune cells results in the activation and expansion of at least one subpopulation of immune cells. In several embodiments, the engineered cell population is derived from a cell line that is immortal. For example, a cell line that exhibits one or more characteristics of an immortal cell while in culture. In several embodiments, the engineered cell population is derived from a cell line that is naturally immortal (e.g. stem cell lines). In several embodiments, the engineered cell population is derived from an immortalized (e.g., cancerous cell) line. In some embodiments, the engineered cell population is derived from cells that have been immortalized through engineering (e.g. genetically engineered to alter telomerase expression). In some embodiments, the engineered cell population is derived from a cancerous cell. In several embodiments, the engineered cell population is modified to express one or more membrane-bound factors that facilitate and/or enhance either activation and/or expansion of NK cells. For example, in several embodiments, the engineered cells express membrane-bound interleukin-15 (mbIL15). In still additional embodiments, the engineered cell population is modified to express membrane-bound 4-1BB ligand (4-1BBL), either in addition to, or in place of mbIL15. In further embodiments, the engineered cell population is modified to express at least one additional membrane bound interleukin that stimulates immune cell activation, in addition to, or in place of mbIL15, 4-1BBL, and/or other activating/expansion promoting factors.

In some embodiments, the engineered cell population comprises at least a first plurality of cells that expresses mbIL15 and a second plurality of cells that expresses 4-1BBL, such that the population as a whole expresses both mbIL15 and 4-1BBL. In other embodiments, the engineered cell population comprises a plurality of cells that expresses both mbIL15 and 4-1BBL. In yet other embodiments, the engineered cell population comprises some cells that express mbIL15, some cells that express 4-1BBL, and some cells that express both. In some embodiments, other ligands and/or activation factors may be additionally expressed in addition to or in lieu of mbIL15 and/or 4-1BBL.

In several embodiments, the mbIL15 expressed by the engineered cell population is encoded by a nucleic acid sequence that comprises SEQ ID NO. 1. In several embodiments, the 4-1BBL expressed by the engineered cell population is encoded by a nucleic acid sequence that comprises SEQ ID NO. 13.

Depending on the embodiment, each of the membrane bound molecules is coupled to a transmembrane domain. In several embodiments, the transmembrane domain of human CD8α is used to link the molecules to the membrane. In several embodiments, the transmembrane domain of human CD8α comprises the sequence of SEQ ID NO. 18. Other transmembrane domains are also used, depending on the embodiment, for example, other receptor or signaling domains (optionally truncated) known to reside in or across a cellular membrane may be used.

In several embodiments, the engineered cell population is derived from a cell line selected from the group consisting of K562 cells, Wilms tumor cell line HFWT, endometrial tumor cell line HHUA, melanoma cell line HMV-II, hepatoblastoma cell line HuH-6, lung small cell carcinoma cell lines Lu-130 or Lu-134-A, neuroblastoma cell lines NB19 or NB69, embryonal carcinoma testis cell line NEC14, cervical carcinoma cell line TCO-2, and neuroblastoma cell line TNB1. In several embodiments, the overall population is derived from two or more of the cell lines above (or others) and combined to yield a cell population that enables unexpectedly enhanced activation/expansion of immune cells, such as NK cells.

In several embodiments, the engineered cell population lacks expression of MHC II molecules. In several embodiments, the engineered cell population is derived from K562 cells.

Depending on the embodiment, an engineered cell population as disclosed herein expresses one or more interleukin molecules. In several embodiments, the interleukin comprises IL12A, or a fragment thereof. In several embodiments, the IL12A comprises the sequence of SEQ ID NO. 4 (or fragment thereof). In one embodiment, the interleukin comprises IL12B, or a fragment thereof. In one embodiment, the IL12B comprises the sequence of SEQ ID NO. 6 (or fragment thereof). In several embodiments, the interleukin comprises IL12A and IL12B, or fragments thereof. In such embodiments, the IL12A and IL12B can be oriented in the polynucleotide in an A-B, B-A, A-B-A-B, A-B-B-A, B-A-A-B orientation in either duplicate, triplicate, or larger repeats.

In several embodiments, the engineered cell population further expresses membrane bound IL18 (mbIL18), or fragment thereof. In several embodiments, the IL18 comprises the sequence of SEQ ID NO. 8. In still further embodiments, the engineered cell population further expresses membrane bound IL21 (mbIL21), or fragment thereof. In one embodiment, the IL21 comprises the sequence of SEQ ID NO. 10, or a fragment thereof.

In several embodiments, the cells express membrane bound IL22 (mbIL22), or fragment thereof. In one embodiment, the IL22 comprises the sequence of SEQ ID NO. 12, or a fragment thereof. As discussed above, combinations of various interleukins can be expressed, in a variety of combinations, repeats, triplets, etc. In several embodiments, such repeated patterns of expression in the polynucleotides yield unexpectedly enhanced activation and/or expansion of NK cells.

In several embodiments, the engineered cells may further comprise a membrane bound anti-CD3 antibody (mbα-CD3), an antibody fragment thereof, or scFv. In one embodiment, the mbα-CD3 is a monoclonal antibody. In several such embodiments, the mbα-CD3 targets an epitope within the nucleic acid sequence of CD3 epsilon of SEQ ID NO. 15. In additional embodiments, the mbα-CD3 is a scFv. In one embodiment, the scFv comprises the sequence of SEQ ID NO. 17.

Also provided for herein, as discussed in more detail below, are methods for expanding immune cells, the methods comprising co-culturing a blood sample comprising immune cells with any of the engineered cell populations disclosed herein. In several embodiments, the immune cells are Natural Killer (NK) cells.

According to several embodiments, there is provided a genetically engineered cell population derived from a cancerous cell, wherein the engineered cell population is modified to express one, two, or more of: membrane-bound interleukin-15 (mbIL15), membrane-bound 4-1BB ligand (4-1BBL), and at least one additional membrane bound interleukin that stimulates immune cell activation, and wherein co-culture of the engineered cell population with a population of immune cells results in the activation and expansion of at least one subpopulation of immune cells. In several embodiments, the genetically engineered cell population does not express major histocompatibility complex (MHC) I molecules.

Also provided for in several embodiments is a genetically engineered cell population that does not express major histocompatibility complex (MHC) I molecules, the engineered cell population being derived from a cancerous cell, engineered cell population being modified to express mblL15, 4-1BBL, a membrane-bound anti-CD3 antibody (mbα-CD3) that stimulates immune cell activation, and wherein co-culture of the engineered cell population with a population of immune cells results in the activation and expansion of at least one subpopulation of immune cells.

In several embodiments, the engineered cells are modified to express an additional membrane-bound interleukin that comprises IL12A, or a fragment thereof. In one embodiment, the membrane bound IL12A comprises the sequence of SEQ ID NO. 4. In one embodiment, the membrane bound IL12A has the sequence of SEQ ID NO. 4. In several embodiments, the additional membrane-bound interleukin comprises IL12B, or a fragment thereof. In one embodiment, the membrane bound IL12B comprises the sequence of SEQ ID NO. 6. In one embodiment, the membrane bound IL12B has the sequence of SEQ ID NO. 6. In several embodiments, the additional membrane bound interleukin comprises membrane bound IL12A and membrane bound IL12B or fragments thereof of either. Additionally, any of such embodiments of engineered cells can further comprise expression of membrane bound IL18 (mbIL18), or a fragment thereof. In one embodiment, the membrane bound IL18 comprises the sequence of SEQ ID NO. 8. In one embodiment, the membrane bound IL18 has the sequence of SEQ ID NO. 8.

In still additional embodiments, the engineered cells express membrane bound IL21 (mbIL21), or a fragment thereof. In several embodiments, the membrane bound IL21 has the sequence of SEQ ID NO. 10, or a fragment thereof. Either in combination with IL21, or alone, several embodiments provide for engineered cells that express membrane bound IL22 (mbIL22), or a fragment thereof. In several embodiments, the membrane bound IL22 has the sequence of SEQ ID NO. 12, or a fragment thereof.

Additionally, several embodiments provide for engineered cells that express a membrane bound anti-CD3 antibody (mbα-CD3), an antibody fragment or a single chain fragment variable (scFv) construct thereof. In one embodiment, the mbα-CD3 is a monoclonal antibody. In several embodiments, the mbα-CD3 targets an epitope within the nucleic acid sequence of CD3 portion of a T cell receptor. For example, in one embodiment one or more of the delta, epsilon or gamma subunit of the CD3 receptor is targeted by the membrane bound anti-CD3 antibody. In one embodiment, the CD3 receptor epsilon subunit of SEQ ID NO. 15 is targeted by the membrane bound antibody expressed on the engineered cells. In several embodiments the mbα-CD3 is a scFv. In one embodiment, the scFv comprises, consists essentially of or consists of the sequence of SEQ ID NO. 17. In one embodiment, the scFv has the sequence of SEQ ID NO. 17.

Additionally, in several embodiments, there is provided a stimulatory cell that is engineered to express the alpha subunit of the IL15 receptor with a high affinity for IL15, allowing it to engulf and present soluble IL15 on the surface of the cell. Combinations of any of the additional interleukins or antibodies can also be used, depending on the embodiment, to essentially allow for modular engineering of a stimulatory cell that provides for unexpectedly superior expansion and activation of NK cells.

In several embodiments, the engineered cell population is derived from a cell line including, but not limited to, the following: K562 cells, Wilms tumor cell line HFWT), endometrial tumor cell line HHUA, melanoma cell line HMV-II, hepatoblastoma cell line HuH-6, lung small cell carcinoma cell lines Lu-130 or Lu-134-A, neuroblastoma cell lines NB19 or NB69, embryonal carcinoma testis cell line NEC14, cervical carcinoma cell line TCO-2, and neuroblastoma cell line TNB1. In several embodiments, the engineered cells lack expression of MHC II molecules. In several embodiments, the engineered cells are derived from K562 cells.

Depending on the embodiment, the membrane bound molecule is imparted with the ability to be bound to the cell surface by being coupled to a transmembrane domain. The term "transmembrane" shall be given its ordinary meaning and shall refer to at least a portion of a polypeptide (e.g., domain) that is embedded in a cell membrane. In additional embodiments, at least one of the membrane bound molecules can be coupled to a single transmembrane domain. Additionally, in several embodiments, multiple types or multiple copies of the membrane bound molecules can be coupled to a transmembrane domain. Additionally, in several embodiments, multiple types or multiple copies of transmembrane domains can be coupled to the membrane bound molecules. In several embodiments, the membrane bound molecule is coupled to a transmembrane domain of human CD8α. In several embodiments, the transmembrane domain of human CD8α comprises the sequence of SEQ ID NO. 18. In several embodiments, the transmembrane domain of human CD8α has the sequence of SEQ ID NO. 18. In several embodiments, the mbIL15 is encoded by the nucleic acid of SEQ ID NO. 1. In several embodiments, the mb4-1BBL is encoded by the nucleic acid of SEQ ID NO. 13. In several embodiments, the mbIL15 is encoded by a nucleic acid sequence that comprises, consists essentially of or consists of the sequence of SEQ ID NO. 1. In several embodiments, the mb4-1BBL is encoded by a nucleic acid sequence that comprises, consists essentially of or consists the sequence of SEQ ID NO. 13.

In several embodiments, the engineered cell populations provided for herein are suitable for the expansion and/or activation of immune cells. "Expansion" of cells, as used herein, is given its ordinary meaning, and refers to increase in the number of a characteristic cell type, or cell types, from an initial population of cells, which may or may not be identical. The initial cells used for expansion need not be the same as the cells generated from expansion. For instance, the expanded cells may be produced by growth and differentiation of the initial engineered cell population. "Activation" of immune cells, as used herein, refers to the ability of immune cells to respond and exhibit, on a measurable level, an immune function of the corresponding cell known to a person of skill in the art. Methods to measure the activity of immune cells are also known to a person of skill in the art. "Immune cells" as used herein, is given its ordinary meaning and includes any cells of the immune system that may be assayed, including, but not limited to, B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types. In several embodiments, the expanded and/or activated immune cells are NK cells. As used herein, the term "Natural Killer Cells" ("NK cells") is given its ordinary meaning and refers to a type of cytotoxic lymphocyte of the immune system that provides rapid responses to virally infected cells and responds to transformed cells. Typically, immune cells detect peptides from pathogens presented by Major Histocompatibility Complex (MHC) molecules on the surface of infected cells, triggering cytokine release, causing lysis or apoptosis. NK cells are unique, however, as they have the ability to recognize stressed cells regardless of whether peptides from pathogens are present on MHC molecules. In some aspects, the NK cell is a mammalian NK cell. Examples of "mammalian" or "mammals" include primates (e.g., human), canines, felines, rodents, porcine, ruminants, and the like. Specific examples include humans, dogs, cats, horses, cows, sheep, goats, rabbits, guinea pigs, rats and mice. In a particular aspect, the mammalian NK cell is a human NK cell.

In several embodiments, the expansion and/or activation comprises co-culturing a blood sample, such as a peripheral blood sample, comprising NK cells with one of the engineered cell populations provided for herein.

In several embodiments, the engineered cell populations provided for herein can be prepared by a method comprising transducing the cells with a first construct encoding mbIL15, thereby generating a first transduced population of cells, expanding the first transduced population of cells, transducing the first transduced population of cells with a second construct encoding 4-1BBL, thereby generating a second transduced population of cells, transducing the second transduced population of cells with a third construct encoding at least one additional molecule capable of stimulating immune cells, thereby generating a third transduced population of cells, and expanding the third transduced population of cells. In several embodiments, the engineered cell populations provided for herein can be prepared by simultaneously transducing a population of cells with a first construct encoding mbIL15, a second construct encoding 4-1BBL, and a third construct encoding at least one additional molecule capable of stimulating immune cells. In still additional embodiments, the engineered cell populations provided for herein can be prepared by transducing a population of cells with a single construct encoding mbIL15, 4-1BBL, and at least one additional molecule capable of stimulating immune cells.

Additionally, in several embodiments, engineered cell populations can be prepared by a method comprising transducing the cells with a construct encoding mbIL15, 4-1BB, and one or more of mbIL12A, mbIL12B, mbIL18, mbIL21, mbIL22, and mbα-CD3 or fragments thereof.

Also provided for is a plurality of nucleic acids, for use in generating the engineered cell populations disclosed herein, comprising at least 3 from the group of nucleic acids comprising a nucleic acid encoding mbIL15, a nucleic acid encoding 4-1BBL, a nucleic acid encoding mbIL12A, a nucleic acid encoding mbIL12B, a nucleic acid encoding mbIL18, a nucleic acid encoding mbIL21, a nucleic acid encoding mbIL22, and a nucleic acid encoding mbα-CD3. In several embodiments, the plurality of nucleic acids is optionally configured as a single construct (e.g., encoded or operationally linked). In several embodiments, the plurality of nucleic acids is configured as part of more than one construct. In several embodiments, the mbIL15 is encoded by SEQ ID NO. 1. In several embodiments, the 4-1BBL is encoded by SEQ ID NO. 13. In several embodiments, the mbIL12A is encoded by SEQ ID NO. 3. In several embodiments, the mbIL12B is encoded by SEQ ID NO. 5. In several embodiments, the mbIL18 is encoded by SEQ ID NO. 7. In several embodiments, the mbIL21 is encoded by SEQ ID NO. 9 or a fragment thereof. In several embodiments, the mbIL22 is encoded by SEQ ID NO. 11 or a fragment thereof. In several embodiments, the mbα-CD3 is encoded by SEQ ID NO. 16. Depending on the embodiment, one or more of the plurality of nucleic acids optionally comprises a tag, such as a FLAG tag, a HIS tag, GFP, or other tags and/or markers known to a person of skill in the art.

Also provided for herein, in several embodiments, is a method for expanding NK cells, comprising obtaining a peripheral blood sample comprising a mixed population of immune cells comprising NK cells and T cells, contacting the mixed population of cells with an engineered cell population that exhibits reduced expression of MHC I and has been modified to express membrane-bound interleukin- 15 (mbIL15), 4-1BB ligand (4-1BBL), and at least one additional molecule that stimulates immune cell activation, and co-culturing the mixed population of cells with the engineered cells for a period of time sufficient to expand the NK cells of the mixed population. In several embodiments, the method optionally comprises adding IL2 to the media used in the co-culture. In several embodiments, the method optionally further comprises removing T cells from the mixed population either prior to or after co-culturing. Methods of removing and/or separating T cells from a mixed population of immune cells comprising NK cells and T cells are well known in the relevant art.

In one embodiment, there is provided a modified cell line comprising K562 myeloid leukemia cells that lack major histocompatibility complex I molecules that are genetically modified to express membrane-bound interleukin-15, 4-1BB ligand, and membrane-bound anti-CD3. The terms "genetically modified" and "genetically engineered" shall be given their ordinary meaning, shall be used interchangeably, and shall refer to use of use of biotechnology to manipulate one or more aspect of at least a portion of an organism's genome.

In one embodiment, there is provided a modified cell line comprising K562 myeloid leukemia cells that lack major histocompatibility complex I molecules that are genetically modified to express membrane-bound interleukin-15, membrane-bound 4-1BB ligand, and at least one additional membrane-bound interleukin. In several embodiments, the at least one additional membrane-bound interleukin is one or more of interleukin-12, interleukin-18, and a combination of interleukin-12 and interleukin-18. In several embodiments, the modified cells further comprise a membrane-bound anti-CD3 antibody. Combinations of these additional membrane bound signaling molecules are used in several embodiments. As used herein, the term "signaling molecules" shall be given its ordinary meaning and shall include, but not be limited to interleukins, CD3, 4-1BB, etc.

In one embodiment, there is provided a modified cell line comprising K562 myeloid leukemia cells that lack major histocompatibility complex I molecules that are genetically modified to express membrane-bound interleukin-15, 4-1BB ligand, membrane-bound anti-CD3 antibody, and at least one additional membrane-bound interleukin.

Also provided for herein is a population of NK cells expanded and/or activated by culturing a mixed cell culture comprising NK cells and T lymphocytes with any of the modified cell lines disclosed herein. Such a population of NK cells can be used for the treatment of cancer or infectious disease, and/or in the preparation of a medicament for such treatment. The engineered cell populations disclosed herein are suitable for use in the activation of NK cells, such activated NK cells for use in the treatment of cancer or infectious disease.

Methods for treating diseases using expanded and/or activated NK cells are also provided for herein. For example, in several embodiments, there is provided a method of treating cancer or an infectious disease comprising administering to a subject having cancer (e.g., a tumor, whether solid or suspension) or an infectious disease a composition comprising an expanded population of immune cells, the immune cells having been expanded by co-culturing the immune cells with an engineered cell population that has been modified to express membrane-bound interleukin-15 (mbIL15) and 4-1BB ligand (4-1BBL), and has been modified to express at least one additional membrane bound interleukin that stimulates immune cell activation. In several embodiments, the co-culturing results in the activation and expansion of at least one subpopulation of immune cells, and wherein the at least one subpopulation of immune cells is administered to the subject. In several embodiments, the engineered cell population is derived from a cancerous cell, e.g., an immortalized cell line. In several embodiments, the administered subpopulation of immune cells comprises NK cells.

BRIEF DESCRIPTION OF THE DRAWINGS

The descriptions of the figures below are related to experiments and results that represent non-limiting embodiments of the inventions disclosed herein.

FIG. 1A), membrane bound IL18 (mbIL18;

FIG. 1B), or combinations thereof (FIG. 1C). Also provided are constructs wherein cells (using K562 as an example) co-express 4-1BBL and mbIL15 in conjunction with combinations of cytokines (such as mbIL12A/12B and/or mbIL18, FIGS. 1D-1F) and antibodies (for example membrane bound anti-CD3 (mbantiCD3, FIG. 1G)).

FIG. 2A depicts expression of mbIL15, FIG. 2B depicts expression of 4-1BBL, FIG. 2C depicts expression of mbIL18, FIG. 2D depicts expression of mbIL12A, FIG. 2E depicts expression of mbIL12B, and FIG. 2F depicts expression of mb-anti-CD3.

FIG. 3A depicts data related to the percentage of NK cells recovered after 7 days of culture (with IL-2) with various K562 cell lines, relative to the number of peripheral blood mononucleated cells initially seeded. FIG. 3B depicts data related to the percentage of NK cells recovered after 7 days of culture with various K562 cell lines, relative to the number of PBMCs initially seeded (P value calculated by paired t test).

FIG. 4A depicts data related to the expansion of NK cells over time when co-cultured with the indicated K562 variant. PBMCs were co-cultured with irradiated K562 cells expressing mbIL15 and 4-1BBL (K562-mb15-41BBL) (FIG. 4A), or with K562-mb15-41BBL cells also expressing mbIL12 (+mb12) (FIG. 4B), mbIL18 (+mb18) (FIG. 4C), or both mbIL12 and mbIL18 (+mb12+mb18) (FIG. 4D). FIG. 4E depicts data related to the cytotoxicity of expanded NK cells against K562 cells at the indicated effector:target (E:T) ratios. FIG. 4F relates to the cytotoxicity of expanded NK cells against K562 cells at the indicated E:T ratios. Shown are means (±SD) of triplicate experiments. P value was calculated by paired t test.

DETAILED DESCRIPTION

Figures 1A, 1B, 1C, 1D, 1E, 1F, 1G:
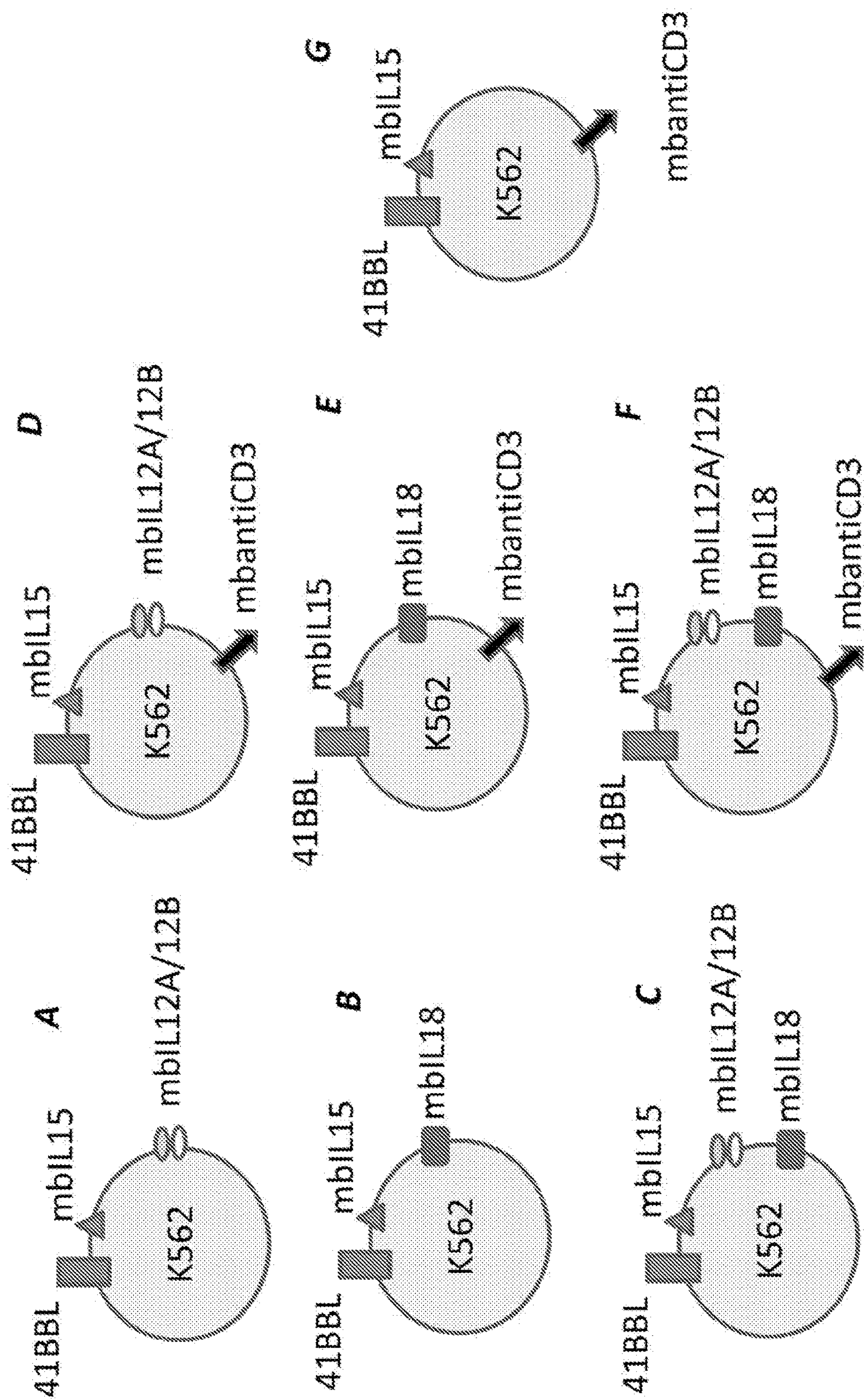
FIGS. 1A-1G represent non-limiting examples of engineered cells for use in expanding immune cells in accordance with several embodiments disclosed herein. Constructs are provided wherein a K562 cell (as an example) expresses a ligand for 4-1BB (4-1BBL) and membrane bound IL15 (mbIL15) in conjunction with other cytokines, such as membrane bound IL12A/12B (mbIL12A/12B.
Figures 2A, 2B, 2C, 2D, 2E, 2F:
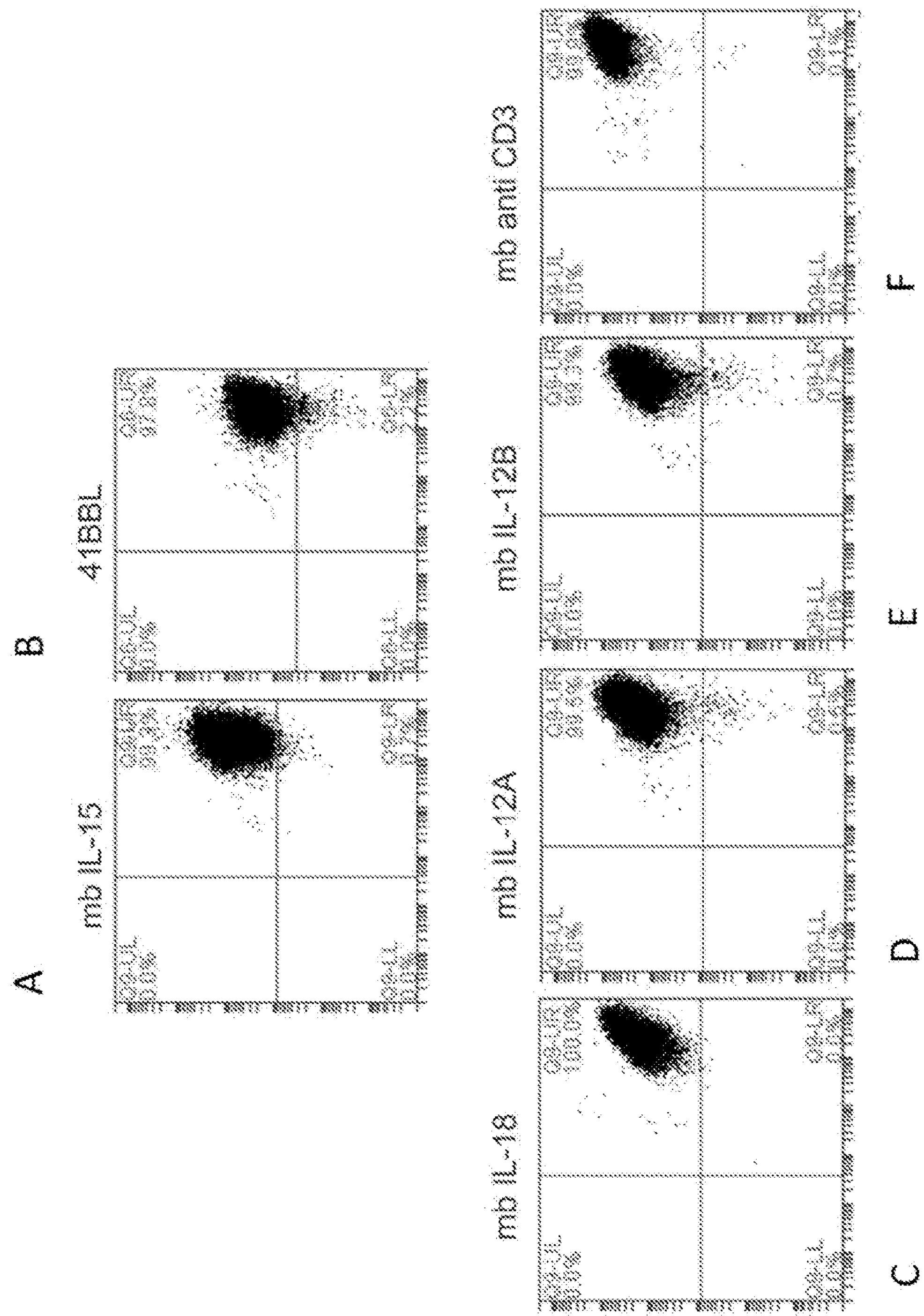
FIGS. 2A-2F depict flow cytometry measurements of expression of various genes by K562, according to several embodiments disclosed herein.

The emergence and persistence of aberrant cells (including virally infected and malignant cells) underlying many diseases are enabled by an insufficient immune response to said aberrant cells. A goal of immunotherapy is to initiate or augment the response of the patient's immune system, for example, to boost the ability of immune cells, such as Natural Killer (NK) cells to damage, kill, or otherwise inhibit damaged or diseased cells. Adoptive transfer of immune cells engineered to express certain targeting and/or effector molecules that specifically identify and react to diseased or damaged cells is a particularly promising immunotherapy approach. One variation of this approach involves administering T cells engineered to express chimeric receptors to patients to elicit targeted recognition and destruction of the aberrant cells of interest. However, a drawback of this approach is that it may favor the use of autologous cells (or MHC-compatible donor cells) to prevent the induction of graft-versus-host-disease in the patient. Further, retrieval and use of autologous T cells from cancer patients poses several potentially adverse issues. NK cells, however, are advantageous in that either autologous or donor-derived allogeneic cells can be employed, according to several embodiments disclosed herein. One challenge associated with NK cell based immunotherapy is obtaining adequately large and sufficiently pure (e.g., free of other cell types) quantities of NK cells for genetic manipulation and infusion, as NK cells represent a small fraction of the total cells in an immune cell population.

Thus, there remains a need for greater expansion of NK cells for use in NK cell-based immunotherapy. As such, in several embodiments, there are provided populations of expanded and activated NK cells derived from co-culturing the modified cell lines disclosed herein with a starting population of immune cells. In several embodiments, the starting population of immune cells comprises NK cells and T cells. In several embodiments, there is also provided a method for preferentially expanding NK cells in a mixed cell culture comprising NK cells and T cells, which comprises co-culturing said mixed cell culture with the modified cell lines disclosed herein. Depending on the embodiment, preferential expansion includes, but is not limited to, two-fold, three-fold, 5-fold, 10-fold, or greater, expansion of NK cells as compared to other immune cells. In additional embodiments, preferential expansion refers to NK cell expansion that is at least about 10%, about 20%, about 30%, about 50% or more than expansion of another immune cell type. There is also provided, in several embodiments, methods of using any of the modified cell lines disclosed herein for expanding NK cells in a mixed cell culture comprising NK cells and T cells.

Cells for Use in Immune Cell Expansion

In several embodiments, cell lines are used in a co-culture with a population of immune cells that are to be expanded. Such cell lines are referred to herein as "stimulatory cells," which can also be referred to as "feeder cells". In several embodiments, the entire population of immune cells is to be expanded, while in several embodiments, a selected immune cell subpopulation is preferentially expanded. For example, in several embodiments, NK cells are preferentially expanded relative to other immune cell subpopulations. While in some embodiments, stimulatory cells are wild type cells, in several embodiments, the stimulatory cells are genetically modified to render them particularly suitable for expanding and/or activating immune cells. As discussed in more detail below, various cell lines are amenable to genetic modification that can result in surface expression of certain molecules that stimulate NK activation. Certain cell lines are particularly amenable to expanding NK cells, for example, those that do not express MHC I molecules, which have an inhibitory effect on NK cells. In some embodiments, the cells need not entirely lack MHC I expression, however they may express MHC I molecules at a lower level than a wild type cell. For example, in several embodiments, if a wild type cell expresses an MHC at a level of X, the cell lines used may express MHC at a level less than 95% of X, less than 90% of X, less than 85% of X, less than 80% of X, less than 70% of X, less than 50% of X, less than 25% of X, and any expression level between (and including) those listed. In several embodiments, the stimulatory cells are immortalized, e.g., a cancer cell line. However, in several embodiments, the stimulatory cells are primary cells.

Cell types that lack, or have reduced, MHC I expression include, but are not limited to, K562 cells, certain Wilm's Tumor cell lines (for example Wilms tumor cell line HFWT), endometrial tumor cells (for example, HHUA), melanoma cells (e.g., HMV-II), hepatoblastoma cells (e.g., HuH-6), lung small cell carcinoma cells (e.g., Lu-130 and Lu-134-A), neuroblastoma cells (e.g., NB19 and NB69), embryonal carcinoma testis cells (e.g., NEC14), cervical carcinoma cells (TCO-2), neuroblastoma cells (e.g., TNB1), 721.221 EBV transformed B cell line, among others. In several embodiments, the stimulatory cells also have reduced (or lack) MHC II expression, as well as having reduced (or lacking) MHC I expression. In some embodiments, other cell lines that may initially express MHC class I molecules can be used, in conjunction with genetic modification of those cells to reduce or knock out MHC I expression. Genetic modification can be accomplished through the use of gene editing techniques (e.g. the crispr/cas-9 system), inhibitory RNA (e.g., siRNA), or other molecular methods to disrupt and/or reduce the expression of MHC I molecules on the surface of the cells. Additionally, or alternatively, other approaches to block binding or other interactions with the MHC I molecules can be used (e.g., blocking antibodies, interfering ligands, etc.).

In several embodiments, certain ratios of stimulatory cells to cells to be expanded/stimulated are used. For example, in several embodiments a stimulatory cell:"target" cell ratio of about 5:1 is used. In several embodiments, 1:1 ratios are used, while in additional embodiments, can range from about: 1:10, 1:20, 1:50, 1:100, 1:1,000, 1:10,000, 1:50,000, 1:100,000, 100,000:1, 50,000:1, 10,000:1, 1,000:1, 100:1, 50:1, 20:1, 10:1, and any ratio in between those listed, including endpoints. In some embodiments, combinations of cell types are used (e.g., K562 with one or more additional cell types), with the resultant activation and/or expansion of NK cells being greater than could be achieved with the use of any single cell type alone (e.g., as a result of synergy between the cell types). In some such embodiments, MHC I expression need not necessarily be reduced and/or absent in each of the cell lines used in combination. In some embodiments the relative frequency of one cell type versus the others in combination can be varied in order to maximize the expansion and activation of the desired immune cell population. For example, if two cell populations are used, the relative frequency can range from a ratio of 1:10, 1:20, 1:50, 1:100, 1:1,000, 1:10,000, 1:50,000, 1:100,000, 100,000:1, 50,000:1, 10,000:1, 1,000:1, 100:1, 50:1, 20:1, 10:1, and any ratio in between those listed, including endpoints.

As discussed in more detail below, certain stimulatory molecules (e.g. interleukins, CD3, 4-1BBL, etc.) can be expressed on or by the cells that promote immune cell expansion and activation (e.g., the stimulatory cells). However, in several embodiments, either in conjunction with, or in place of cells to promote immune cell expansion, a solid support is used. For example, a solid support is a surface that is capable of having a molecule attached to the surface, including, but not limited to, metal, glass, plastic, polymeric materials, particles (e.g., beads or microspheres), and/or lipids (either natural or synthetic). In some embodiments, compositions are used that can elute a stimulatory molecule, such as those disclosed herein, into the culture medium in order to facilitate the expansion of a desired immune cell population.

Stimulatory Molecules

As discussed briefly above, certain molecules promote the expansion of immune cells. Depending on the embodiment, the stimulatory molecule, or molecules, can be expressed on the surface of the stimulatory cells used to expand the immune population, while in some embodiments the stimulatory cells can be engineered to express and secrete one or more stimulatory molecules into the culture medium. In still additional embodiments, one or more stimulatory molecules are used to supplement the cell culture media. In some embodiments, the immune cell population is expanded relatively uniformly (e.g., no particular subpopulation is preferentially expanded). In some such embodiments, following expansion of all immune cell populations, desired subpopulations are selectively separated (e.g., NK cells are separated from T cells, or vice versa) for further use. In several embodiments, certain specific immune cell subpopulations, such as NK cells, are preferentially expanded.

In several embodiments, the general construct for engineering a stimulatory cell line to express a membrane bound molecule employs a signal peptide that ultimately drives expression of the membrane bound molecule, the nucleic acid sequence that encodes the membrane bound molecule, an optional linker, and a transmembrane domain. This general construct can vary with the embodiment based on, at least in part, the complexity, size or ability to express a given membrane bound molecule.

In some embodiments interleukin 15 (IL15) is used to facilitate expansion of NK cells. In some embodiments, the IL15 is membrane bound on the stimulatory cells (referred to herein as "mbIL15"). In some embodiments, IL15 is membrane bound by virtue of being coupled or conjugated to a transmembrane molecule or integral membrane protein. In several embodiments, a transmembrane domain of CD8α is used (SEQ ID NO. 18). In several embodiments, wild type (e.g., a full-length) IL15 is expressed on, or by, the stimulatory cells. In some embodiments, the IL15 is at least 70%, at least 75%, at least 80%, at least 85%, at least 90%, at least 95% homologous with full-length IL15. In some embodiments, truncated forms of IL15 are used. In several embodiments, mbIL15 is encoded by the nucleic acid sequence of SEQ ID NO: 1. In several embodiments, mbIL15 is encoded by the amino acid sequence of SEQ ID NO: 2. In several embodiments, the stimulatory molecule may have one or more additional mutations from SEQ ID NO. 1 or 2, but retains, or in some embodiments, has enhanced stimulatory activity.

In several embodiments, the stimulatory cells are engineered to express all, or a portion of the IL15 receptor. In several embodiments, the portion of the IL15 receptor is a functional portion of the IL15 receptor. For example, in some embodiments, the stimulatory cells are engineered to express the IL15 receptor alpha subunit. In several embodiments, the cells produce, or are engineered to produce (e.g., secrete) soluble IL15. The soluble IL15 can thereby bind its receptor expressed by the stimulatory cells and subsequently be internalized (e.g., endocytosed) and presented to another cell. In essence, in some embodiments, rather than engineering the stimulatory cells to express an engineered mbIL15, the stimulatory cells could be engineered to express the IL15 receptor alpha subunit, which can bind IL15 (even in the absence of the remaining IL15 receptor CD122 and CD132 subunits), and present it on the cell surface, thus resulting in IL15 expression in an alternative way to mbIL15.

In some embodiments, interleukin 12A (IL12A) and/or 12B (IL12B) is used to facilitate expansion of NK cells. In some embodiments, the IL12 is membrane bound on the stimulatory cells (referred to herein as "mbIL12"). In some embodiments combinations of IL12A and IL12B are used (referred to herein as "IL12A/12B", and when membrane bound, "mbIL12A/12B"). In some embodiments, IL15 is membrane bound by virtue of being coupled or conjugated to a transmembrane molecule or integral membrane protein. In several embodiments, a transmembrane domain of CD8α is used. In several embodiments, wild type (e.g., a full-length) IL12A and/or 12B is expressed on, or by, the stimulatory cells. In some embodiments, IL12A and/or 12B is at least 70%, at least 75%, at least 80%, at least 85%, at least 90%, at least 95% homologous with full-length IL12A or 12B, respectively. In some embodiments, truncated forms of IL12A and/or 12B are used. In several embodiments, mbIL12A is encoded by the nucleic acid sequence of SEQ ID NO: 3. In several embodiments, mbIL12A is encoded by the amino acid sequence of SEQ ID NO: 4. In several embodiments, the stimulatory molecule may have one or more additional mutations from SEQ ID NO. 3 or 4, but retains, or in some embodiments, has enhanced stimulatory activity. In several embodiments, mbIL12B is encoded by the nucleic acid sequence of SEQ ID NO: 5. In several embodiments, mbIL12B is encoded by the amino acid sequence of SEQ ID NO: 6. In several embodiments, the stimulatory molecule may have one or more additional mutations from SEQ ID NO. 5 or 6, but retains, or in some embodiments, has enhanced stimulatory activity. In some embodiments, a mixture of IL12A and IL12B is used. In several embodiments, a particular ratio of expression of IL12A:IL12B is used, for example, 1:10, 1:100, 1:1000, 1:10,000, 10,000:1, 1000:1, 100:1, 10:1 and any ratio there between, including endpoint. In some embodiments both IL12A and IL12B are expressed, for example, as a fusion protein. In some embodiments, a fragment, or fragments, of IL12A are expressed in conjunction with a fragment, or fragments of IL12B. In several embodiments, expression of IL12 (A and/or B) on the stimulatory cells imparts to the cells the ability to influence the phenotype and function of the expanded cells. In other words, expression of IL12A and/or B (alone or in combination with the other stimulatory molecules disclosed herein, leads to, in several embodiments, selective expansion of an NK cell sub-population. In several embodiments, that particular subpopulation can be advantageous in a specific therapeutic application where a particular phenotype of NK cells is particularly effective.

In some embodiments interleukin 18 (IL18) is used to facilitate expansion of NK cells. In some embodiments, the IL18 is membrane bound on the stimulatory cells (referred to herein as "mbIL18"). In some embodiments, IL18 is membrane bound by virtue of being coupled or conjugated to a transmembrane molecule or integral membrane protein. In several embodiments, a transmembrane domain of CD8α is used. In several embodiments, wild type (e.g., a full-length) IL18 is expressed on, or by, the stimulatory cells. In some embodiments, the IL18 is at least 70%, at least 75%, at least 80%, at least 85%, at least 90%, at least 95% homologous with full-length IL18. In some embodiments, truncated forms of IL18 are used. In several embodiments, mbIL18 is encoded by the nucleic acid sequence of SEQ ID NO: 7. In several embodiments, mbIL18 is encoded by the amino acid sequence of SEQ ID NO: 8. In several embodiments, the stimulatory molecule may have one or more additional mutations from SEQ ID NO. 7 or 8, but retains, or in some embodiments, has enhanced stimulatory activity. In several embodiments, expression of IL18 on the stimulatory cells imparts to the cells the ability to influence the phenotype and function of the expanded cells. In other words, expression of IL18 (alone or in combination with the other stimulatory molecules disclosed herein, leads to, in several embodiments, selective expansion of an NK cell sub-population. In several embodiments, that particular sub-population can be advantageous in a specific therapeutic application where a particular phenotype of NK cells is particularly effective.

In some embodiments interleukin 21 (IL21) is used to facilitate expansion of NK cells. In some embodiments, the IL21 is membrane bound on the stimulatory cells (referred to herein as "mbIL21"). In some embodiments, IL21 is membrane bound by virtue of being coupled or conjugated to a transmembrane molecule or integral membrane protein. In several embodiments, a transmembrane domain of CD8α is used. In several embodiments, wild type (e.g., a full-length) IL21 is expressed on, or by, the stimulatory cells. In some embodiments, the IL21 is at least 70%, at least 75%, at least 80%, at least 85%, at least 90%, at least 95% homologous with full-length IL21. In some embodiments, truncated forms of IL21 are used. In several embodiments, the mbIL21 used to stimulate NK cells is derived from the nucleic acid sequence of SEQ ID NO: 9. As discussed herein, in several embodiments, the CD8α transmembrane domain is used to anchor the IL21 of SEQ ID NO: 9 (or fragment thereof) to the membrane of the stimulatory cells. In several embodiments, the mbIL21 used to stimulate NK cells is derived from the amino acid sequence of SEQ ID NO: 10. In several embodiments, the stimulatory molecule may have one or more additional mutations from SEQ ID NO. 9 or 10, but retains, or in some embodiments, has enhanced stimulatory activity.

In some embodiments interleukin 22 (IL22) is used to facilitate expansion of NK cells. In some embodiments, the IL22 is membrane bound on the stimulatory cells (referred to herein as "mbIL22"). In some embodiments, IL22 is membrane bound by virtue of being coupled or conjugated to a transmembrane molecule or integral membrane protein. In several embodiments, a transmembrane domain of CD8α is used. In several embodiments, wild type (e.g., a full-length) IL22 is expressed on, or by, the stimulatory cells. In some embodiments, the IL22 is at least 70%, at least 75%, at least 80%, at least 85%, at least 90%, at least 95% homologous with full-length IL22. In some embodiments, truncated forms of IL22 are used. In several embodiments, mbIL22 is encoded by the nucleic acid sequence of SEQ ID NO: 11. In several embodiments, mbIL22 is encoded by the amino acid sequence of SEQ ID NO: 12. In several embodiments, the stimulatory molecule may have one or more additional mutations from SEQ ID NO. 11 or 12, but retains, or in some embodiments, has enhanced stimulatory activity.

In some embodiments 4-1BB ligand (4-1BBL) is used to facilitate expansion of immune cells. 4-1BBL has an extracellular domain that interacts with its receptor on T cells, 4-1BB, thereby providing the T cells co-stimulatory signals for survival, proliferation, and differentiation. In some embodiments, 4-1BBL is membrane bound by virtue of being coupled or conjugated to a transmembrane molecule or an integral membrane protein. In several embodiments, wild type (e.g., a full-length) 4-1BBL is expressed on, or by, the stimulatory cells. In some embodiments, the 4-1BBL is at least 70%, at least 75%, at least 80%, at least 85%, at least 90%, at least 95% homologous with full-length 4-1BBL. In some embodiments, truncated forms of IL18 are used. In several embodiments, mb4-1BBL is encoded by the nucleic acid sequence of SEQ ID NO: 13. In several embodiments, mb4-1BBL is encoded by the amino acid sequence of SEQ ID NO: 14. In several embodiments, the stimulatory molecule may have one or more additional mutations from SEQ ID NO. 13 or 14, but retains, or in some embodiments, has enhanced stimulatory activity.

In some embodiments, an anti-CD3 antibody is used to facilitate expansion of immune cells. In some embodiments, the anti-CD3 antibody is membrane bound on the stimulatory cells (referred to herein as "mbantiCD3" or "mba-CD3"). In several embodiments, a full-length anti-CD3 antibody is expressed on the stimulatory cells. In some embodiments, the anti-CD3 antibody comprises a single chain fragment variable region (scFv) fragment. Depending on the embodiment, the antibody can be monoclonal or polyclonal. In some embodiments, the anti-CD3 antibody comprises a variety of antigenic fragments and/or fusions selected from a Fab', a F(ab')2, a single domain antibody (e.g., a diabody, a nanobody). In some embodiments, the antibody is selected from the group consisting of muromonab-CD3, otelixizumab, teplizumab and visilizumab. In some embodiments, the antibody is at least 70%, at least 75%, at least 80%, at least 85%, at least 90%, at least 95% homologous with one or more of muromonab-CD3, otelixizumab, teplizumab and visilizumab. In several embodiments, antibodies that bind to one or more subunits of the CD3 portion of the T cell receptor are expressed by the stimulatory cells. In several embodiments, the antibodies expressed are directed against the gamma, epsilon, or delta CD3 subunits. In several embodiments, the antibody expressed by the stimulatory cells are directed against an epitope derived from the CD3 epsilon nucleic acid sequence of SEQ ID NO: 15. In several embodiments, the anti-CD3 antibody is a single chain fragment variable (scFv). In several embodiments, mbantiCD3 scFv is encoded by the nucleic acid sequence of SEQ ID NO: 16. In some such embodiments, the antibody has the amino acid sequence of SEQ ID NO: 17. In several embodiments, the stimulatory molecule may have one or more additional mutations from SEQ ID NO. 16 or 17, but retains, or in some embodiments, has enhanced stimulatory activity In several embodiments, stimulatory cells, such as K562 cells, are genetically modified to express combinations of various stimulatory molecules. Depending on the embodiment, any combination of the stimulatory molecules disclosed herein may be used. For example, in several embodiments, mbIL15, 4-1BBL and mbα-CD3 are co-expressed on the stimulatory cells. In several embodiments, mbIL15, 4-1BBL and mbIL12A/12B are co-expressed on the stimulatory cells. In several embodiments, mbIL15, 4-1BBL and mbIL18 are co-expressed on the stimulatory cells. In several embodiments, mbIL15, 4-1BBL, mbIL18, and mbIL12A/12B are co-expressed on the stimulatory cells. In several embodiments, mbIL15, 4-1BBL, mbIL12A/12B and mbantiCD3 are co-expressed on the stimulatory cells. In several embodiments, mbIL15, 4-1BBL, mbIL18 and mbantiCD3 are co-expressed on the stimulatory cells. In several embodiments, mbIL15, 4-1BBL, mbIL12A/12B, mbIL18 and mbantiCD3 are co-expressed on the stimulatory cells. In some embodiments, mbIL21 and/or mbIL22 can be expressed in addition to, or in place of, any of the stimulatory molecules listed above. In some embodiments, each of these molecules is expressed in the stimulatory cells through transfection with individual plasmids. Alternatively, two or more of the stimulatory molecules can be encoded in a single plasmid.

Depending on the embodiment, and on the stimulatory molecule in question, the stimulatory molecules may be expressed at particular times during the process of co-culturing with an immune cell population. For example, rather than being constitutively expressed, one or more of the markers may be under the control of an inducible, or otherwise regulatable promoter. As such, a triggering molecule or stimulus can be added to the co-culture at a desired time, resulting in the expression of the desired stimulatory molecule at a particular point during the expansion and activation protocol. As used herein, the terms "inducible promotor" and "regulatable promotor" shall be given their ordinary meaning and shall also refer to promotors whose transcriptional activity is modulated (e.g., stimulated or inhibited) by the presence of certain biotic or abiotic factors. As used herein, the terms "triggering molecule" or "triggering stimulus" shall be given their ordinary meaning and shall refer to chemical or physical substances or conditions that act on an inducible or regulatable promotor, including but not limited to alcohol, tetracycline, steroids, metal and other compounds, as well as high or low culture temperatures. Additionally, regulatable expression of the stimulatory molecules can also be used to reduce and/or eliminate expression of a particular stimulatory molecule during the culturing process. Such embodiments can facilitate the preferential expansion of certain subpopulations of immune cells, such as NK cells, by for example providing a particular stimulatory signal at a point in time during the activation and expansion process when the NK cells are particularly sensitive to such a signal. In several embodiments, such an approach can lead to an unexpectedly robust activation and expansion of NK cells. In still additional embodiments, the duration of proliferation of the NK cells is extended, ultimately leading to a larger population of activated NK cells for use in, for example, cancer immunotherapy.

In some embodiments, also provided herein are nucleic acid and amino acid sequences that have homology of at least 80%, 85%, 90%, 95%, 96%, 97%, 98%, 99% (and ranges therein) as compared with the respective nucleic acid or amino acid sequences of the stimulatory molecules disclosed herein, encoded by SEQ ID NOS. 1-17 and that also exhibit one or more of the functions as compared with the respective SEQ ID Nos. 1-17 including but not limited to, (i) activating NK cells, (ii) sensitizing NK cells, (iii) enhanced NK cell proliferation, (iv), enhanced NK cell target affinity, (v) upregulated or otherwise enhanced signal transduction, (vi) enhanced NK cell cytotoxicity, (vii) T cell stimulation (e.g. proliferation, selective expansion of useful subpopulations, etc.), (viii) selective expansion of particular NK cell sub-populations, and (ix) combinations thereof.

Methods of Co-culture and Immune Cell Expansion

In several embodiments, stimulatory cells can be transduced with multiple constructs (each encoding one or more of the stimulatory molecules to be expressed), or alternatively, single constructs can be used. In several embodiments, the stimulatory cells are first transduced with a stimulatory molecule coupled to an identifiable marker, such as a fluorescent tag (e.g., green fluorescent protein, GFP, or other fluorescent moiety). In additional embodiments, other tags may be used. For example, in several embodiments a FLAG tag (DYKDDDDK, SEQ ID NO. 19) is used. Also available are other tag sequences, such as a polyhistidine tag (His-tag) (HHHHHH, SEQ ID NO. 20), HA-tag or myc-tag. Combinations of tag types can also be used in certain embodiments. Subsequent to transduction, the stimulatory cells can be queried for presence and degree of expression of the tag, which correlates with expression of the associated stimulatory molecule. Those cells (or individual cells) with high levels of tag expression (and hence high levels of stimulatory molecule expression) can be selected and expanded (clonally if single cells are selected). Subsequently, an additional transduction with one or more additional stimulatory molecules can be performed, followed by an additional query and expansion, until the desired expression of a combination of stimulatory molecules is achieved. In some embodiments, the tag associated with each subsequent transduction is different than those of preceding transductions, so the expression of each stimulatory molecule can be independently verified.

In several embodiments, stimulatory cells are seeded into culture vessels and allowed to reach near confluence Immune cells can then be added to the culture at a desired concentration, ranging, in several embodiments from about $0.5\times10^6$ cells/cm$^2$ to about $5\times10^6$ cells/cm$^2$, including any density between those listed, including endpoints. Immune cells can be in a starting sample, such as peripheral blood, an isolated preparation of immune cells, an isolated population of NK cells, etc. depending on the embodiments. In several embodiments, blood samples are pre-processed to segregate certain populations to be expanded, e.g., NK cells. In some embodiments, a peripheral blood sample is co-cultured with the stimulatory cells, and a desired subpopulation of expanded immune cells, e.g., NK cells, is optionally isolated from the mixed population of expanded cells. Post expansion, the cells can be maintained in a suitable medium, for example, RPMI-1640, 10% FCS, and 10 IU/mL IL-2.

As discussed above, there are provided, in several embodiments, engineered cell populations (also referred to herein as stimulatory cells) suitable for activating and/or expanding a population of immune cells. In several embodiments, the engineered population is derived from a cancerous cell and is modified to express mbIL15, mb 4-1BBL, and at least one additional membrane bound molecule that stimulates immune cell activation, whereby co-culture of the engineered cells with a population of immune cells results in the activation and/or expansion of at least one subpopulation of immune cells, such as NK cells. In several embodiments, the additional molecule comprises one or more interleukins (or fragments thereof), such as IL12A, IL12B, IL18, IL21, and/or IL22. In some embodiments, the additional molecule comprises an antibody. In several embodiments, the antibody comprises a membrane bound anti-CD3 antibody (mbα-CD3), antibody or scFv, or fragments thereof. In several embodiments, the antibody is monoclonal. In several embodiments, the antibody is co-expressed with the at least one interleukin, or fragment thereof. Depending on the embodiment, one or more of the membrane bound molecules is coupled to a transmembrane domain of human CD8α. Also provided for herein are methods for expanding NK cells, wherein the NK cells are co-expressed with such engineered cells. For example, in several embodiments there is provided a method for expanding NK cells, comprising obtaining a peripheral blood sample comprising a mixed population of immune cells comprising NK cells and T cells, contacting the mixed population of cells with such engineered cell populations and co-culturing the mixed population of cells with the engineered cells for a period of time sufficient to expand the NK cells of the mixed population. In several embodiments, T cells are optionally removed, resulting in a more pure NK cell population.

In several embodiments, the cell population is derived from one or more of the following cell lines: K562 cells, Wilms tumor cell line HFWT, endometrial tumor cell line HHUA, melanoma cell line HMV-II, hepatoblastoma cell line HuH-6, lung small cell carcinoma cell lines Lu-130 or Lu-134-A, neuroblastoma cell lines NB19 or NB69, embryonal carcinoma testis cell line NEC14, cervical carcinoma cell line TCO-2, and neuroblastoma cell line TNB1. In several embodiments, the cell population lacks expression of MHC I and or/MHC II molecules.

In several embodiments, there are also provided kits comprising a plurality of nucleic acids, for use in generating the engineered cell populations to expand immune cells, the kit comprising at least 3 of: a nucleic acid encoding mbIL15, a nucleic acid encoding 4-1BBL, a nucleic acid encoding mbIL12A, a nucleic acid encoding mbIL12B, a nucleic acid encoding mbIL18, a nucleic acid encoding mbIL21, a nucleic acid encoding mbIL22, and a nucleic acid encoding mbα-CD3. In several embodiments, one or more of the nucleic acids may comprise a tag, such as GFP, FLAG tag, or HIS tag.

Further provided herein are methods of treating a subject having cancer or an infectious disease comprising administering to the subject a composition comprising genetically engineered cells described herein and/or composition comprising an expanded population of immune cells co-cultured with the genetically engineered cells described herein. As used herein, the terms "treat," "treating," and "treatment" in the context of the administration of a therapy to a subject shall be given their ordinary meaning and shall refer to the beneficial effects that a subject derives from a therapy. In certain embodiments, treatment of a subject with the administration of a composition comprising genetically engineered cells described herein and/or composition comprising an expanded population of immune cells co-cultured with the genetically engineered cells described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy.

Administration can be by a variety of routes, including, without limitation, intravenous, intraarterial, subcutaneous, intramuscular, intrahepatic, intraperitoneal and/or local delivery to an affected tissue. Doses of genetically engineered cells and/or the expanded population of immune cells co-cultured with the genetically engineered cells described herein, can be readily determined for a given subject based on their body mass, disease type and state, and desired aggressiveness of treatment, but range, depending on the embodiments, from about $10^5$ cells per kg to about $10^{12}$ cells per kg (e.g., $10^5$-$10^7$, $10^7$-$10^{10}$, $10^{10}$-$10^{12}$ and overlapping ranges therein). In one embodiment, a dose escalation regimen is used. In several embodiments, a range of expanded population of immune cells co-cultured with the genetically engineered cells described herein is administered, for example between about $1\times10^6$ cells/kg to about $1\times10^8$ cells/kg. Depending on the embodiment, various types of cancer or infection disease can be treated. Various embodiments provided for herein include treatment or prevention of the following non-limiting examples of cancers including, but not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, lung cancer (including but not limited to, non-small cell lung cancer, (NSCLC) and small cell lung cancer), pancreatic cancer, bowel cancer, lymphoma, melanoma, ocular cancer, ovarian cancer, pancreatic cancer, prostate cancer, pituitary cancer, uterine cancer, and vaginal cancer.

Further, various embodiments provided for herein include treatment or prevention of the following non-limiting examples of infectious diseases including, but not limited to, infections of bacterial origin may include, for example, infections with bacteria from one or more of the following genera: *Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, and *Yersinia*, and mutants or combinations thereof. In several embodiments, methods are provided to treat a variety to treat viral infections, such as those caused by one or more viruses, such as adenovirus, Coxsackievirus, Epstein-Barr virus, hepatitis a virus, hepatitis b virus, hepatitis c virus, herpes simplex virus, type 1, herpes simplex virus, type 2, cytomegalovirus, ebola virus, human herpesvirus, type 8, HIV, influenza virus, measles virus, mumps virus, human papillomavirus, parainfluenza virus, poliovirus, rabies virus, respiratory syncytial virus, rubella virus, and varicella-zoster virus.

In several embodiments, the expanded and/or activated cells are administered in a therapeutically effective amount (e.g., an amount that is sufficient to treat a cancer, such as by ameliorating symptoms associated with the cancer, preventing or delaying the onset of the cancer, also lessening the severity or frequency of symptoms of the cancer and/or preventing, delaying or overcoming metastasis of the cancer). The amount that will be therapeutically effective in the treatment of a particular individual will depend on the symptoms and severity of the condition (e.g., cancer), and can be determined by standard clinical techniques. In addition, in vitro or in vivo assays may optionally be employed to help identify optimal dosage ranges. The precise dose to be employed in the formulation will also depend on the route of administration, and the seriousness of the cancer, and should be decided according to the judgment of a practitioner and each patient's circumstances. Effective doses may be extrapolated from dose-response curves derived from in vitro or animal model test systems. In several embodiments, the expanded immune cells are co-administered with one or more stimulatory cells, while in some embodiments, the stimulatory cells (or one or more factors produced, secreted by, or harvested from the stimulatory cells) are administered in order to activate endogenous immune cell populations.

Methods of administration include, but are not limited to, intradermal, intramuscular, intraperitoneal, intravenous, subcutaneous, topical, oral and intranasal. Other suitable methods of introduction can also include gene therapy, rechargeable or biodegradable devices, particle acceleration devices (e.g., "gene guns") and slow release polymeric devices. The pharmaceutical compositions of this invention can also be administered as part of a combinatorial therapy with other compounds, in several embodiments.

EXAMPLES

The following are non-limiting descriptions of experimental methods and materials that were used in examples disclosed below.

Example 1—Preparation of K562 Derivatives, Expansion of NK Cells

Peripheral blood samples were obtained from discarded anonymized by-products of platelet donations from healthy adult donors at the National University Hospital Blood Bank, Singapore.

Mononucleated cells were separated by centrifugation on a Lymphoprep density step (Nycomed, Oslo, Norway) and washed twice in RPMI-1640. To purify primary NK cells from peripheral blood mononucleated cells an NK Cell Isolation Kit from Miltenyi (Bergisch Gladbach, Germany) was used.

The K562-mb15-41BBL cell line (FIG. 1A) was made as previously described (Imai C, Iwamoto S, Campana D. Genetic modification of primary natural killer cells overcomes inhibitory signals and induces specific killing of leukemic cells. *Blood.* 2005; 106:376-383; Fujisaki H, Kakuda H, Shimasaki N, et al. Expansion of highly cytotoxic human natural killer cells for cancer cell therapy. *Cancer Res.* 2009; 69(9):4010-4017.)

The other K562 variants were generated by transducing the K562-mb15-41BBL cells with a retroviral vector containing the cDNA sequence encoding membrane-bound interleukin (IL)-12, IL-18, or both, or membrane-bound anti-human CD3 ScFv. The sequences for the cloning constructs are provided in SEQ ID NO: 21 (mbIL15), SEQ ID NO: 23 (mbIL12A), SEQ ID NO: 24 (mbIL12B), SEQ ID NO: 25 (mbIL18), and SEQ ID NO: 26 (mb-anti-CD3 scFv). A RD144-pseudotyped MSCV retrovirus containing the corresponding cDNA was used to transduce the K562-mb15-41BBL cells. Retroviral vector-conditioned medium was added to RetroNectin (Takara, Otsu, Japan)-coated polypropylene tubes; after centrifugation and removal of the supernatant, K562-mb15-41BBL cells were added to the tubes and left at 37° C. for 12 hours; fresh viral supernatant was added on two other successive days. Cells were then maintained in RPMI-1640 with FBS and antibiotics.

Surface expression of IL-12a, IL12b and IL18 was analyzed by flow cytometry using the antibodies anti-IL12a conjugated to allophycocyanin (APC; Miltenyi) or to phycoerythrin (PE; R&D Systems, Minneapolis, MN), anti-IL12b APC (Biolegend, San Diego, CA), anti-IL18 (MBL; Woburn, MA) followed by goat-anti-mouse IgG1 PE (Southern Biotechnology Associates, Birmingham, AL). Anti-CD3 was detected using a goat-anti-mouse Fab2 antibody conjugated to biotin followed by streptavidin APC (both from Jackson Immunoresearch (West Grove, PA). Subclones expressing high levels of the transgene were enriched by flow cytometry and used to stimulate NK cell expansion.

Human NK Cell Expansion

To expand NK cells, PBMCs and the genetically modified K562 cells were co-cultured. Briefly, peripheral blood mononucleated cells ($3\times10^6$) were cultured in a 6-well tissue culture plate with $2\times10^6$ irradiated (100 Gy) K562-modified cells in SCGM medium (CellGenix, Freiburg, Germany) containing 10% FBS and 40 IU/mL human interleukin (IL)-2 (Novartis, Basel, Switzerland). Every 2-3 days, fresh tissue culture medium and IL-2 was added. After 7 days of co-culture, residual T cells were removed using Dynabeads CD3 (Thermo Fisher), producing cell populations containing >90% CD56+CD3-NK cells.

Results

After generating the constructs and transducing the K562-mb15-41BBL cells with the respective retroviral vector, the K562 cells were evaluated using flow cytometry for expression of the various membrane bound molecules. FIG. 2A-2F depict the results of the evaluation. As depicted, each of the six molecules to be expressed showed that nearly 100% of the resulting K562 cell lines expressed the indicated molecule (2A—mbIL15, 2B—41BBL, 2C—mbIL18, 2D—mbIL12A, 2E—mbIL12B, and 2F—mb-anti-CD3). These data demonstrate that the various constructs generated successfully translate into expression of the desired stimulatory molecule by the K562 cells (or other type of stimulatory cell).

Figures 3A, 3B:
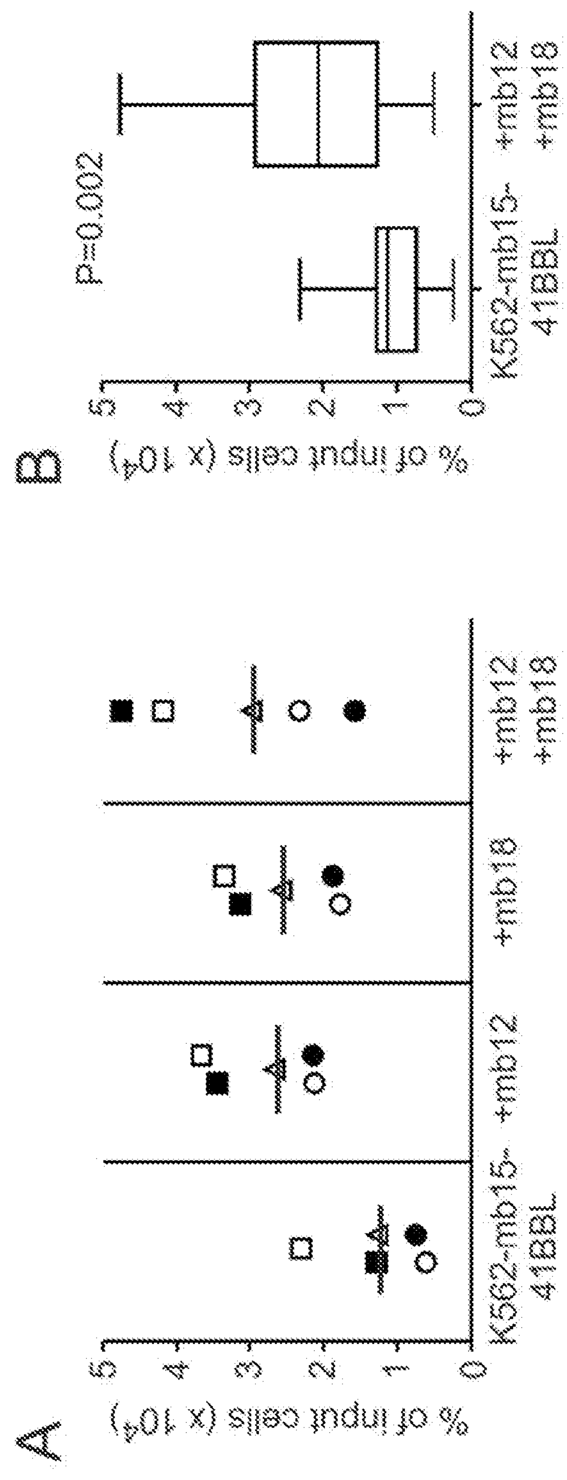
FIGS. 3A-3B depict data related to the expansion of NK cells by various K562 constructs according to several embodiments disclosed herein.

Having confirmed expression of the desired stimulatory molecule, the ability of the various K562 variants to expand NK cells was evaluated. As discussed above, PBMCs were co-cultured with irradiated K562 cells co-expressing mbIL15 and 4-1BBL (K562-mb15-41BBL). This K562 construct was compared to a construct additionally expressing mbIL12 (+mb12), mbIL18 (+mb18), or both mbIL12 and mbIL18 (+mb12+mb18). The number of NK cells (defined by the expression of CD56 and the lack of CD3) recovered after 7 days of culture relative to those initially seeded was calculated and is depicted in FIG. 3A. In all cultures, IL-2 40 IU/mL (Aldeuskin, Novartis) was added. Results of 5 experiments with cells from 4 healthy donors are shown. Horizontal bar corresponds to median value. These data indicate a clear trend towards enhanced NK cell expansion with the addition of mbIL12, mbIL18, and a combination of both. This suggests that supplementing the stimulatory nature of mblL15-41BBL expressing K562 cells is accomplished using the constructs according to several embodiments herein.

FIG. 3B shows an additional experiment comparing NK cell through co-culture of PBMCs with K562-mb15-41BBL cells or with K562-mb15-41BBL cells expressing mb12 and mb18 for 7 days of culture. This data is from 12 experiments with peripheral blood mononucleated cells from 8 donors. P value was calculated by paired t test. These data demonstrate that a significant increase in the degree of NK cells (as compared to the starting population. Thus, the constructs according to several embodiments disclosed herein result in the significant expansion of NK cell populations. This expansion is particularly advantageous, in several embodiments, because the K562 cells expression multiple stimulatory molecules result in an unexpectedly robust expansion of NK cells, leading to a sizeable population that can be used in therapeutic applications.

Figures 4A, 4B, 4C, 4D, 4E, 4F:
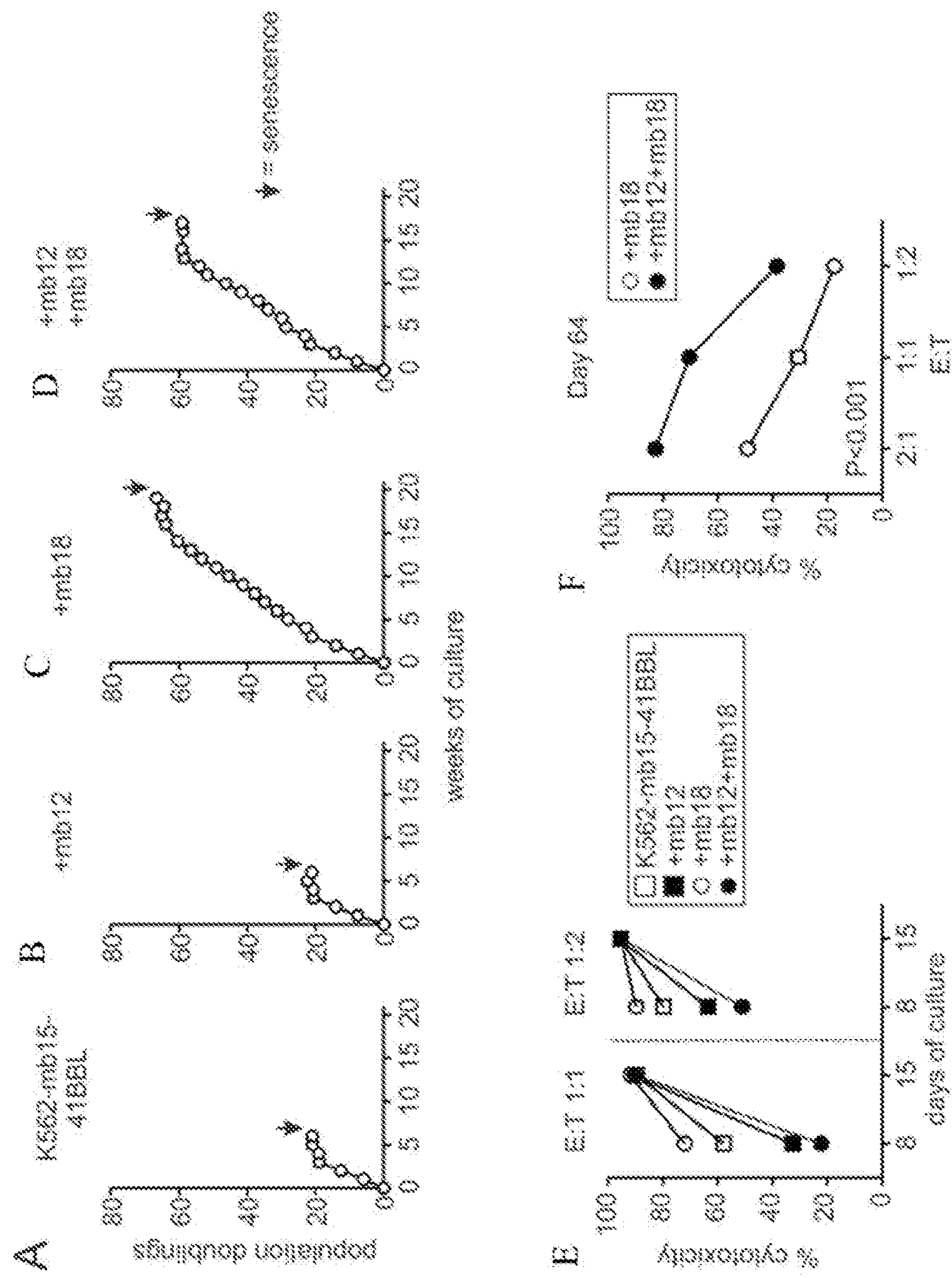
FIGS. 4A-4F depict data related to the long-term expansion and function of NK cells stimulated with various genetically-modified K562 cells.

Example 2—Long Term Expansion and Function of NK Cells Stimulated with K562 Variants Long-Term Expansion The ability of NK cells to continue to expand was evaluated. PBMCs were co-cultured with irradiated K562 cells expressing mbIL15 and 4-1BBL (K562-mb15-41BBL) (FIG. 4A), or with K562-mb15-41BBL cells also expressing mbIL12 (+mb12) (FIG. 4B), mbIL18 (+mb18) (FIG. 4C), or both mbIL12 and mbIL18 (+mb12+mb18) (FIG. 4D). The number of NK cells (defined by the expression of CD56 and the lack of CD3) recovered after different time intervals in each culture relative to those originally seeded was calculated to compute the cell population doublings. To renew the potential expansion of the NK cells, fresh genetically-modified K562 cells were added every 2 weeks, at a K562: NK ratio of 5:1, and IL-2 concentration was maintained at 40 IU/mL during the first week and at 400 IU/mL subsequently, after T cell depletion. Arrows indicate the time point at which NK cells stopped expanding despite addition of K562 cells, indicating senescence.

As with the expansion data discussed above, these data indicate that expression of mbIL15-41BBL result in a threshold level of expansion, while the expression of additional stimulatory molecules results in significant enhancements of expansion, in several embodiments. In particular, expression of mbIL12 alone did not appear to alter the ability of NK cells to continue to expand beyond that accomplished using the mbIL15-41BBL expressing cells. However, both the mbIL18 and combination mbIL12-mbIL18 expressing K562 cells resulted in significantly longer durations of NK cell expansions, with each construct stimulating NK cell expansion for nearly 20 weeks (~3 fold greater than the mbIL15-41BBL expressing K562 cells). This demonstrates that, in accordance with several embodiments disclosed herein, the expression of certain stimulatory molecules can unexpectedly enhance NK cell expansion. Additionally, according to several embodiments, co-expressing multiple stimulatory molecules can result in synergistic stimulatory effects.

Cytotoxicity Assays

In addition to the expansion of NK cells, the cytotoxicity of the expanded cells was evaluated to determine whether certain engineered variants of stimulatory cells imparted a greater degree of cytotoxicity to the expanded NK cells.

Target cells were suspended in RPMI-1640 with 10% FBS, labeled with calcein AM (Sigma), and plated into 96-well flat bottom plates (Costar, Corning, NY). Expanded NK cells, suspended in RPMI-1640 with 10% FBS were then added at various E:T ratios as indicated, and co-cultured with target cells for 4 hours. Cells were then stained with propridium iodide and cytotoxicity was measured by flow cytometry using an Accuri flow cytometer (BD Bioscience), enumerating the number of viable target cells (calcein AM-positive, propidium-iodide negative, and light scattering properties of viable cells).

FIG. 4E depicts data from measurements of NK cell cytotoxicity against K562 cells in 4-hour assays at the effector:target (E:T) ratios shown after 8 and 15 days of culture. At the initial 8-day time point, at both E:T ratios, the NK cells stimulated with different constructs exhibited differential cytotoxicity. As shown, those NK cells expanded for 8 days with the mbIL15-41BBL+mbIL18 construct and the mbIL15-41BBL showed the greatest cytotoxicity. Interestingly, in those groups cultured for an additional 7 days in culture (15 days in total, with IL-2 at 4400 IU/mL for the second week), the differences in cytotoxicity were reduced, with all groups exhibiting cytotoxic effects at near 100%.

FIG. 4F depicts data related to NK cell cytotoxicity after 64 days in culture (9 weeks in culture), using the E:T ratios shown. These data demonstrate that, even after a substantial amount of time in culture, cytotoxicity is still exhibited. At 1:1 E:T, the NK cells expanded using K562 cells expressing mbIL15-41BBL+mbIL18 demonstrated approximately 30% cytotoxicity, while NK cells expanded using the K562 cells expressing mbIL15-41BBL+mbIL12+mbIL18 demonstrated almost 80% cytotoxicity. When outnumbered by target cells (E:T of 1:2), the respective NK cells still exhibited cytotoxicity, though it was reduced compared to the 1:1 ratio. In contrast, when present in greater quantities than target cells (E:T of 2:1), the NK cells exhibited greater cytotoxicity. These data suggest that, when cultured for long periods of time, there may be a reduction in the potency of the NK cells (albeit with an increase in number). Thus, according to some embodiments, an increased duration of co-culture not only increases the raw number of NK cells, it also leads to an increase in the cytotoxic effects of each NK cell. Accordingly, some embodiments not only result in greater NK cell numbers, but the potency of each member of the expanded NK cell population is enhanced, thereby resulting in overall greater clinical efficacy. According to several embodiments, the duration of culture vs. potency is balanced to strike an optimal balance between cell number and the resultant cytotoxic effects.

In several embodiments, a nucleic acid encoding 4-1BBL comprises, consists essentially of or consists of the nucleic acid sequence of SEQ ID NO. 22 shown below (SEQ ID NO. 22)

```
gaattcgccc ttccaccatg gaatacgcct ctgacgcttc
actggacccc gaagccccgt ggcctcccgc gccccgcgct
cgcgcctgcc gcgtactgcc ttgggccctg gtcgcggggc
tgctgctgct gctgctgctc gctgccgcct gcgccgtctt
cctcgcctgc ccctgggccg tgtccggggc tcgcgcctcg
cccggctccg cggccagccc gagactccgc gagggtcccg
agctttcgcc cgacgatccc gccggcctct tggacctgcg
gcagggcatg tttgcgcagc tggtggccca aaatgttctg
ctgatcgatg ggcccctgag ctggtacagt gacccaggcc
tggcaggcgt gtccctgacg gggggcctga gctacaaaga
ggacacgaag gagctggtgg tggccaaggc tggagtctac
tatgtcttct ttcaactaga gctgcggcgc gtggtggccg
gcgagggctc aggctccgtt tcacttgcgc tgcacctgca
gccactgcgc tctgctgctg gggccgccgc cctggctttg
accgtggacc tgccacccgc ctcctccgag gctcggaact
cggccttcgg tttccagggc cgcttgctgc acctgagtgc
cggccagcgc ctgggcgtcc atcttcacac tgaggccagg
gcacgccatg cctggcagct tacccagggc gccacagtct
tgggactctt ccgggtgacc cccgaaatcc cagccggact
cccttcaccg aggtcggaat aactcgag.
```

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a population of expanded NK cells" includes "instructing the administration of a population of expanded NK cells." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "90%" includes "90%." In some embodiments, at least 95% homologous includes 96%, 97%, 98%, 99%, and 100% homologous to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

Articles such as "a", "an", "the" and the like, may mean one or more than one unless indicated to the contrary or otherwise evident from the context. The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process. Any one or more claims may be amended to explicitly exclude any embodiment, aspect, feature, element, or characteristic, or any combination thereof. Any one or more claims may be amended to exclude any agent, composition, amount, dose, administration route, cell type, target, cellular marker, antigen, targeting moiety, or combination thereof.

What is claimed is:

1. A genetically engineered cell population that does not express major histocompatibility complex (MHC) I molecules, wherein said genetically engineered cell population is derived from K562 cells, wherein said genetically engineered cell population is modified to express membrane-bound interleukin-15 (mbIL15), wherein the mbIL15 comprises the amino acid sequence of SEQ ID NO: 2, wherein said genetically engineered cell population is modified to express membrane-bound 4-1BB ligand (mb4-1BBL) comprising the amino acid sequence of SEQ ID NO: 14, wherein said genetically engineered cell population is modified to express membrane-bound interleukin-18 (mbIL18), wherein the mbIL18 comprises the amino acid sequence of SEQ ID NO: 8, wherein said genetically engineered cell population is modified to express membrane-bound interleukin-12A (mbIL12A), wherein the mbIL12A comprises the amino acid sequence of SEQ ID NO: 4, wherein said genetically engineered cell population is modified to express membrane-bound interleukin-12B (mbIL12B), wherein the mbIL12B comprises the amino acid sequence of SEQ ID NO: 6, wherein said genetically engineered cell population does not express major histocompatibility complex (MHC) I molecules, and wherein co-culture of said genetically engineered cell population with a population of natural killer (NK) cells results in the activation and expansion of the NK cells.

2. The genetically engineered cell population of claim 1, wherein the genetically engineered cell population lacks expression of MHC II molecules.

3. The genetically engineered cell population of claim 1, wherein the genetically engineered cell population is further modified to express:

membrane-bound interleukin-21 (mbIL21) comprising the sequence of SEQ ID NO: 10; or membrane-bound interleukin-22 (IL22) comprising the sequence of SEQ ID NO: 12.

4. The genetically engineered cell population of claim 1, wherein the cells further comprise a membrane-bound anti-CD3 antibody (mbα-CD3), an antibody fragment thereof, or an anti-CD3 scFv.

5. The genetically engineered cell population of claim 4, wherein the mbα-CD3 is a monoclonal antibody.

6. The genetically engineered cell population of claim 5, wherein the mbα-CD3 targets an epitope within the epsilon subunit of the CD3 receptor.

7. A genetically engineered cell population that does not express major histocompatibility complex (MHC) I molecules, wherein said genetically engineered cell population is derived from K562 cells, wherein said genetically engineered cell population is modified to express membrane-bound interleukin-15 (mbIL15), wherein the mbIL15 is encoded by a nucleic acid sequence that comprises SEQ ID NO: 1, wherein said genetically engineered cell population is modified to express membrane-bound 4-1BB ligand (mb4-1BBL) comprising the amino acid sequence of SEQ ID NO: 14, wherein said genetically engineered cell population is modified to express membrane-bound interleukin-18 (mbIL18), wherein the mbIL18 comprises the amino acid sequence of SEQ ID NO: 8, wherein said genetically engineered cell population is modified to express membrane-bound interleukin-12A (IL12A), wherein the mbIL12A comprises the amino acid sequence of SEQ ID NO: 4, wherein said genetically engineered cell population is modified to express membrane-bound interleukin-12B (IL12B), wherein the mbIL12B comprises the amino acid sequence of SEQ ID NO: 6, wherein said genetically engineered cell population does not express major histocompatibility complex (MHC) I molecules, and wherein co-culture of said genetically engineered cell population with a population of natural killer (NK) cells results in the activation and expansion of the NK cells.

8. The genetically engineered cell population of claim 7, wherein the amino acid sequence of SEQ ID NO:14 is encoded by a nucleic acid sequence that comprises SEQ ID NO: 13.

9. The genetically engineered cell population of claim 7, wherein the engineered cell population is further modified to express membrane-bound interleukin-21 or membrane-bound interleukin-22.

* * * * *